(12) United States Patent
Nishiyama et al.

(10) Patent No.: US 11,555,082 B2
(45) Date of Patent: Jan. 17, 2023

(54) P-BORONOPHENYLALANINE DERIVATIVE AND COMPOSITION CONTAINING SAME, AND KIT FOR PRODUCING SAID DERIVATIVE AND COMPOSITION

(71) Applicants: TOKYO INSTITUTE OF TECHNOLOGY, Tokyo (JP); STELLA PHARMA CORPORATION, Osaka (JP)

(72) Inventors: Nobuhiro Nishiyama, Tokyo (JP); Takahiro Nomoto, Tokyo (JP); Yukiya Inoue, Tokyo (JP); Ying Yao, Tokyo (JP); Kaito Kanamori, Tokyo (JP); Hiroyasu Takemoto, Tokyo (JP); Makoto Matsui, Tokyo (JP); Keishiro Tomoda, Tokyo (JP)

(73) Assignee: TOKYO INSTITUTE OF TECHNOLOGY, Osaka (JP)

( * ) Notice: Subject to any disclaimer, the term of this patent is extended or adjusted under 35 U.S.C. 154(b) by 107 days.

(21) Appl. No.: 16/963,864

(22) PCT Filed: Feb. 19, 2019

(86) PCT No.: PCT/JP2019/006158
§ 371 (c)(1),
(2) Date: Jul. 22, 2020

(87) PCT Pub. No.: WO2019/163790
PCT Pub. Date: Aug. 29, 2019

(65) Prior Publication Data
US 2021/0040244 A1    Feb. 11, 2021

(30) Foreign Application Priority Data
Feb. 20, 2018 (JP) .............................. JP2018-028007

(51) Int. Cl.
| | | |
|---|---|---|
| *C08F 8/42* | (2006.01) |
| *C08F 16/06* | (2006.01) |
| *A61K 47/60* | (2017.01) |
| *A61P 35/00* | (2006.01) |
| *A61K 9/00* | (2006.01) |
| *A61K 31/69* | (2006.01) |

(52) U.S. Cl.
CPC .............. *C08F 8/42* (2013.01); *A61K 9/0019* (2013.01); *A61K 31/69* (2013.01); *A61K 47/60* (2017.08); *A61P 35/00* (2018.01); *C08F 16/06* (2013.01)

(58) Field of Classification Search
CPC ................................... C08F 8/42; C08F 16/06
See application file for complete search history.

(56) References Cited

U.S. PATENT DOCUMENTS

| | | | |
|---|---|---|---|
| 6,169,076 B1 * | 1/2001 | Shull ....................... | C07H 1/00 514/23 |
| 10,799,587 B2 | 10/2020 | Niu et al. | |
| 2017/0326236 A1 | 11/2017 | Niu et al. | |

FOREIGN PATENT DOCUMENTS

TW          201739460 A    11/2017

* cited by examiner

*Primary Examiner* — Shawquia Jackson
(74) *Attorney, Agent, or Firm* — Mintz Levin Cohn Ferris Glovsky and Popeo, P.C.

(57) ABSTRACT

The present invention pertains to: a p-boronophenylalanine derivative that comprises a polymer to which a group represented by formula (I) is linked directly or via a linker; a composition containing same; and a kit for producing said derivative and composition.

15 Claims, 31 Drawing Sheets

P-BORONOPHENYLALANINE DERIVATIVE AND COMPOSITION CONTAINING SAME, AND KIT FOR PRODUCING SAID DERIVATIVE AND COMPOSITION

FIELD

The present invention relates to a p-boronophenylalanine derivative (hereinafter also referred to as "BPA derivative"), a composition containing the same, and a kit for producing the same.

BACKGROUND

Boron neutron capture therapy (BNCT) is a method that involves accumulating boron ($^{10}B$) in a diseased part and performing neutron irradiation thereon to cause a nuclear reaction which locally generates α-rays that kill target cells. Accumulation of boron in the diseased part is performed by administering a boron drug. Drugs that have been applied to humans to date include a boron cluster of mercaptoundecahydrododecaborate (BSH), which is a first generation boron drug, and p-boronophenylalanine (BPA), which is a second generation boron drug. Further, third generation boron drugs in which a boron cluster is loaded on a carrier such as a liposome, polymer, polymer micelle, etc. have been reported (NPL1).

BSH has excellent solubility in water but has poor tumor selectivity. Third generation boron drugs containing BSH can selectively deliver boron to tumors due to the enhanced permeability and retention effect (EPR effect) by using carriers such as liposomes, polymers, and polymer micelles. However, since the EPR effect is generally realized by a carrier exhibiting long term retention in the blood, it is difficult to increase the tumor/blood boron concentration ratio when third generation boron drugs are used.

It is known that the phenylalanine structure of BPA is recognized by, for example, the amino acid transporter (LAT1), which is overexpressed in tumor cells, and BPA is selectively taken up by tumor cells (NPL2). However, BPA has poor solubility in water.

It has been reported that the issue of the poor solubility of BPA can be improved by forming complexes with sugars such as fructose or sorbitol as solubilizers (PTL 1).

CITATION LIST

Patent Literature

[PTL 1] Japanese Unexamined Patent Publication (Kokai) No. 2009-51766

Non-Patent Literature

[NPL1] Luderer M. J. et al., Phar. Res., 32, 2824-2836 (2015)
[NPL2] Wongthai P. et al., Cancer Sci. 106, 279-286 (2015)

SUMMARY

Technical Problem

With first generation and third generation boron drugs, it is difficult to increase the capacity thereof to accumulate in tumors while maintaining the tumor/normal tissue boron concentration ratio and tumor/blood boron concentration ratio at a high level. On the other hand, this can be achieved at a certain time with second generation BPA.

However, since BPA is taken up into cancer cells mainly through the amino acid transporter LAT1, which is an exchange transporter, as the extracellular BPA concentration decreases, intracelulluar BPA flows out of the cell. Thus, there was a problem that after boron had accumulated in tumor tissue, the boron concentration in the tumor would decrease at an early stage.

The method in PTL 1 can improve the water solubility of BPA but cannot resolve the problem of early elimination of BPA from tumor cells. As an approach for dealing with this problem, a method has been carried out in which BPA was administered by drip to maintain the intratumoral boron concentration at a level required for treatment while neutron irradiation of a diseased part was performed. However, in this case, as a large amount of boron is present in normal blood vessels, there is concern that normal tissue is exposed to radiation.

Thus, the object of the present invention is to resolve the problem of early elimination of BPA from tumor cells such that selective accumulation and long term retention of boron in tumors are realized, while achieving an excellent tumor/normal tissue boron concentration ratio and tumor/blood boron concentration ratio.

Solution to Problem

With respect to the above problem, as a result of extensive research carried out by the present inventors, it was found that a boron delivery system in which BPA is carried on a polymer is taken up by tumor cells by endocytosis via an amino acid transporter and that high intracellular boron concentrations could be maintained for a long time compared to conventional BPA. Thereby the present invention was achieved.

Specifically, the present invention encompasses the following <1> to <21>.

<1>
A p-boronophenylalanine derivative comprising:
a polymer linked, either directly or via a linker, to a group represented by formula (I) below

[Chem. 1]

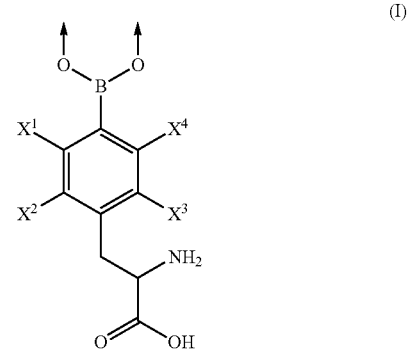

wherein,
the arrows indicate a bond with an adjacent atom, and $X^1$ to $X^4$ are each independently H, $^{18}F$, or $^{19}F$.

<2>
The p-boronophenylalanine derivative according to <1>, wherein two or more of the groups represented by formula (I) are linked directly or via a linker to the polymer, and wherein the groups represented by formula (I) may be the same or different.

<3>

The p-boronophenylalanine derivative according to <1> or <2>, wherein the number average molecular weight thereof is 1,000 Da or more.

<4>

The p-boronophenylalanine derivative according to any one of <1> to <3>, wherein the polymer is selected from the group consisting of polyvinyl alcohol, polyester, polyether, polyacrylate, polyacrylamide, polypeptide, polysaccharide, and copolymers thereof.

<5>

The p-boronophenylalanine derivative according to any one of <1> to <4>, wherein the polymer is a polyvinyl alcohol.

<6>

The p-boronophenylalanine derivative according to <5>, wherein the p-boronophenylalanine derivative is represented by formula (II) below or a pharmaceutically acceptable salt thereof.

[Chem. 2]

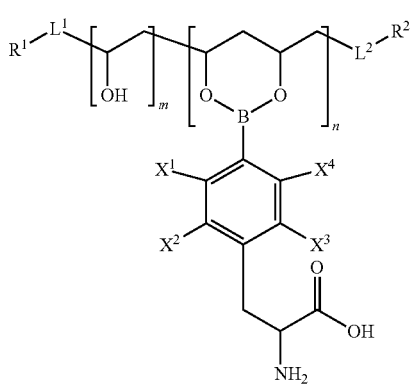

(II)

wherein, $X^1$ to $X^4$ are each independently H, $^{18}F$, or $^{19}F$, $L^1$ and $L^2$ are each independently a linker or absent, $R^1$ and $R^2$ are each independently hydrogen, a hydroxy group, a carboxyl group, an amino group, a $C_{1-10}$ alkyl group that may be substituted with a halogen, a $C_{1-10}$ alkoxy group that may be substituted with a halogen, a thiol group, a cyano group, an azide group, a —CH(OA$^1$)$_2$, or a detectable label, $A^1$ is a $C_{1-6}$ alkyl group, m=0 to 3,998, n=1 to 2,000, m+2n=10 to 4,000, and the order of the repeating units is arbitrary.

<7>

The p-boronophenylalanine derivative according to any one of <1> to <4>, wherein the polymer is a polypeptide.

<8>

The p-boronophenylalanine derivative according to <7>, wherein the p-boronophenylalanine derivative is represented by formula (III) below or a pharmaceutically acceptable salt thereof.

[Chem. 3]

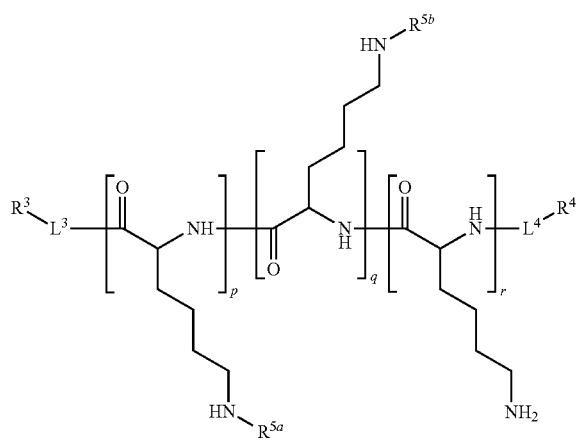

(III)

wherein, $L^3$ and $L^4$ are each independently a linker or absent, $R^3$ and $R^4$ are each independently hydrogen, a hydroxy group, a carboxyl group, an amino group, a $C_{1-10}$ alkyl group that may be substituted with a halogen, a $C_{1-10}$ alkoxy group that may be substituted with a halogen, a thiol group, a cyano group, an azide group, a —CH(OA$^1$)$_2$, or a detectable label, $A^1$ is a $C_{1-6}$ alkyl group, $R^{5a}$ are each independently a group represented by (IV-a) or (IV-b) below,

[Chem 4]

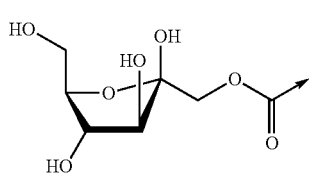

(IV-a)

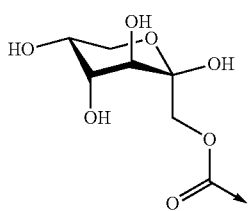

(IV-b)

wherein, the arrows indicate a bond with NH, $R^{5b}$ are each independently a group selected from the group consisting of groups represented by the following formulas (IV-c) to (IV-g),

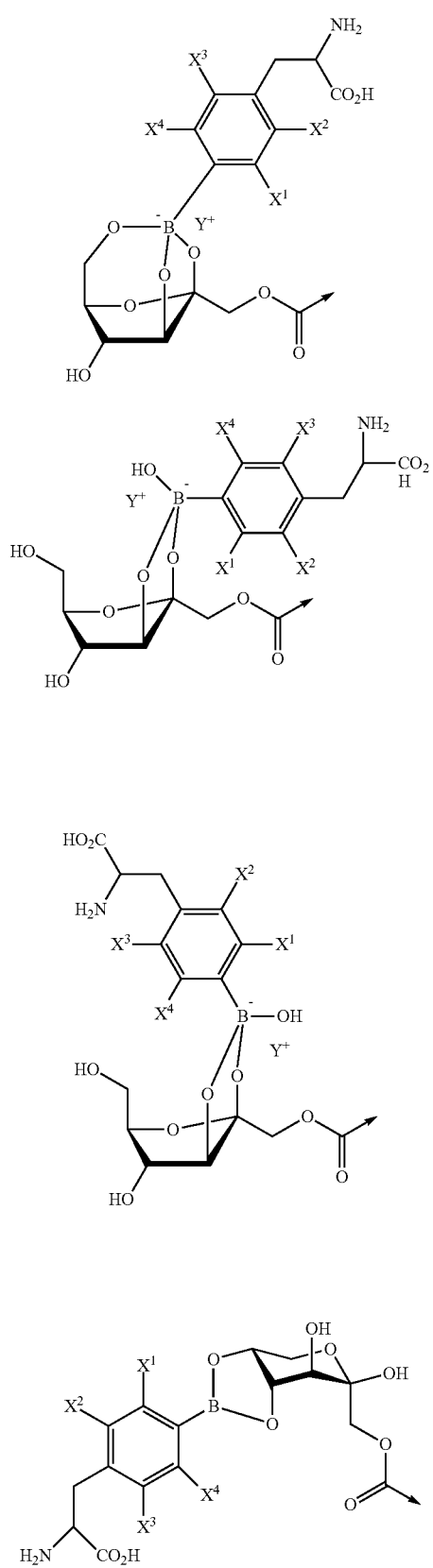

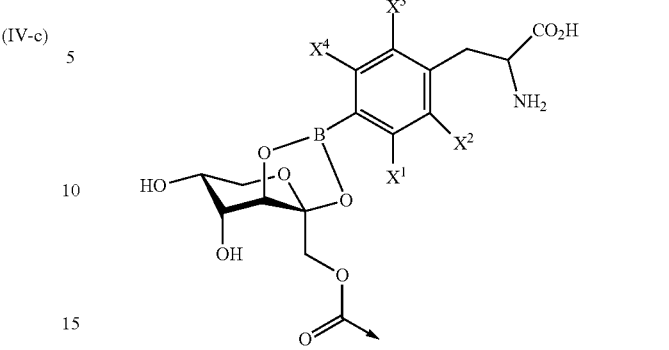

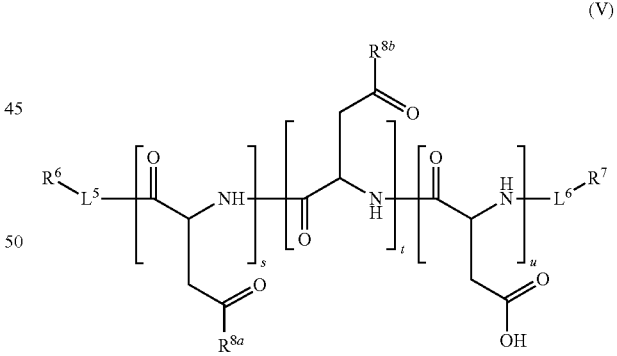

wherein the arrows indicate a bond with NH, $X^1$ to $X^4$ each independently represent H, $^{18}F$ or $^{19}F$, $Y^+$ represents $H^+$, an alkali metal ion, or a tetra-$C_{1-6}$ alkyl-ammonium ion, p=0 to 299, q=1 to 300, r=0 to 299, p+q+r=10 to 300, and the order of the repeating units is arbitrary.

<9>

The p-boronophenylalanine derivative according to <7>, wherein the p-boronophenylalanine derivative is represented by formula (V) below or a pharmaceutically acceptable salt thereof,

[Chem. 6]

wherein, $L^5$ and $L^6$ are each independently a linker or absent, $R^6$ and $R^7$ are each independently a hydrogen, a hydroxy group, a carboxyl group, an amino group, a $C_{1-10}$ alkyl group that may be substituted with a halogen, a $C_{1-10}$ alkoxy group that may be substituted with a halogen, a thiol group, a cyano group, an azide group, a —CH(OA$^1$)$_2$ or a detectable label, $A^1$ is a $C_{1-6}$ alkyl group,
$R^{8a}$ is a group represented by (VI-a) below,
[Chem. 7]
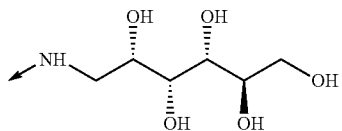
(VI-a)
wherein, the arrow indicates a bond with a carbonyl carbon,
$R^{8b}$ are each independently a group selected from the group consisting of groups represented by formulas (VI-b) to (VI-h) below,
[Chem 8]
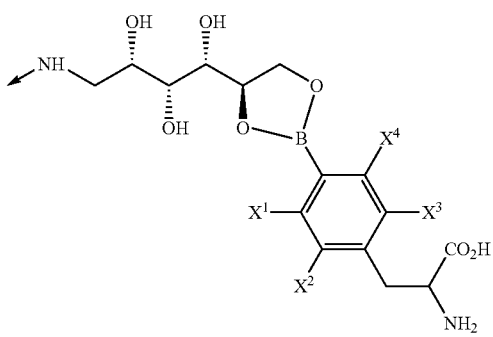
(VI-b)
(VI-c)
(VI-d)
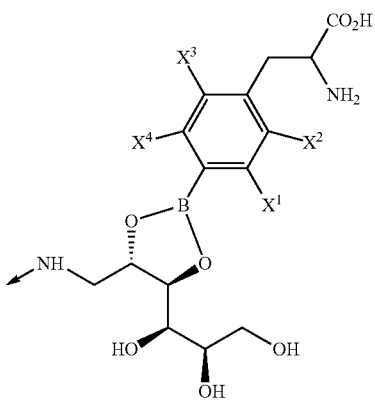
(VI-e)
(VI-f)
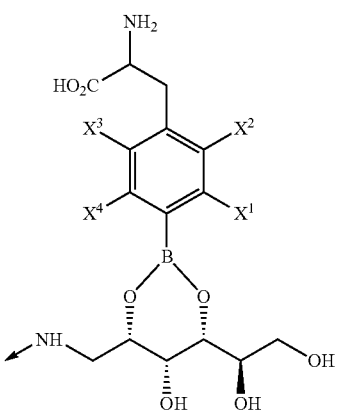
(VI-g)
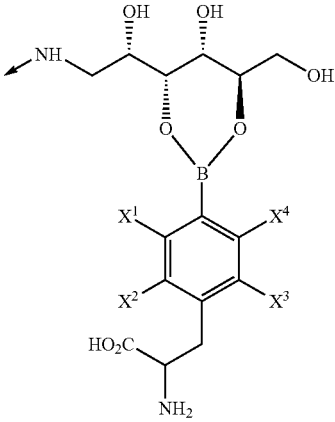
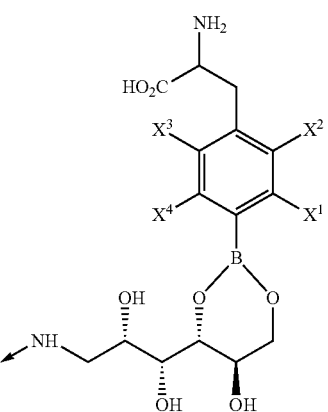
(VI-h)

wherein, the arrows indicate a bond with a carbonyl carbon, $X^1$ to $X^4$ are each independently H, $^{18}F$, or $^{19}F$, s=0 to 299, t=1 to 300, u=0 to 299, s+t+u=2 to 300, and the order of the repeating units is arbitrary.

<10>

The p-boronophenylalanine derivative according to <7> wherein the p-boronophenylalanine derivative is represented by formula (XX) below or a pharmaceutically acceptable salt thereof,

[Chem. 9]

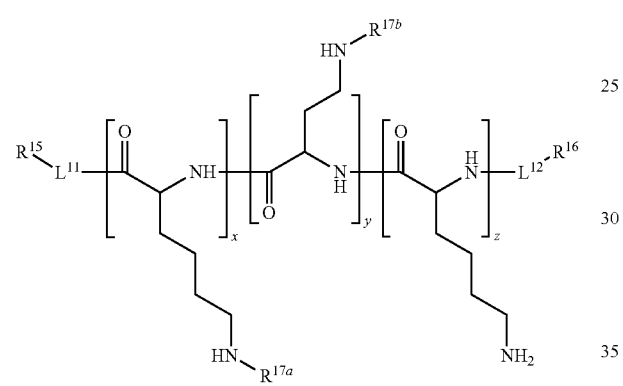

(XX)

wherein $L^{11}$ and $L^{12}$ are each independently a linker or absent, $R^{15}$ and $R^{16}$ are each independently hydrogen, a hydroxy group, a carboxyl group, an amino group, a $C_{1-10}$ alkyl group that may be substituted with a halogen, a $C_{1-10}$ alkoxy group that may be substituted with a halogen, a thiol group, a cyano group, an azide group, a —CH(OA$^1$)$_2$ or a detectable label, $A^1$ is a $C_{1-6}$ alkyl group, $R^{17a}$ is a group represented by the formula (XXI-a) below,

[Chem 10]

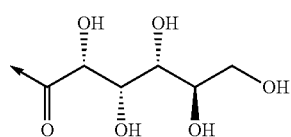

(XXI-a)

wherein, the arrow indicates a bond with NH, $R^{17b}$ are each independently a group selected from the group consisting of groups represented by formulas (XXI-b) to (XXI-h) below,

[Chem. 11]

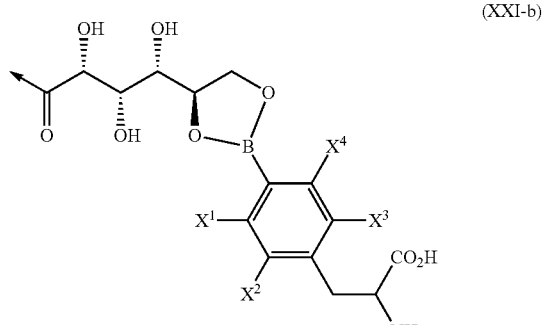

(XXI-b)

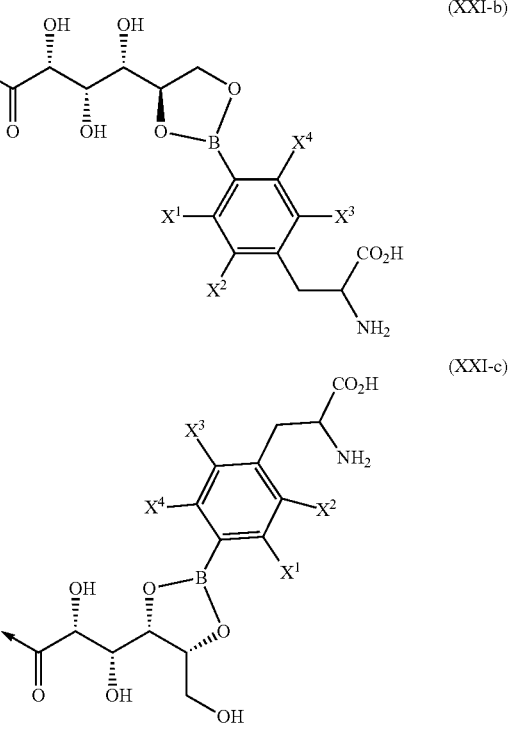

(XXI-c)

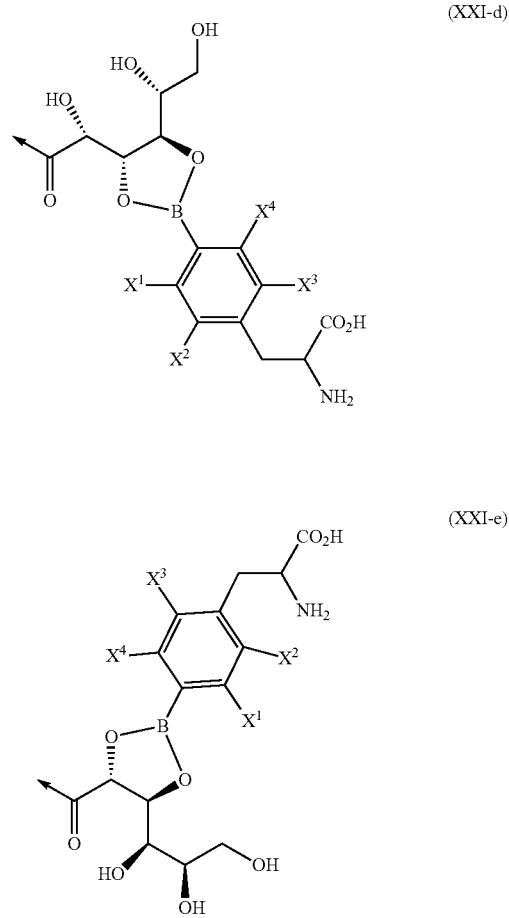

(XXI-d)

(XXI-e)

-continued (XXI-f)

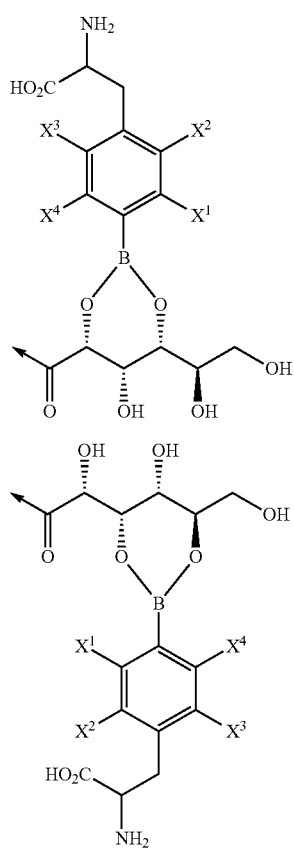

(XXI-g)

(XXI-h)

wherein,
the arrows indicate a bond with NH,
$X^1$ to $X^4$ are each independently H, $^{18}F$, or $^{19}F$,
x=0 to 299,
y=1 to 300,
z=0 to 299,
x+y+z=10 to 300, and
the order of the repeating units is arbitrary.

<11>

The p-boronophenylalanine derivative according to <5>, wherein the p-boronophenylalanine derivative is represented by formula (XXII) below or a pharmaceutically acceptable salt thereof,

[Chem 12]

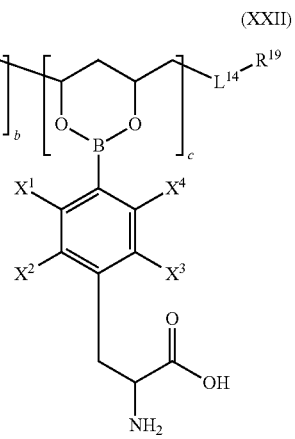

(XXII)

wherein,
$X^1$ to $X^4$ are each independently H, $^{18}F$ or $^{19}F$,
$L^{13}$ and $L^{14}$ are each independently a linker or absent,
$R^{18}$ and $R^{19}$ are each independently a hydrogen, a hydroxy group, a carboxyl group, an amino group, a $C_{1-10}$ alkyl group that may be substituted with a halogen, a $C_{1-10}$ alkoxy group that may be substituted with a halogen, a thiol group, a cyano group, an azide group, a —$CH(OA^1)_2$ or a detectable label,
$A^1$ is a $C_{1-6}$ alkyl group,
$R^{20}$ are each independently a $C_{1-10}$ alkyl group that may be substituted with a halogen, an —$NR^{21}R^{22}$ group, or the following group,

[Chem 13]

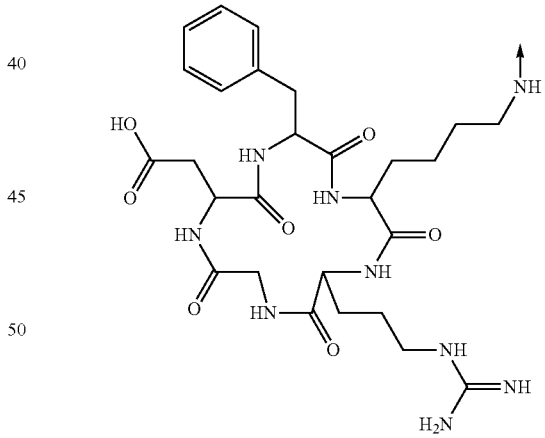

wherein, the arrow indicates a bond with a carbonyl carbon,
$R^{21}$ and $R^{22}$ are each independently a hydrogen or a $C_{1-10}$ alkyl group that may be substituted with a halogen,
a=1 to 3,998,
b=0 to 3,997,
c=1 to 2,000,
a+b+2c=10 to 4,000, and
the order of the repeating units is arbitrary.

<12>

A composition comprising the p-boronophenylalanine derivative according to any one of <1> to <11>.

<13>
The composition according to <12> for treating tumors.
<14>
The composition according to <12> for diagnosing and detecting tumors.
<15>
A kit for producing the composition according to any one of <10> to <12> or for producing the p-boronophenylalanine derivative according to any one of <1> to <9> comprising a compound represented by formula (VII)

[Chem 14]

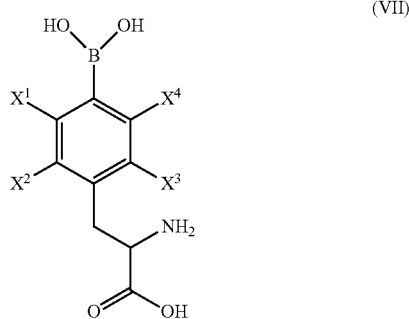

(VII)

wherein,
X¹ to X⁴ are each independently H, $^{18}$F or $^{19}$F, and
a polymer that can react with the compound represented by formula (VII) to form a p-boronophenylalanine derivative according to any one of <1> to <11>.
<16>
A tumor treatment method comprising administering to a subject in need thereof an effective dosage of the p-boronophenylalanine derivative according to any one of <1> to <11>.
<17>
A tumor diagnosis or detection method comprising administering to a subject in need thereof an effective dosage of the p-boronophenylalanine derivative according to any one of <1> to <11>.
<18>
The p-boronophenylalanine derivative according to any one of <1> to <11> for treating tumors.
<19>
The p-boronophenylalanine derivative according to any one of <1> to <11> for diagnosing and detecting tumors.
<20>
Use of the p-boronophenylalanine derivative according to any one of <1> to <11> in the production of a drug for treating tumors.
<21>
Use of the p-boronophenylalanine derivative according to any one of <1> to <11> in the production of a drug for diagnosing or detecting tumors.

Advantageous Effects of Invention

By using the p-boronophenylalanine derivative of the present invention, selective accumulation, and long-term retention of boron in tumors can be realized, while achieving an excellent tumor/normal tissue boron concentration ratio and tumor/blood boron concentration ratio.

BRIEF DESCRIPTION OF DRAWINGS

FIG. 3-1 is a graph showing intracellular boron concentration. The results are shown as mean±S.D. (n=3). The statistical significance was calculated by the t-test. * p<0.05, ** p<0.01.

FIG. 3-2 is a graph showing intracellular boron concentration. The results are shown as mean±S.D. (n=3). The statistical significance was calculated by the t-test. * p<0.05, ** p<0.01. In the figure, "+30 min chase" means 30 minutes of additional incubation.

FIG. 4-1 shows the results of intracellular uptake of Cy5-PVA and Cy5-PVA-BPA when BCH was not added. The data is shown as mean±S.D. (n=3). The P-value was calculated by the t-test. * p<0.05, ** p<0.01.

FIG. 4-2 shows the results of intracellular uptake of Cy5-PVA and Cy5-PVA-BPA when BCH was added. The data is shown as mean±S.D. (n=3). The P-value was calculated by the t-test. * p<0.05, ** p<0.01.

FIG. 5-1 shows the results of accumulation in tumors of PVA-BPA and Fru-BPA in CT-26 transplanted mice. The data is shown as mean±S.D. (n=4). The P-value was calculated by the t-test. * p<0.05, ** p<0.01.

FIG. 5-2 shows the tumor/blood accumulation ratio of PVA-BPA and Fru-BPA in CT-26 transplanted mice. The data is shown as mean±S.D. (n=4). The P-value was calculated by the t-test. * p<0.05, ** p<0.01.

FIG. 6-1 shows the results of accumulation in tumors of PVA-BPA and Fru-BPA in BxPC3 transplanted mice. The data is shown as mean±S.D. (n=4). The P-value was calculated by the t-test. * p<0.05, ** p<0.01.

FIG. 6-2 shows the tumor/blood accumulation ratio of PVA-BPA and Fru-BPA in BxPC3 transplanted mice. The data is shown as mean±S.D. (n=4). The P-value was calculated by the t-test. * p<0.05, ** p<0.01.

FIG. 8-1 shows the relative change in size of tumors over time after administration of the samples. The data is shown as mean±S.D. (n=4 or 8). The P-value was calculated by Bonferroni's multiple comparison test. * p<0.05, ** p<0.01.

FIG. 8-2 shows Kaplan-Meier curves of relative tumor size after sample administration.

FIG. 9-1 shows images of HE stained tumors after treatment with Control (COLD).

FIG. 9-2 shows images of HE stained tumors after treatment with Control (HOT).

FIG. 9-3 shows images of HE stained tumors 3 hours after treatment with Fru-BPA (HOT).

FIG. 9-4 shows images of HE stained tumors 3 hours after treatment with PVA-BPA (HOT).

FIG. 10-1 shows the $^{19}$F-NMR spectrum of $^{19}$F-BPA.

FIG. 10-2 shows the $^{19}$F-NMR spectrum of Fru-$^{19}$F-BPA.

FIG. 10-3 shows the $^{19}$F-NMR spectrum of PVA-$^{19}$F-BPA.

FIG. 12-1 shows the results of accumulation in tumors of PEG-P[Lys(Fru)/Lys]-BPA.

FIG. 12-2 shows the tumor/blood accumulation ratio of PEG-P[Lys(Fru)/Lys]-BPA.

FIG. 13-1 shows the relative change in size of tumors over time after administration of the samples. The statistically significant difference was calculated by Fisher LSD on the 18th day.

FIG. 13-2 shows the neutron beam irradiation group extracted from FIG. 13-1. The statistically significant difference was calculated by Fisher LSD on the 18th day. In the figure, "Polymer-BPA" refers to PEG-P[Lys(Fru)/Lys]-BPA.

FIG. 14-1 shows the accumulation in tumors of P[Asp(Glucamine)/Asp]-BPA.

FIG. 14-2 shows the tumor/blood accumulation ratio of P[Asp(Glucamine)/Asp]-BPA.

DESCRIPTION OF EMBODIMENTS

Definitions

Figure 1:
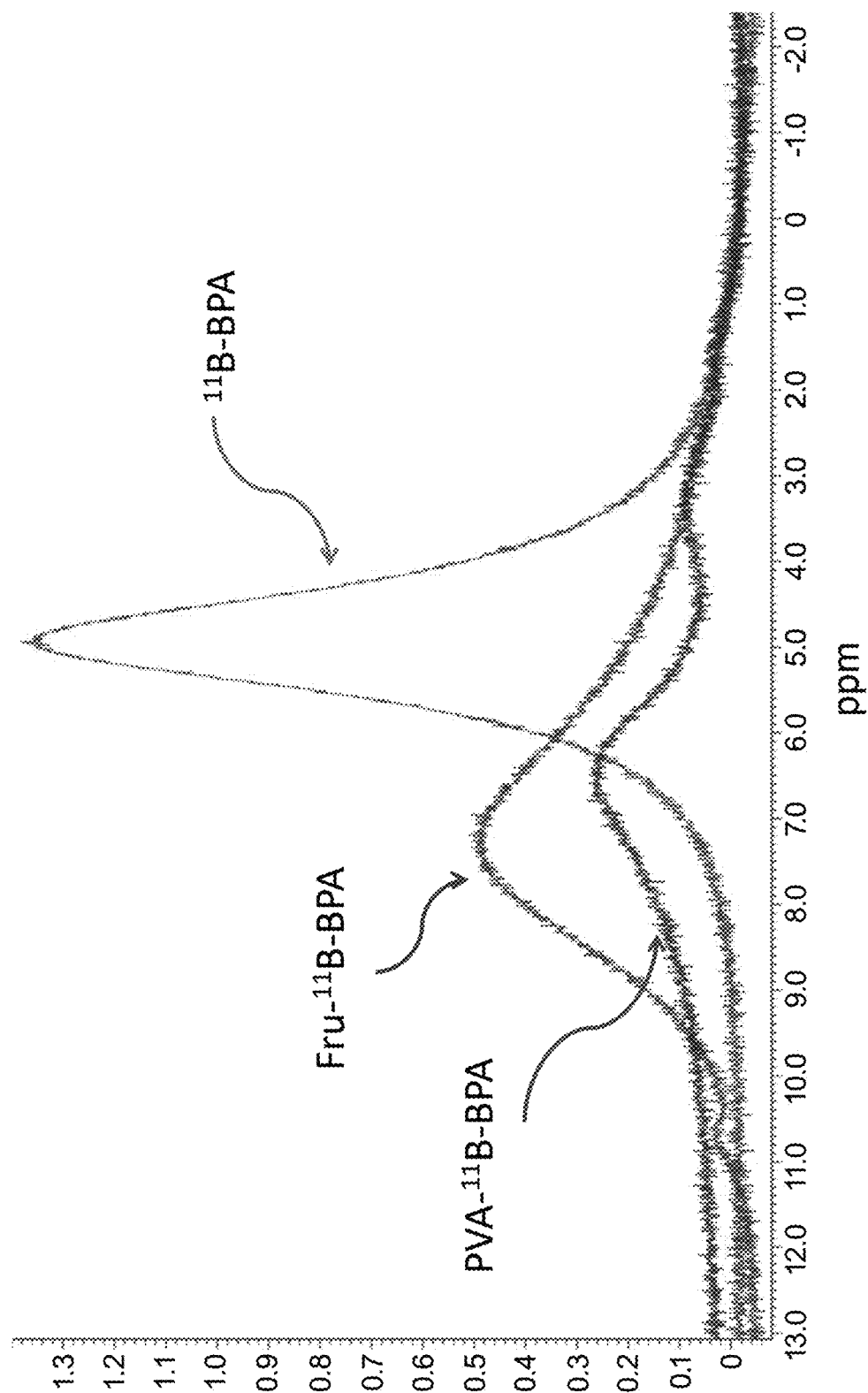
FIG. 1 shows the measurement result of $^{11}$B-NMR (500 MHz, $D_2O$) for $^{11}$B-BPA, Fru-$^{11}$B-BPA and PVA-$^{11}$B-BPA.

Herein "$C_{1-10}$ alkyl group" refers to a linear or branched alkyl group having 1 to 10 carbon atoms. Examples of the $C_{1-10}$ alkyl group include methyl, ethyl, n-propyl, isopropyl, n-butyl, isobutyl, sec-butyl, tert-butyl, n-pentyl, isopentyl, neopentyl, 1-ethylpropyl, n-hexyl, isohexyl, 1,1-dimethylbutyl, 2,2-dimethylbutyl, 3,3-dimethylbutyl, 2-ethylbutyl, n-heptyl, n-octyl, n-nonyl, and n-decyl. $C_{1-10}$ alkyl groups include $C_{1-8}$ alkyl groups, $C_{1-7}$ alkyl groups, Ct-6 alkyl groups, $C_{1-5}$ alkyl groups, and $C_{14}$ alkyl groups.

Herein, "$C_{1-10}$ alkoxy group" refers to a group wherein an oxygen atom is bonded to a $C_{1-10}$ alkyl. Examples of the $C_{1-10}$ alkoxy group include methoxy, ethoxy, propoxy, isopropoxy, butoxy, isobutoxy, sec-butoxy, tert-butoxy, pentyloxy, isopentyloxy, neopentyloxy, 1-ethylpropoxy, hexyloxy, isohexyloxy, 1,1-dimethylbutoxy 2,2-dimethylbutoxy, 3,3-dimethylbutoxy, 2-ethylbutoxy, heptyloxy, octyloxy, nonyloxy, and decyloxy. $C_{1-10}$ alkoxy groups include $C_{1-8}$ alkoxy groups, $C_{1-7}$ alkoxy groups, $C_{1-6}$ alkoxy groups, $C_{1-5}$ alkoxy groups, and $C_{14}$ alkoxy groups.

Herein, "halogen atom" refers to fluorine atoms, chlorine atoms, bromine atoms or iodine atoms.

Herein, "$C_{1-10}$ alkyl group that may be substituted with a halogen" includes "$C_{1-10}$ alkyl groups" wherein the substitutable hydrogen atoms therein are substituted with one or more, for example, one to five halogen atoms. Specific examples include difluoromethyl, trifluoromethyl, 2,2,2-trifluoroethyl, 3,3,3-trifluoropropyl, 4-fluorobutyl, and 4,4,4-trifluorobutyl.

Herein, "$C_{1-10}$ alkoxy group that may be substituted with a halogen" includes "$C_{1-10}$ alkoxy groups" wherein the substitutable hydrogen atoms therein are substituted with one or more, for example, one to five halogen atoms. Specific examples include difluoromethoxy, trifluoromethoxy, 2,2,2-trifluoroethoxy, 3,3,3-trifluoropropoxy, 4-fluorobutoxy, and 4,4,4-trifluorobutoxy.

Herein "$C_{1-40}$ alkylene group" refers to a linear or branched alkyl group having 1 to 40 carbon atoms. Specific examples include a methylene group, ethylene group, propylene group, butylene group, pentylene group, hexylene group, heptylene group, octylene group, nonylene group, decylene group, undecylene group, dodecylene group, tridecylene group, tetradecylene group, pentadecylene group, hexadecylene group, heptadecylene group, octadecylene group, nonadecylene group, icosanylene group, henicosanylene group, docosanylene group, tricosanylene group, tetracosanylene group, pentacosanylene group, hexacosanylene group, heptacosanylene group, octacosanylene group, nonacosanylene group, triacontanylene group, hentriacontanylene, dotriacontanylene group, tritriacontanylene group, tetratriacontanylene group, pentatriacontanylene group, hexatriacontanylene group, heptatriacontanylene group, octatriacontanylene group, nonatriacontanylene group, and tetracontanylene group. $C_{1-40}$ alkylene groups include $C_{1-20}$ alkylene groups, $C_{1-10}$ alkylene groups, and $C_{1-5}$ alkylene groups.

Herein, "$C_{6-14}$ arylene group" refers to a divalent group comprising an aromatic carbocycle having 6 to 14 carbon atoms, for example, a phenylene group, naphthylene group, and anthracenylene group.

Herein, "5- to 10-membered heteroarylene group" refers to a divalent group comprising a 5- to 10-membered aromatic heterocycle. Examples of the aromatic heterocycle include a pyrrole ring, indole ring, thiophene ring, benzothiophene ring, furan ring, benzofuran ring, pyridine ring, quinoline ring, isoquinoline ring, thiazole ring, benzothiazole ring, isothiazole ring, benzisothiazole ring, pyrazole ring, indazole ring, oxazole ring, benzoxazole ring, isoxazole ring, benzisoxazole ring, imidazole ring, benzimidazole ring, triazole ring, benzotriazole ring, pyrimidine ring, uridine ring, pyrazine ring, and pyridazine ring.

Herein, "oxo group" refers to a group that forms a carbonyl group with the carbon atom to which it is bonded.

Herein, "polymer" refers to a compound having at least 2 repeating units, preferably 3 repeating units, more preferably at least 5 repeating units, and even more preferably at least 10 repeating units.

Herein, "pharmaceutically acceptable salt" refers to a salt of a free compound that is pharmaceutically acceptable and has desired pharmacological activities. The "pharmaceutically acceptable salt" is not particularly limited but may be, for example:

a salt of an inorganic acid such as sulfuric acid, hydrochloric acid, hydrobromic acid, phosphoric acid or nitric acid;

a salt of an organic acid such as acetic acid, oxalic acid, lactic acid, tartaric acid, fumaric acid, maleic acid, citric acid, benzenesulfonic acid, methanesulfonic acid, p-toluenesulfonic acid, benzoic acid, camphorsulfonic acid, ethanesulfonic acid, glucoheptonic acid, gluconic acid, glutamic acid, glycolic acid, malic acid, malonic acid, mandelic acid, galactaric acid, or naphthalene-2-sulfonic acid;

a salt of one or a plurality of metal ions such as lithium ions, sodium ions, potassium ions, calcium ions, magnesium ions, zinc ions, aluminum ions; or a salt of an amine such as ammonia, arginine, lysine, piperazine, choline, diethylamine, 4-phenylcyclohexylamine, 2-aminoethanol, or benzathine.

Herein, "tumor" refers to a cell population which exhibits uncontrolled proliferation due to genetic mutation and include benign and malignant tumors. Herein, the term "malignant tumor" can be used interchangeably for the term "cancer". The term "cancer" is used in a broad sense to include cancers which are carcinomas of epithelial origin, sarcomas, and hematological malignancies such as leukemia. Examples of cancers which are carcinomas of epithelial origin include gastric cancer, colon cancer, gallbladder cancer, bile duct cancer, pancreatic cancer, duodenal cancer, kidney cancer, prostate cancer, ovarian cancer, uterine cancer, breast cancer, skin cancer, hepatocellular cancer, tongue cancer, esophageal cancer, and pharyngeal cancer but are not limited thereto. Examples of sarcomas include fibrosarcoma, malignant fibrous histiocytoma, cutaneous fibrosarcoma, liposarcoma, myosarcoma, angiosarcoma, Kaposi's sarcoma, lymphangiosarcoma, synovial sarcoma, and osteosarcoma but are not limited thereto. Examples of hematological malignancies include leukemia, malignant lymphoma, and multiple myeloma but are not limited thereto. Herein, "tumor cells" are cells that form tumors and refer to cells that typically proliferate abnormally independently of normal surrounding tissue (namely cells that have become cancerous).

Herein "subject" refers to any mammal. The "subject" is not particularly limited but includes, for example, humans, primates, mice, rats, dogs, cats, cows, horses, pigs, sheep, goats, and camels. The subject is preferably human.

<<p-Boronophenylalanine (BPA) Derivative>>

The BPA-derivative of the present invention includes a polymer linked directly or via a linker to the BPA-derived group represented by formula (I) below:

[Chem. 15]

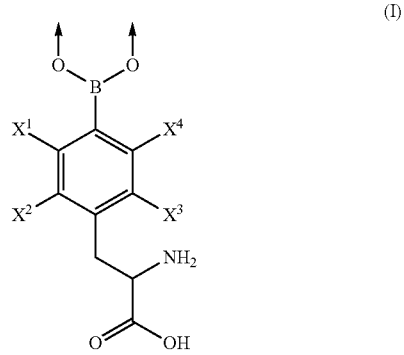

(I)

wherein the arrows indicate a bond with an adjacent atom and $X^1$ to $X^4$ are each independently H, $^{18}F$, or $^{19}F$.

The BPA derivative of the present invention binds to an amino acid transporter (in particular LAT1) on tumor cells via the group represented by formula (I) present on the BPA derivative. After binding to the amino acid transporter, the BPA-derivative of the present invention is taken up into the tumor cell by endocytosis. Thus, the BPA-derivative of the present invention allows the selective accumulation of boron in tumor cells. Further, the BPA-derivative of the present invention is transported to the endosome. As a result, the cell excretion rate of boron from tumor cells is comparatively lower than when BPA is used alone. Thus, boron can be retained for an extended period in tumor cells. In addition, the BPA-derivative of the present invention can achieve an excellent tumor/normal tissue boron concentration ratio and tumor/blood boron concentration ratio.

The three-dimensional structure of the group represented by formula (I) is not particularly limited provided the selective uptake of the BPA-derivative into tumor cells is not obstructed thereby, and the form of the three-dimensional structures may be represented by formula (I-a) or (I-b) below. Further, both the following groups represented by formula (I-a) and (formula I-b) may be incorporated into the BPA-derivative of the present invention. The group in formula (I) is preferably the group represented by formula (I-a) having an L-phenyalanine moiety.

[Chem. 16]

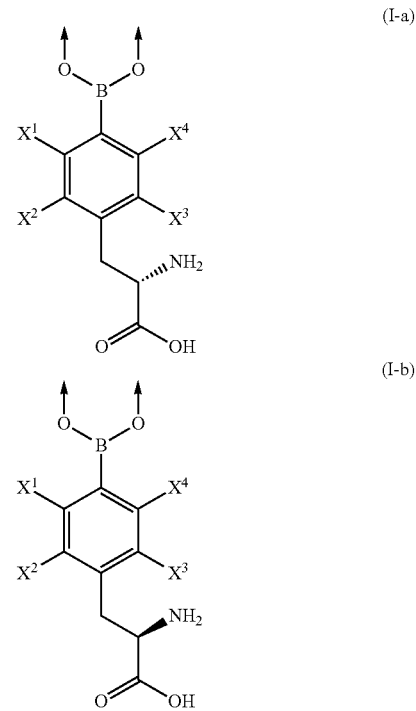

If at least one of the $X^1$ to $X^4$ in formula (I) is $^{18}F$, the BPA-derivative of the present invention can be used for the diagnosis and detection of tumors using, for example, PET (positron emission tomography). If at least one of the $X^1$ to $X^4$ in formula (I) is $^{19}F$, the BPA-derivative of the present invention can be used for the diagnosis and detection of tumors using, for example, $^{19}F$-MRI.

The manner by which the group of formula (I) is linked to the polymer or the linker is not particularly limited. For example, a boronic acid moiety may be reacted with a diol moiety present on the polymer or linker to form the boronic ester structure represented by the following formulas (VIII-a) to (VIIIc).

[Chem. 17]

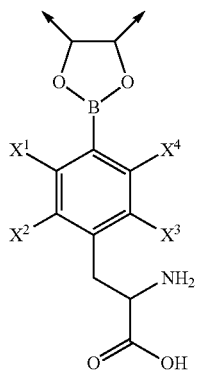
(VIII-a)

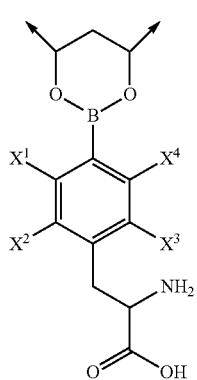
(VIII-b)

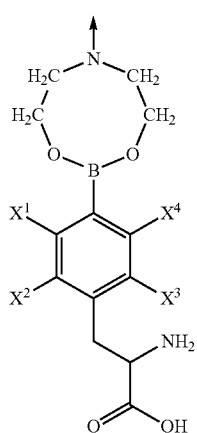
(VIII-c)

wherein
the arrows indicate a bond with an adjacent atom, and
$X^1$ to $X^4$ are each independently H, $^{18}$F, or $^{19}$F.

Further, if an ester structure is formed, such as in the formulas (VIII-a) and (VIII-b) above, this may be reacted with an additional hydroxy group present on the polymer or linker to form a triol borate structure. The triol borate structure is the structure represented by, for example, formula (IV-a) below.

[Chem. 18]

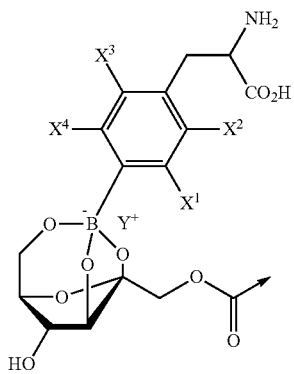
(IV-a)

wherein
the arrow indicates a bond with an adjacent atom,
$X^1$ to $X^4$ are each independently H, $^{18}$F, or $^{19}$F, and
$Y^+$ is, for example, H$^+$, an alkali metal ion, or a tetra-$C_{1-6}$ alkyl-ammonium ion.

Further, if an ester structure is formed such as in formulas (VIII-a) and (VIII-b) above, a boronic ester structure may be formed wherein a hydroxy group is bonded to boron in an aqueous solution. Such boronic ester structures have structures represented by, for example, formulas (IV-b) and (IV-c) below.

[Chem. 19]

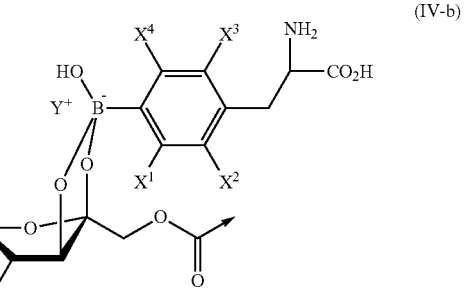
(IV-b)

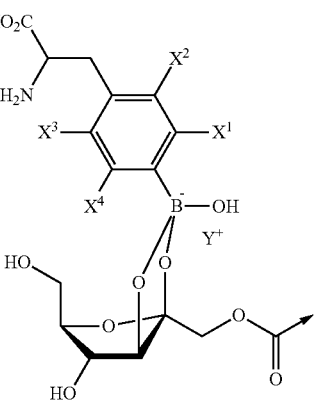
(IV-c)

wherein
the arrows indicate a bond with an adjacent atom,
$X^1$ to $X^4$ are each independently H, $^{18}$F, or $^{19}$F, and
$Y^+$ is, for example, H$^+$, an alkali metal ion, or a tetra-$C_{1-6}$ alkyl-ammonium ion.

Furthermore, for example, a boronic acid moiety may be reacted with a dicarboxylic acid moiety present on the polymer or linker to form a structure such as the one represented by formula (VIII-d) below.

[Chem. 20]

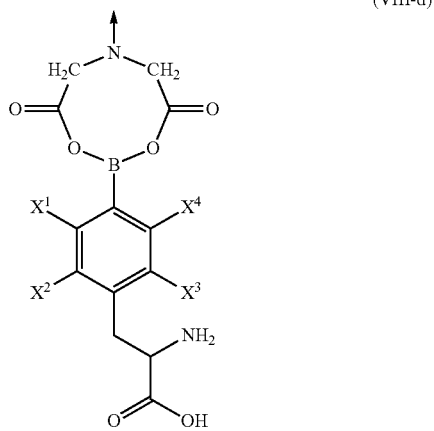

(VIII-d)

wherein
the arrow indicates a bond with an adjacent atom, and
$X^1$ to $X^4$ are each independently H, $^{18}F$, or $^{19}F$.

The number of groups represented by formula (I) in the BPA derivative of the present invention is not particularly limited provided the effect of the BPA derivative is not inhibited. The lower limit of the number of the aforementioned groups is, for example, 1, 2, 3, 4, 5, 10, 15, 20, 25, 30, 35, 40, 45, 50, 60, 70, 80, 90, or 100, and the upper limit of the number of the aforementioned groups is, for example, 200, 300, 400, 500, 600, 700, 800, 900, 1000, 2000, 3000, or 5000. The number of the aforementioned groups is preferably 2 or more. When the number of groups represented by formula (I) in the BPA derivative of the present invention is 2 or more, the groups represented by formula (I) may be the same or different. By forming multiple bonds with a plurality of amino acid transporters (in particular LAT1) on tumor cells via a plurality of the groups represented by formula (I), the binding capacity of the BPA derivative of the present invention to amino acid transporters is significantly increased compared to the binding capacity of a single BPA to an amino acid transporter. More preferably, the number of groups represented by formula (I) is 2 to 5000, 2 to 2000, 2 to 1000, 2 to 500, 2 to 300, 2 to 200, 10 to 5000, 10 to 2000, 10 to 1000, 10 to 500, 10 to 300, or 10 to 200. Note that the reaction between boronic acid and a hydroxy group is an equilibrium reaction. Thus, when the BPA derivative of the present invention has a boronic ester structure, the number of groups represented by formula (I) contained in the BPA derivative of the present invention varies depending on the concentration of boronic acid and polymer in the solution that forms the BPA derivative of the present invention.

The polymer contained in the BPA derivative of the present invention is not particularly limited provided the effect of the BPA derivative is not inhibited. The polymer may be linear or branched and may take the form of a homopolymer or copolymer. In the case of copolymers, the copolymer may be a random copolymer or a block copolymer. The polymer contained in the BPA derivative of the present invention is preferably a water-soluble polymer. Polymers that may be used in the BPA derivative of the present invention include, for example, polyvinyl alcohol, polyurethane, polyester, polyamide, polycarbonate, polyimide, polyether, polyacrylate, polyacrylamide, polysiloxane, polyvinyl, polypeptide, polysaccharide, polynucleotide, and copolymers thereof. Preferably, the polymer is a polyvinyl alcohol, polyester, polyether, polyacrylate, polyacrylamide, polypeptide, polysaccharide, and copolymers thereof. More preferably, the polymer is a polyvinyl alcohol or a polypeptide.

The lower limit of the number average molecular weight of the BPA derivative of the present invention is, for example, 1,000 Da, 2,000 Da, 3,000 Da, 4,000 Da, 5,000 Da, 6,000 Da or 7,000 Da (preferably 5,000 Da), and the upper limit thereof, although not particularly limited, is, for example, 1,500,000 Da, 1,000,000 Da, 500,000 Da, 300,000 Da, 100,000 Da, 70,000 Da or 50,000 Da. The number average molecular weight of the BPA derivative of the present invention is preferably 1,000 Da or more, more preferably 3,000 Da to 150,000 Da, and even more preferably 6,000 Da to 70,000 Da. Herein, unless otherwise specified, the number average molecular weight is a value determined by a calculation based on the integrated value of the $^1$H-NMR spectrum.

When the group represented by formula (I) is linked to the polymer via a linker, the linker contains a group that can bind to BPA. Preferably, the group is a hydroxy group or a carboxyl group. Preferably, the linker contains at least 2 hydroxy groups or at least 2 carboxyl groups. The linker is not particularly limited provided the function of the BPA derivative of the present invention is not inhibited but may be, for example, a $C_{1-40}$ alkylene group substituted with 2 hydroxy groups. Here, the methyl groups in the $C_{1-40}$ alkylene group may be substituted with 1 to 10 oxo groups, the methylene groups in the $C_{1-40}$ alkylene group may be substituted with 1 to 10 halogens, the methylene groups in the $C_{1-40}$ alkylene group may be substituted with 1 to 10 hydroxy groups, adjacent methylene groups may be joined to one another through 1 to 10 unsaturated bonds, and from among the methylene groups in the alkylene group, 1 to 20 methylene groups may be exchanged for NH, N($C_{1-10}$ alkyl), O, S, $C_{6-14}$ arylene, or 5- to 10-membered heteroarylene. Further, the linker includes, for example, polyols (e.g. catechols and polyphenols), sugars (e.g. fructose), sugar alcohols (e.g. sorbitol) and glucamine. Furthermore, the linker includes, for example, the compounds represented by formula (X-a) and formula (XII-a) below.

[Chem. 21]

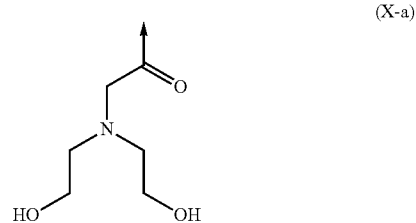

(X-a)

-continued

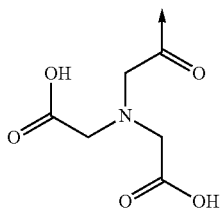
(XII-a)

wherein, the arrows indicate a bond with an adjacent atom.

The BPA derivative of the present invention may contain at least one type of detectable label. Herein, a "detectable label" is any atom or compound that can be detected by any existing detection means. The detection means is not particularly limited but may include, for example, visual inspection, the use of optical inspection equipment (e.g. an optical microscope, fluorescence microscope, phase contrast microscope, in vivo imaging equipment), X-ray equipment (e.g. simple X-ray equipment, CT (computer tomography) equipment), MRI (magnetic resonance imaging) equipment, nuclear medicine examination equipment (e.g. scintigraphy equipment, PET (positron emission tomography) equipment, SPECT (single photon emission computed tomography) equipment), ultrasonic examination equipment and thermography equipment. A person skilled in the art knows the appropriate label for each detection means, as disclosed for example in Lecchi et al., Q J Nucl Med Mol Imaging. 2007; 51 (2): pp. 111-26. The detectable label is not particularly limited but may, for example, include fluorescent labels, luminescent labels, contrast agents, metal atoms, compounds containing one or more metal atoms, radioisotopes, compounds containing one or more radioisotopes, nanoparticles, and liposomes. The position at which the detectable label is introduced into the BPA derivative of the present invention is not particularly limited. For example, the detectable label may be introduced at the terminal groups of the polymer or may be introduced directly or via a linker to a substituent (e.g. a hydroxy group) located within the polymer.

Labels suitable for detection by visual inspection or by using optical inspection equipment include, for example, various fluorescent and luminescent labels. Specific fluorescent labels are not particularly limited but, for example, Cy™ series (e.g. Cy™ 2, 3, 5, 5.5, 7, etc.), DyLight™ series (e.g. DyLight™ 405, 488, 549, 594, 633, 649, 680, 750, 800, etc.), Alexa Fluor® series (e.g. Alexa Fluor® 405, 488, 549, 594, 633, 647, 680, 750, etc.), HiLyte Fluor® series (e.g. HiLyte Fluor™ 488, 555, 647, 680, 750, etc.), ATTO series (e.g. ATTO 488, 550, 633, 647N, 655, 740, etc.), FAM, FITC, Texas Red, GFP, RFP, Qdot, IRDye® (e.g. IRDye® 700DX) may be used.

Further, specific luminescent labels are not particularly limited but, for example, luminol, luciferin, lucigenin, and aequorin may be used.

Labels suitable for detection by using X-ray equipment include, for example, various contrast agents. Specific contrast agents are not particularly limited but, for example iodine atoms, iodine ions, and iodine-containing compounds may be used.

Labels suitable for detection by using MRI equipment include, for example, various metal atoms or compounds containing 1 or more types of metal atom, e.g., a complex containing one or more metal atoms. Specifically, the labels are not particularly limited but may include, for example: gadolinium (III) (Gd (III)), yttrium-88 ($^{88}$Y), indium-111 (111 In); complexes thereof with ligands such as diethylenetriaminepentaacetic acid (DTPA), tetraazacyclododecane-1,4,7,10-tetra acetic acid (DOTA), (1,2-ethanediyldinitrilo) tetraacetic acid (EDTA), ethylenediamine, 2,2'-bipyridine (bipy), 1,10-phenanthroline (phen), 1,2-bis(diphenylphosphino) ethane (DPPE), 2,4-pentanedione (acac), oxalate (ox); and superparamagnetic iron oxide (SPIO), and manganese oxide (MnO).

Examples of labels suitable for detection by using nuclear medicine inspection equipment include, for example, various radioisotopes and compounds containing one or more of the radioisotopes, e.g., a complex of one or more radioisotopes. The radioisotopes are not particularly limited but may include, for example, technetium-99m ($^{99m}$Tc), indium-111 ($^{111}$In) iodine-123 ($^{123}$I), iodine-124 ($^{124}$I), iodine-125 ($^{125}$I), iodine-131 ($^{131}$I), thallium-201 ($^{201}$Tl), carbon-11 ($^{11}$C), nitrogen-13 ($^{13}$C), oxygen-15 ($^{15}$O), fluorine-18 ($^{18}$F), copper-64 ($^{64}$Cu), gallium-67 ($^{67}$Ga), krypton-81m ($^{81m}$Kr), xenon-133 ($^{133}$Xe), strontium-89 ($^{89}$Sr), yttrium-90 ($^{90}$Y). Furthermore, the compounds that contain radioisotopes are not particularly limited but may include, for example, $^{123}$I-IMP, $^{99m}$Tc-HMPAO, $^{99m}$Tc-ECD, $^{99m}$Tc-MDP, $^{99m}$Tc-tetrofosmin, $^{99m}$Tc-MIBI, $^{99m}$TcO$_4$—, $^{99m}$Tc-MAA, $^{99m}$Tc-MAG3, $^{99m}$Tc-DTPA, $^{99m}$Tc-DMSA, $^{18}$F-FDG.

Labels suitable for detection by using ultrasonic examination equipment are not particularly limited but may include, for example, nanoparticles or liposomes.

In one embodiment of the present invention, the BPA derivative of the present invention is a compound represented by formula (II) below or a pharmaceutically acceptable salt thereof.

[Chem. 22]

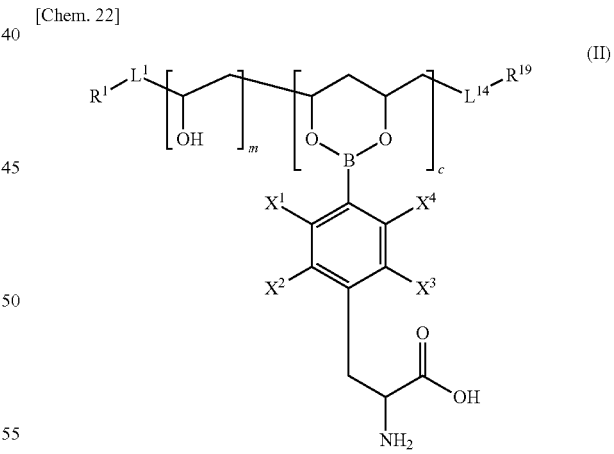

(II)

wherein $X^1$ to $X^4$ are each independently H, $^{18}$F or $^{19}$F, $L^1$ and $L^2$ are each independently a linker or absent, $R^1$ and $R^2$ are each independently hydrogen, a hydroxy group, a carboxyl group, an amino group, a $C_{1-10}$ alkyl group that may be substituted with a halogen, a $C_{1-10}$ alkoxy group that may be substituted with a halogen, a thiol group, a cyano group, an azide group, a —CH(OA$^1$)$_2$ or a detectable label, $A^1$ is a $C_{1-6}$ alkyl group, m=0 to 3,998, n=1 to 2,000, m+2n=10 to 4,000, and the order of the repeating units is arbitrary (i.e., the copolymer may be a random copolymer or a block copolymer).

m and n represent the degree of polymerization. The lower limit of m is 0 but is preferably 0, 1, 2, 3, 4, 5, 6, 7, 8, or 9. The upper limit of m is 3,998 but is preferably 3,998, 3,500, 3,000, 2,500, 2,000, 1,500, 1,000, 900, 800, 700, 600, 500, 400, 300, 200, 100, 50, 40, 30, 20, or 10. The lower limit of n is 1 but is preferably 1, 2, 3, 4, 5, 6, 7, 8, 9, or 10. The upper limit of n is 2,000 but is preferably 2,000, 1,990, 1,980, 1,970, 1,960, 1,950, 1,900, 1,800, 1,700, 1,600, 1,500, 1,400, 1,300, 1,200, 1,100, or 500. The lower limit of (m+2n) is 10 but is preferably 10, 20, 30, 40, or 50. The upper limit of (m+2n) is 4,000 but is preferably 4,000, 3,500, 3,000, 2,500, 2,000, 1,500, 1,000, 900, 800, 700, 600, 500, 400, 300, or 200. m and n can be calculated by quantification based on the integrated value of the $^1$H-NMR spectrum.

$L^1$ and/or $L^2$, when they are linkers, are not particularly limited but may, for example, be a $C_{1-40}$ alkylene group. Here, the methyl groups in the $C_{1-40}$ alkylene group may be substituted with 1 to 10 oxo groups, the methylene groups in the $C_{1-40}$ alkylene group may be substituted with 1 to 10 halogens, adjacent methylene groups may be joined to one another through 1 to 10 unsaturated bonds, and from among the methylene groups in the alkylene group, 1 to 20 methylene groups may be exchanged for NH, N($C_{1-10}$ alkyl), O, S, $C_{6-14}$ arylene, 5- to 10-membered heteroarylene, or polyoxyalkylene having a degree of polymerization of 2 to 2,000, 2 to 1,000, 2 to 500, 2 to 400, 2 to 300, 2 to 200, 2 to 100, 2 to 50, or 2 to 10. The linker may have, for example, the following structure.

[Chem. 23]

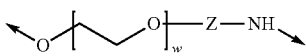

wherein, w is 1 to 2,000 and Z is a $C_{1-5}$ alkylene group.

Further, the linker may have, for example, the following structure.

[Chem. 24]

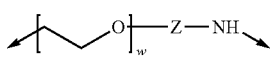

wherein, w is 1 to 2,000 and Z is a $C_{1-5}$ alkylene group.

In one embodiment of the present invention, the BPA derivative of the present invention is a compound represented by formula (III) below or a pharmaceutically acceptable salt thereof.

[Chem. 25]

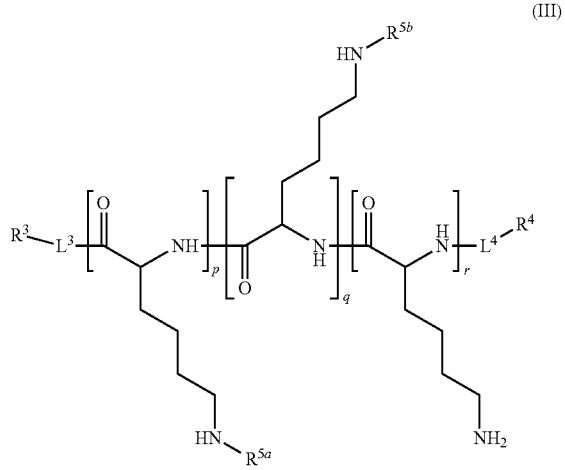

wherein $L^3$ and $L^4$ are each independently a linker or absent, $R^3$ and $R^4$ are each independently hydrogen, a hydroxy group, a carboxyl group, an amino group, a $C_{1-10}$ alkyl group that may be substituted with a halogen, a $C_{1-10}$ alkoxy group that may be substituted with a halogen, a thiol group, a cyano group, an azide group, a —CH(OA$^1$)$_2$ or a detectable label, $A^1$ is a $C_{1-6}$ alkyl group, $R^{5a}$ are each independently a group represented by (IV-a) or (IV-b) below,

[Chem. 26]

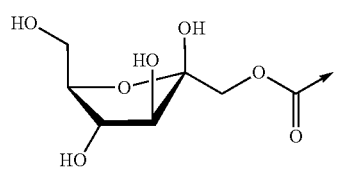

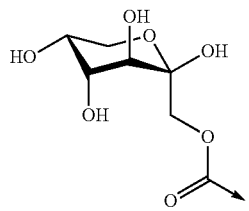

wherein, the arrows indicate a bond with NH, $R^{5b}$ are each independently a group selected from the group consisting of groups represented by formulas (IV-c) to (IV-g) below,

[Chem. 27]

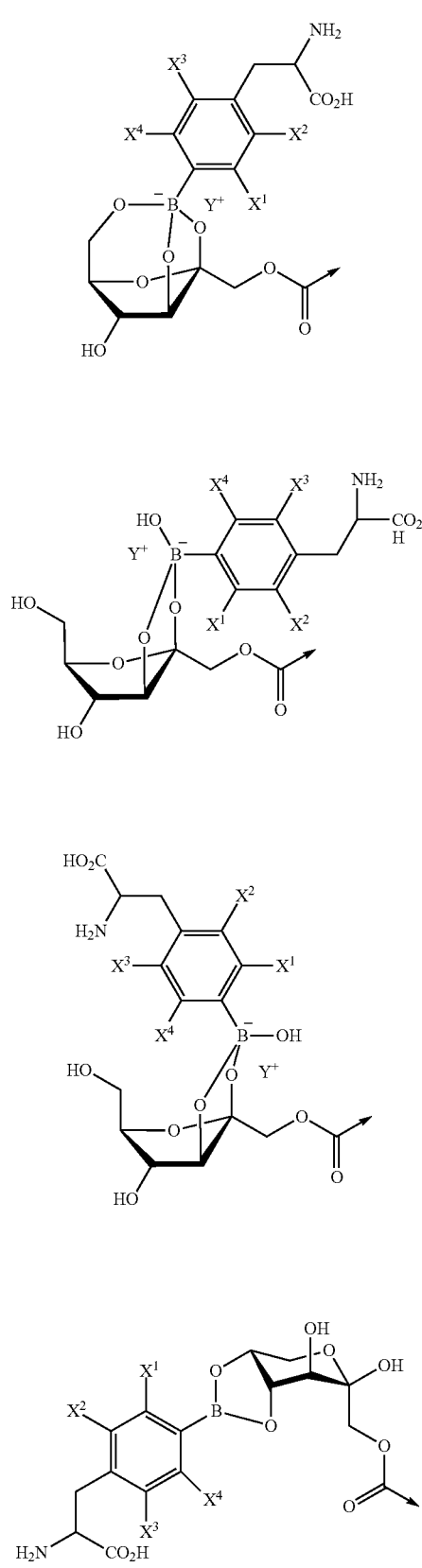

(IV-c)

(IV-d)

(IV-e)

(IV-f)

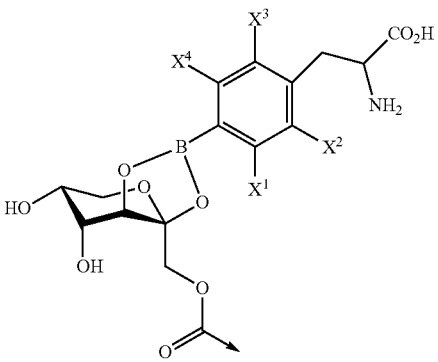

(IV-g)

wherein the arrows indicate a bond with NH, $X^1$ to $X^4$ each independently represent H, $^{18}F$ or $^{19}F$, $Y^+$ represents $H^+$, an alkali metal ion, or a tetra-$C_{1-6}$ alkyl-ammonium ion (for example, tetramethylammonium, tetraethylammonium, tetra-n-propylammonium, tetra-n-butyl ammonium, tetra-n-pentyl ammonium, tetra-n-hexyl ammonium), p=0 to 299, q=1 to 300, r=0 to 299, p+q+r=10 to 300, and the order of the repeating units is arbitrary (i.e., the copolymer may be a random copolymer or a block copolymer).

Herein "$R^{5a}$ are each independently" means that when there is a plurality of repeating units, there is also a plurality of $R^{5a}$ which are in the repeating units, but these $R^{5a}$ may be the same or different from each other. "$R^{5b}$ are each independently" also has the same meaning.

p, q, and r represent the degree of polymerization. The lower limit of p is 0 but is preferably 0, 1, 2, 3, 4, 5, 6, 7, 8, or 9. The upper limit of p is 299 but is preferably 299, 290, 280, 270, 260, or 250. The lower limit of q is 1 but is preferably 1, 2, 3, 4, 5, 6, 7, 8, or 9. The upper limit of q is 300 but is preferably 300, 290, 280, 270, 260, or 250. The lower limit of r is 0 but is preferably 0, 1, 2, 3, 4, 5, 6, 7, 8, or 9. The upper limit of r is 299 but is preferably 299, 290, 280, 270, 260, or 250. The lower limit of (p+q+r) is 10 but is preferably 10, 20, or 30. The upper limit of (p+q+r) is 300 but is preferably 300, 290, 280, 270, 260, or 250. p, q, and r can be calculated by quantification based on the integrated value of the $^1$H-NMR spectrum.

$L^3$ and/or $L^4$, when they are linkers, are not particularly limited but may, for example, be a $C_{1-40}$ alkylene group. Here, the methyl groups in the $C_{1-40}$ alkylene group may be substituted with 1 to 10 oxo groups, the methylene groups in the $C_{1-40}$ alkylene group may be substituted with 1 to 10 halogens, adjacent methylene groups may be joined to one another through 1 to 10 unsaturated bonds, and from among the methylene groups in the alkylene group, 1 to 20 methylene groups may be exchanged for NH, N($C_{1-10}$ alkyl), O, S, $C_{6-14}$ arylene, 5- to 10-membered heteroarylene, or polyoxyalkylene having a degree of polymerization of 2 to 2,000, 2 to 1,000, 2 to 500, 2 to 400, 2 to 300, 2 to 200, 2 to 100, 2 to 50, or 2 to 10. The linker may have, for example, the following structure,

[Chem. 28]

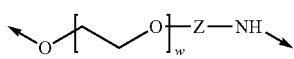

wherein, w is 1 to 2,000 and Z is a $C_{1-5}$ alkylene group.

Further, the linker may have, for example, the following structure,

[Chem. 29]

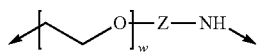

wherein, w is 1 to 2,000 and Z is a $C_{1-5}$ alkylene group.

In one embodiment of the present invention, the BPA derivative of the present invention is a compound represented by formula (V) below or a pharmaceutically acceptable salt thereof,

[Chem. 30]

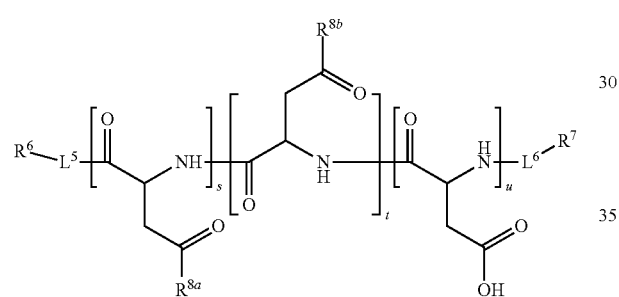

(V)

wherein $L^5$ and $L^6$ are each independently a linker or absent, $R^6$ and $R^7$ are each independently hydrogen, a hydroxy group, a carboxyl group, an amino group, a $C_{1-10}$ alkyl group that may be substituted with a halogen, a $C_{1-10}$ alkoxy group that may be substituted with a halogen, a thiol group, a cyano group, an azide group, —$CH(OA^1)_2$ or a detectable label, $A^1$ is a $C_{1-6}$ alkyl group, $R^{8a}$ are each independently a group represented by (VI-a) below,

[Chem. 31]

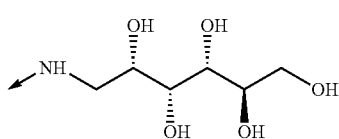

(VI-a)

wherein, the arrow indicates a bond with a carbonyl carbon, $R^{8b}$ are each independently a group selected from the group consisting of the groups represented by formulas (VI-b) to (VI-h) below,

[Chem. 32]

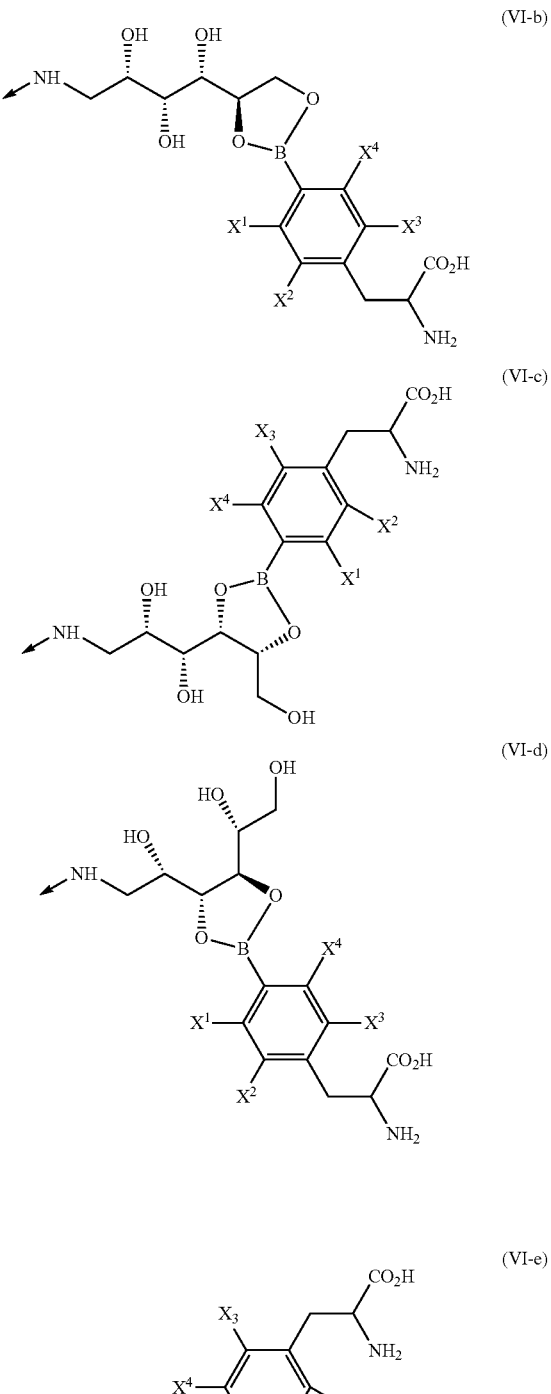

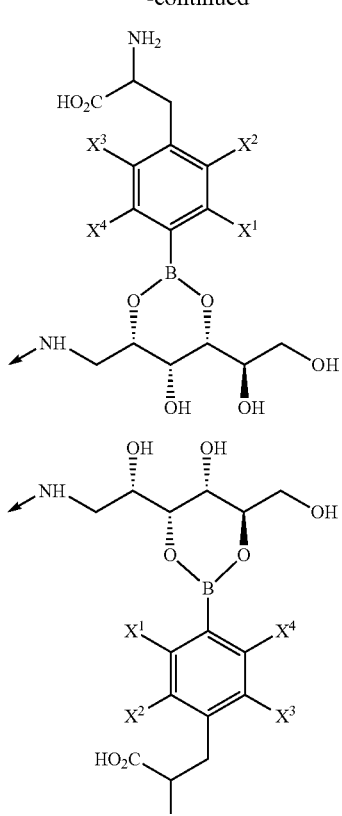

wherein
the arrows indicate a bond with a carbonyl carbon,
$X^1$ to $X^4$ are each independently H, $^{18}F$, or $^{19}F$,
s=0 to 299,
t=1 to 300,
u=0 to 299,
s+t+u=2 to 300, and
the order of the repeating units is arbitrary (i.e., the copolymer may be a random copolymer or a block copolymer).

Herein "$R^{8b}$ are each independently" means that when there is a plurality of repeating units, there is also a plurality of $R^{8b}$ which are in the repeating units, but these $R^{8b}$ may be the same or different from each other.

s, t, and u represent the degree of polymerization. The lower limit of s is 0 but is preferably 0, 1, 2, 3, 4, 5, 6, 7, 8, or 9. The upper limit of s is 299 but is preferably 299, 290, 280, 270, 260, or 250. The lower limit of t is 1 but is preferably 1, 2, 3, 4, 5, 6, 7, 8, or 9. The upper limit of t is 300 but is preferably 300, 290, 280, 270, 260, or 250. The lower limit of u is 0 but is preferably 0, 1, 2, 3, 4, 5, 6, 7, 8, or 9. The upper limit of u is 299 but is preferably 299, 290, 280, 270, 260, or 250. The lower limit of (s+t+u) is 2 but is preferably 2, 3, 4, or 5. The upper limit of (s+t+u) is 300 but is preferably 300, 290, 280, 270, 260, or 250. s, t, and u can be calculated by quantification based on the integrated value of the $^1H$-NMR spectrum.

$L^5$ and/or $L^6$, when they are linkers, are not particularly limited but may, for example, be a $C_{1-40}$ alkylene group. Here, the methyl groups in the $C_{1-40}$ alkylene group may be substituted with 1 to 10 oxo groups, the methylene groups in the $C_{1-40}$ alkylene group may be substituted with 1 to 10 halogens, adjacent methylene groups may be joined to one another through 1 to 10 unsaturated bonds, and from among the methylene groups in the alkylene group, 1 to 20 methylene groups may be exchanged for NH, N($C_{1-10}$ alkyl), O, S, $C_{6-14}$ arylene, 5- to 10-membered heteroarylene, or polyoxyalkylene having a degree of polymerization of 50 to 500. The linker may have, for example, the following structure,

[Chem. 33]

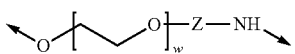

wherein, w is 1 to 2,000 and Z is a $C_{1-5}$ alkylene group.

Further, the linker may have, for example, the following structure,

[Chem. 34]

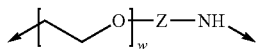

wherein, w is 1 to 2,000 and Z is a $C_{1-5}$ alkylene group.

In one embodiment of the present invention, the BPA derivative of the present invention is a compound represented by formula (IX) below or a pharmaceutically acceptable salt thereof.

[Chem. 35]

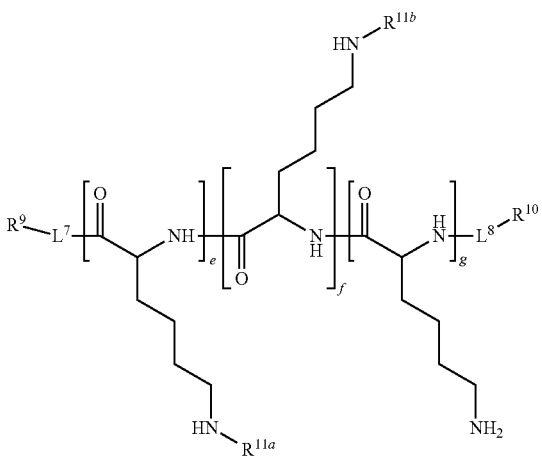

(IX)

wherein

L$^7$ and L$^8$ are each independently a linker or absent,

R$^9$ and R$^{10}$ are each independently hydrogen, a hydroxy group, a carboxyl group, an amino group, a C$_{1-10}$ alkyl group that may be substituted with a halogen, a C$_{1-10}$ alkoxy group that may be substituted with a halogen, a thiol group, a cyano group, an azide group, a —CH(OA$^1$)$_2$ or a detectable label, A$^1$ is a C$_{1-6}$ alkyl group, R$^{11a}$ is represented by formula (X-a) below,

[Chem. 36]

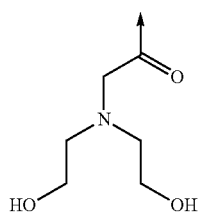

(X-a)

wherein, the arrow indicates a bond with NH,

R$^{11b}$ are each independently a group represented by formula (X-b) below,

[Chem. 37]

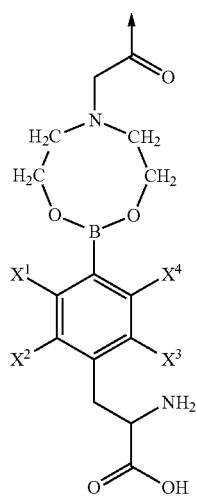

(X-b)

wherein the arrow indicates a bond with NH,

X$^1$ to X$^4$ each independently represent H, $^{18}$F or $^{19}$F,

Y$^+$ represents H$^+$, an alkali metal ion, or a tetra-C$_{1-6}$ alkyl-ammonium ion (for example, tetramethylammonium, tetraethylammonium, tetra-n-propylammonium, tetra-n-butyl ammonium, tetra-n-pentyl ammonium, tetra-n-hexyl ammonium), e=0 to 299, f=1 to 300, g=0 to 299, e+f+g=10 to 300, and the order of the repeating units is arbitrary (i.e., the copolymer may be a random copolymer or a block copolymer).

Herein "R$^{11b}$ are each independently" means that when there is a plurality of repeating units, there is also a plurality of R$^{11b}$ which are in the repeating units, but these R$^{11b}$ may be the same or different from each other.

e, f, and g represent the degree of polymerization. The lower limit of e is 0 but is preferably 0, 1, 2, 3, 4, 5, 6, 7, 8, or 9. The upper limit of e is 299 but is preferably 299, 290, 280, 270, 260, or 250. The lower limit of f is 1 but is preferably 1, 2, 3, 4, 5, 6, 7, 8, or 9. The upper limit of f is 300 but is preferably 300, 290, 280, 270, 260, or 250. The lower limit of g is 0 but is preferably 0, 1, 2, 3, 4, 5, 6, 7, 8, or 9. The upper limit of g is 299 but is preferably 299, 290, 280, 270, 260, or 250. The lower limit of (e+f+g) is 10 but is preferably 10, 20, or 30. The lower limit of (e+f+g) is 300 but is preferably 300, 290, 280, 270, 260, or 250. e, f, and g can be calculated by quantification based on the integrated value of the $^1$H-NMR spectrum.

L$^7$ and/or L$^8$, when they are linkers, are not particularly limited but may, for example, be a C$_{1-40}$ alkylene group. Here, the methyl groups in the C$_{1-40}$ alkylene group may be substituted with 1 to 10 oxo groups, the methylene groups in the C$_{1-40}$ alkylene group may be substituted with 1 to 10 halogens, adjacent methylene groups may be joined to one another through 1 to 10 unsaturated bonds, and from among the methylene groups in the alkylene group, 1 to 20 methylene groups may be exchanged for NH, N(C$_{1-10}$ alkyl), O, S, C$_{6-14}$ arylene, 5- to 10-membered heteroarylene, or polyoxyalkylene having a degree of polymerization of 2 to 2,000, 2 to 1,000, 2 to 500, 2 to 400, 2 to 300, 2 to 200, 2 to 100, 2 to 50, or 2 to 10. The linker may have, for example, the following structure.

[Chem. 38]

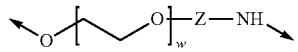

wherein, w is 1 to 2,000 and Z is a C$_{1-5}$ alkylene group.

Further, the linker may have, for example, the following structure,

[Chem. 39]

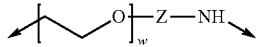

wherein, w is 1 to 2,000 and Z is a C$_{1-5}$ alkylene group.

In one embodiment of the present invention, the BPA derivative of the present invention is a compound represented by formula (XI) below or a pharmaceutically acceptable salt thereof,

[Chem. 40]

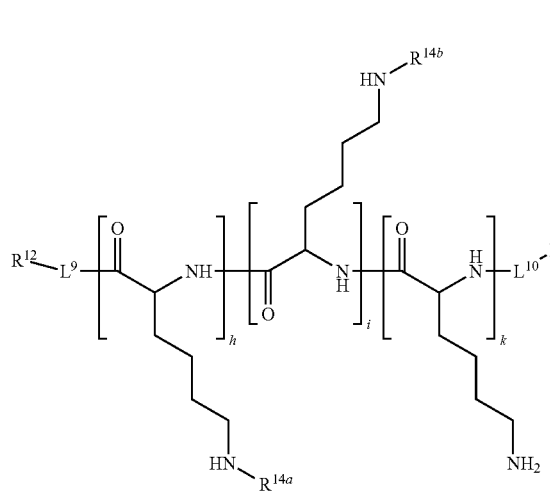

(XI)

wherein $L^9$ and $L^{10}$ are each independently a linker or absent, $R^{12}$ and $R^{13}$ are each independently hydrogen, a hydroxy group, a carboxyl group, an amino group, a $C_{1-10}$ alkyl group that may be substituted with a halogen, a $C_{1-10}$ alkoxy group that may be substituted with a halogen, a thiol group, a cyano group, an azide group, a —CH(OA$^1$)$_2$ or a detectable label, $A^1$ is a $C_{1-6}$ alkyl group, $R^{14a}$ is represented by the formula (XII-a) below,

[Chem. 41]

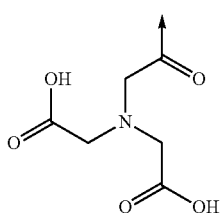

(XII-a)

wherein, the arrow indicates a bond with NH, $R^{14b}$ are each independently represented by the formula (XII-b) below,

[Chem. 42]

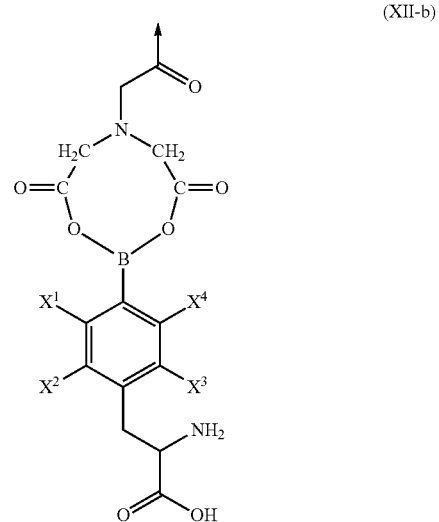

(XII-b)

wherein the arrow indicates a bond with NH, $X^1$ to $X^4$ each independently represent H, $^{18}F$ or $^{19}F$, $Y^+$ represents H$^+$, an alkali metal ion, or a tetra-$C_{1-6}$ alkyl-ammonium ion (for example, tetramethylammonium, tetraethylammonium, tetra-n-propylammonium, tetra-n-butyl ammonium, tetra-n-pentyl ammonium, tetra-n-hexyl ammonium), h=0 to 299, i=1 to 300, k=0 to 299, h+i+k=10 to 300, and the order of the repeating units is arbitrary (i.e., the copolymer may be a random copolymer or a block copolymer).

Herein "$R^{14b}$ are each independently" means that when there is a plurality of repeating units, there is also a plurality of $R^{14b}$ which are in the repeating units, but these $R^{14b}$ may be the same or different from each other.

h, i, and k represent the degree of polymerization. The lower limit of h is 0 but is preferably 0, 1, 2, 3, 4, 5, 6, 7, 8, or 9. The upper limit of h is 299 but is preferably 299, 290, 280, 270, 260, or 250. The lower limit of i is 1 but is preferably 1, 2, 3, 4, 5, 6, 7, 8, or 9. The upper limit of i is 300 but is preferably 300, 290, 280, 270, 260, or 250. The lower limit of k is 0 but is preferably 0, 1, 2, 3, 4, 5, 6, 7, 8, or 9. The upper limit of k is 299 but is preferably 299, 290, 280, 270, 260, or 250. The lower limit of (h+i+k) is 10 but is preferably 10, 20, or 30. The lower limit of (h+i+k) is 300 but is preferably 300, 290, 280, 270, 260, or 250. h, i, and k can be calculated by quantification based on the integrated value of the $^1$H-NMR spectrum.

$L^9$ and/or $L^{10}$, when they are linkers, are not particularly limited but may, for example, be a $C_{1-40}$ alkylene group. Here, the methyl groups in the $C_{1-40}$ alkylene group may be substituted with 1 to 10 oxo groups, the methylene groups in the $C_{1-40}$ alkylene group may be substituted with 1 to 10 halogens, adjacent methylene groups may be joined to one another through 1 to 10 unsaturated bonds, and from among the methylene groups in the alkylene group, 1 to 20 methylene groups may be exchanged for NH, N($C_{1-10}$ alkyl), O, S, $C_{6-14}$ arylene, 5- to 10-membered heteroarylene, or polyoxyalkylene having a degree of polymerization of 2 to 2,000, 2 to 1,000, 2 to 500, 2 to 400, 2 to 300, 2 to 200, 2 to 100, 2 to 50, or 2 to 10. The linker may have, for example, the following structure,

[Chem. 43]

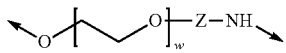

wherein, w is 1 to 2,000 and Z is a $C_{1-5}$ alkylene group.

Further, the linker may have, for example, the following structure,

[Chem. 44]

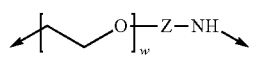

wherein, w is 1 to 2,000 and Z is a $C_{1-5}$ alkylene group.

In one embodiment of the present invention, the BPA derivative of the present invention is a compound represented by formula (XX) below or a pharmaceutically acceptable salt thereof,

[Chem. 45]

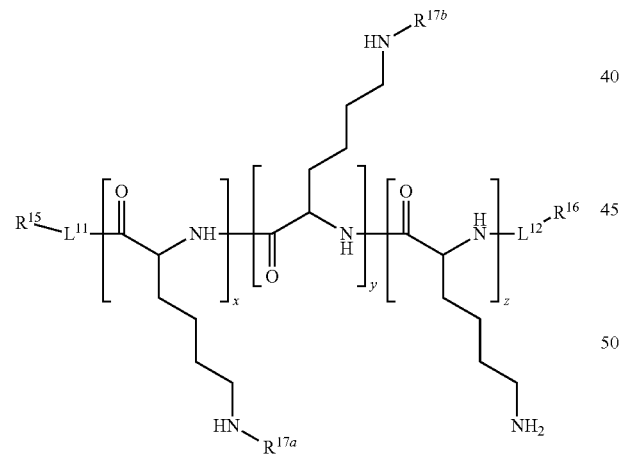

(XX)

wherein $L^{11}$ and $L^{12}$ are each independently a linker or absent, $R^{15}$ and $R^{16}$ are each independently hydrogen, a hydroxy group, a carboxyl group, an amino group, a $C_{1-10}$ alkyl group that may be substituted with a halogen, a $C_{1-10}$ alkoxy group that may be substituted with a halogen, a thiol group, a cyano group, an azide group, a —$CH(OA^1)_2$ or a detectable label, $A^1$ is a $C_{1-6}$ alkyl group, $R^{17a}$ is a group represented by formula (XXI-a) below,

[Chem. 46]

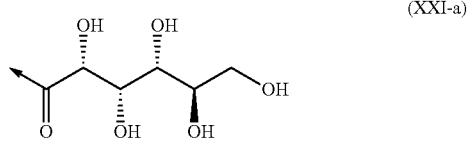

(XXI-a)

wherein, the arrow indicates a bond with NH, $R^{17b}$ are each independently a group selected from the group consisting of the groups represented by formulas (XXI-b) to (XXI-h) below,

[Chem. 47]

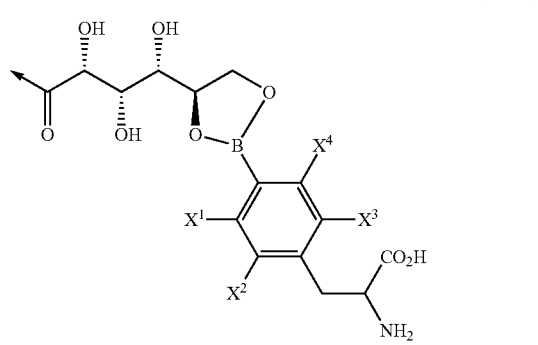

(XXI-b)

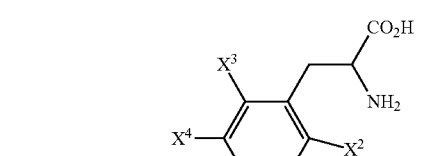

(XXI-c)

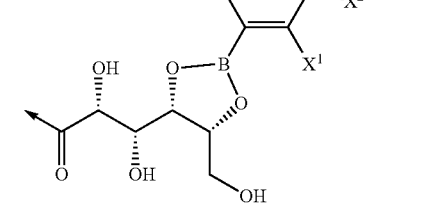

(XXI-d)

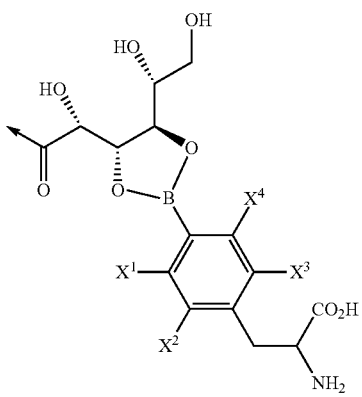

-continued (XXI-e)
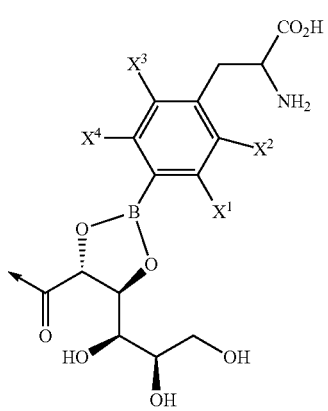

(XXI-f)
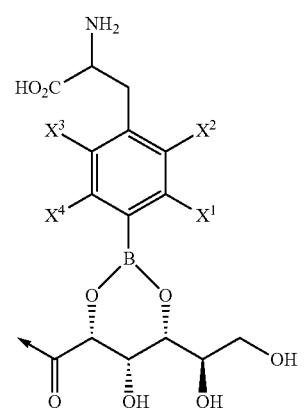

(XXI-g)
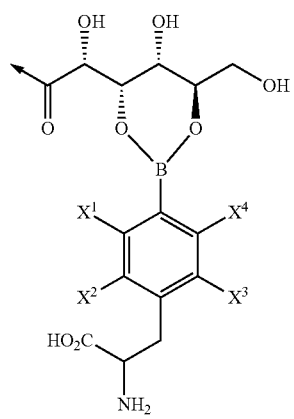

(XXI-h)
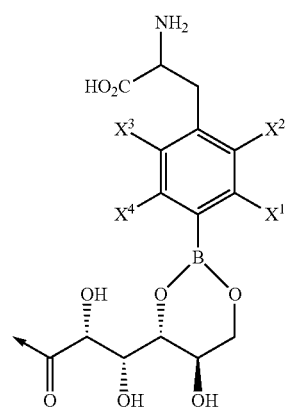

wherein the arrows indicate a bond with NH, $X^1$ to $X^4$ are each independently H, $^{18}F$, or $^{19}F$, x=0 to 299, y=1 to 300, z=0 to 299, x+y+z=10 to 300, and the order of the repeating units is arbitrary (i.e., the copolymer may be a random copolymer or a block copolymer).

Herein "$R^{17b}$ are each independently" means that when there is a plurality of repeating units, there is also a plurality of $R^{17b}$ which are in the repeating units, but these $R^{17b}$ may be the same or different from each other.

x, y, and z represent the degree of polymerization. The lower limit of x is 0 but is preferably 0, 1, 2, 3, 4, 5, 6, 7, 8, or 9. The upper limit of x is 299 but is preferably 299, 290, 280, 270, 260, or 250. The lower limit of y is 1 but is preferably 1, 2, 3, 4, 5, 6, 7, 8, or 9. The upper limit of y is 300 but is preferably 300, 290, 280, 270, 260, or 250. The lower limit of z is 0 but is preferably 0, 1, 2, 3, 4, 5, 6, 7, 8, or 9. The upper limit of z is 299 but is preferably 299, 290, 280, 270, 260, or 250. The lower limit of (x+y+z) is 10 but is preferably 10, 20, or 30. The lower limit of (x+y+z) is 300 but is preferably 300, 290, 280, 270, 260, or 250. x, y, and z can be calculated by quantification based on the integrated value of the $^1$H-NMR spectrum.

$L^{11}$ and/or $L^{12}$, when they are linkers, are not particularly limited but may, for example, be a $C_{1-40}$ alkylene group. Here, the methyl groups in the $C_{1-40}$ alkylene group may be substituted with 1 to 10 oxo groups, the methylene groups in the $C_{1-40}$ alkylene group may be substituted with 1 to 10 halogens, adjacent methylene groups may be joined to one another through 1 to 10 unsaturated bonds, and from among the methylene groups in the alkylene group, 1 to 20 methylene groups may be exchanged for NH, N($C_{1-10}$ alkyl), O, S, a $C_{6-14}$ arylene, 5- to 10-membered heteroarylene, or a polyoxyalkylene having a degree of polymerization of 2 to 1,000, 2 to 500, 2 to 400, 2 to 300, 2 to 200, 2 to 100, 2 to 50, or 2 to 10. The linker may have, for example, the following structure,

[Chem. 48]

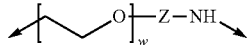

wherein, w is 1 to 2,000 and Z is a $C_{1-5}$ alkylene group.

In one embodiment of the present invention, the BPA derivative of the present invention is a compound represented by formula (XXII) below or a pharmaceutically acceptable salt thereof

[Chem. 49]

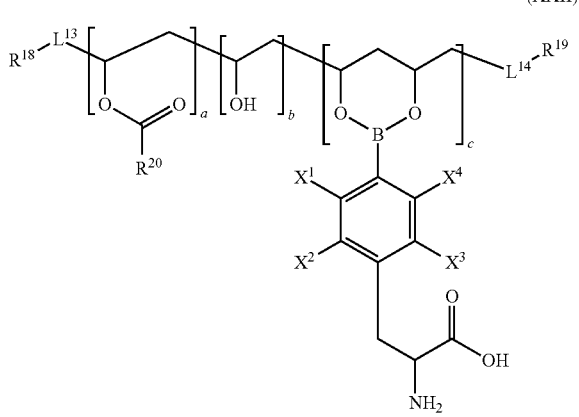

(XXII)

wherein $X^1$ to $X^4$ are each independently H, $^{18}$F or $^{19}$F, $L^{13}$ and $L^{14}$ are each independently a linker or absent, $R^{18}$ and $R^{19}$ are each independently hydrogen, a hydroxy group, a carboxyl group, an amino group, a $C_{1-10}$ alkyl group that may be substituted with a halogen, a $C_{1-10}$ alkoxy group that may be substituted with a halogen, a thiol group, a cyano group, an azide group, —CH(OA$^1$)$_2$ or a detectable label, $A^1$ is a $C_{1-6}$ alkyl group, $R^{20}$ are each independently a $C_{1-10}$ alkyl group that may be substituted with a halogen, an —NR$^{21}$R$^{22}$ group, or the following group,

[Chem. 50]

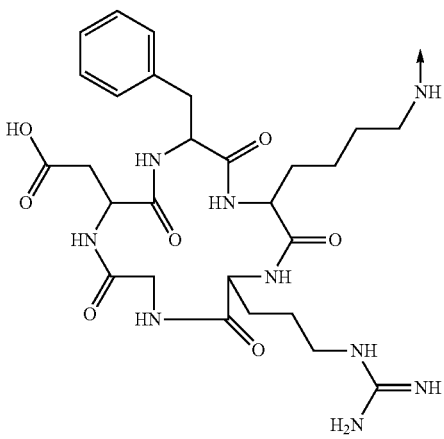

wherein, the arrow indicates a bond with a carbonyl carbon, $R^{21}$ and $R^{22}$ are each independently a hydrogen or a $C_{1-10}$ alkyl group that may be substituted with a halogen, a=1 to 3,998,
b=0 to 3,997,
c=1 to 2,000,
a+b+2c=10 to 4,000, and the order of the repeating units is arbitrary.

a, b, and c represent the degree of polymerization. The lower limit of a is 1 but is preferably 1, 2, 3, 4, 5, 6, 7, 8, or 9. The upper limit of a is 3,998 but is preferably 3,998, 3,500, 3,000, 2,500, 2,000, 1,500, 1,000, 900, 800, 700, 600, 500, 400, 300, 200, 100, 50, 40, 30, 20, or 10. The lower limit of b is 0 but is preferably 0, 1, 2, 3, 4, 5, 6, 7, 8, or 9. The upper limit of b is 3,997 but is preferably 3,997, 3,500, 3,000, 2,500, 2,000, 1,500, 1,000, 900, 800, 700, 600, 500, 400, 300, 200, 100, 50, 40, 30, 20, or 10. The lower limit of c is 1 but is preferably 1, 2, 3, 4, 5, 6, 7, 8, 9, or 10. The upper limit of c is 2,000 but is preferably 2,000, 1,990, 1,980, 1,970, 1,960, 1,950, 1,900, 1,800, 1,700, 1,600, 1,500, 1,400, 1,300, 1,200, 1,100, or 500. The lower limit of (a+b+2c) is 10 but is preferably 10, 20, 30, 40, or 50. The upper limit of (a+b+2c) is 4,000 but is preferably 4,000, 3,500, 3,000, 2,500, 2,000, 1,500, 1,000, 900, 800, 700, 600, 500, 400, 300, or 200. a, b, and c can be calculated by quantification based on the integrated value of the $^1$H-NMR spectrum.

$L^{13}$ and/or $L^{14}$, when they are linkers, are not particularly limited but may, for example, be a $C_{1-40}$ alkylene group. Here, the methyl groups in the $C_{1-40}$ alkylene group may be substituted with 1 to 10 oxo groups, the methylene groups in the $C_{1-40}$ alkylene group may be substituted with 1 to 10 halogens, adjacent methylene groups may be joined to one another through 1 to 10 unsaturated bonds, and from among the methylene groups in the alkylene group, 1 to 20 methylene groups may be exchanged for NH, N($C_{1-10}$ alkyl), O, S, a $C_{6-14}$ arylene, 5- to 10-membered heteroarylene, or polyoxyalkylene having a degree of polymerization of 2 to 2,000, 2 to 1,000, 2 to 500, 2 to 400, 2 to 300, 2 to 200, 2 to 100, 2 to 50, or 2 to 10. The linker may have, for example, the following structure,

[Chem. 51]

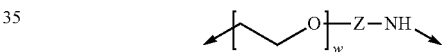

wherein, w is 1 to 2,000 and Z is a $C_{1-5}$ alkylene group.

The BPA derivative of the present invention can be produced by introducing the group represented by formula (I) to a polymer applying any of various publicly known methods. For example, the compound represented by formula (VII) below

[Chem. 52]

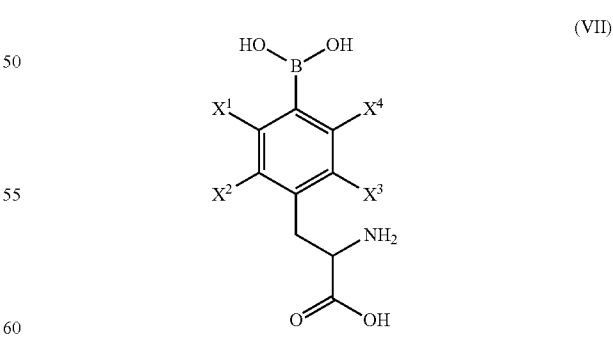

(VII)

wherein $X^1$ to $X^4$ are each independently H, $^{18}$F, or $^{19}$F, and a polymer that, when reacted with the compound represented by formula (VII), can form the group represented by formula (I) below

[Chem. 53]

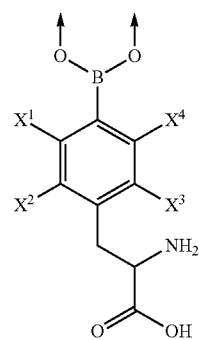

(I)

wherein, the arrows indicate a bond with an adjacent atom, and $X^1$ to $X^4$ are each independently H, $^{18}$F, or $^{19}$F, are mixed in water or a water-containing solvent (for example, a phosphate buffered saline) and reacted, for example, at 4 to 100° C. for 10 minutes to 1 hour to produce the BPA derivative.

<<Composition>>

The composition of the present invention comprises the BPA derivative of the present invention. The composition of the present invention may further comprise pharmaceutically acceptable carriers, diluents, buffers, excipients and combinations thereof. The composition of the present invention may be used to treat, diagnose, and detect tumors. When the composition of the present invention is administered into a subject, the route of administration is not particularly limited but may include intravenous, subcutaneous, intramuscular, intra-articular, intraperitoneal, and intraocular administration. Further, the dosage is appropriately selected depending on the type of illness and the age, weight, and sex of the subject.

<<Kit>>

The kit of the present invention comprises a compound represented by formula (VII) below,

[Chem. 54]

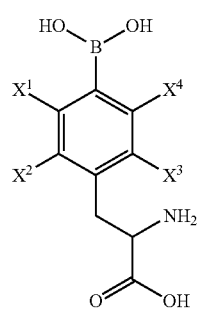

(VII)

wherein $X^1$ to $X^4$ are each independently H, $^{18}$F, or $^{19}$F, and a polymer that, when reacted with the compound represented by formula (VII), can form the group represented by formula (I) below

[Chem. 55]

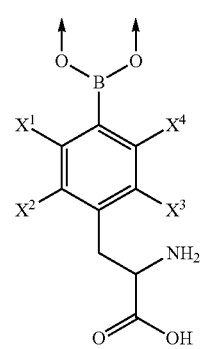

(I)

wherein, the arrows indicate a bond with an adjacent atom, and $X^1$ to $X^4$ are each independently H, $^{18}$F, or $^{19}$F.

The polymer that can form the group represented by formula (I) through a reaction with the compound represented by formula (VII) may be linear or branched and may take the form of a homopolymer or copolymer. In the case of copolymers, the copolymer may be a random copolymer or a block copolymer. The polymer is preferably a water-soluble polymer. The polymer may comprise, for example, polyvinyl alcohol, polyurethane, polyester, polyamide, polycarbonate, polyimide, polyether, polyacrylate, polyacrylamide, polysiloxane, polyvinyl, polypeptide, polysaccharide, polynucleotide, and copolymers thereof. Preferably, the polymer contains a polyvinyl alcohol, polyester, polyether, polyacrylate, polyacrylamide, polypeptide, polysaccharide, or copolymers thereof, and more preferably, the polymer contains polyvinyl alcohol or polypeptide. The polymer that can form the group represented by formula (I) through a reaction with the compound represented by formula (VII) may have a moiety that forms the group represented by formula (I) when reacted with the compound represented by formula (VII) linked to a side chain. This moiety can constitute a linker between the polymer and the group represented by formula (I).

The polymer that can form the group represented by formula (I) through a reaction with the compound represented by formula (VII) may be represented by formulas (XV-a) to (XV-g) below. The definition of the symbols in the formulas and the ranges thereof are as described above.

[Chem. 56]

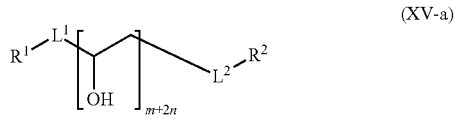

(XV-a)

[Chem. 57]

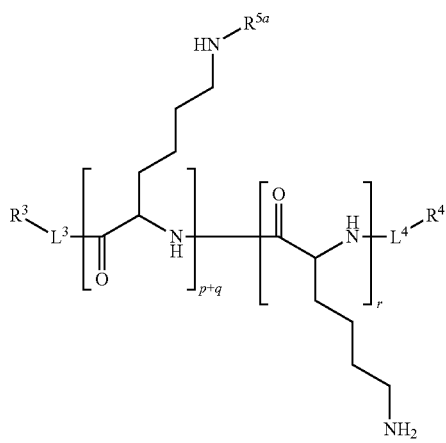

(XV-b)

[Chem. 58]

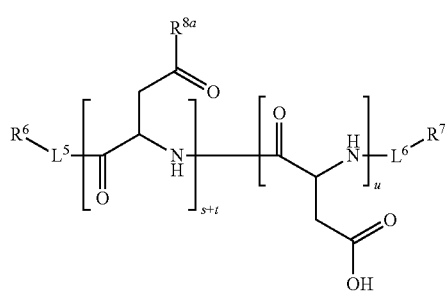

(XV-c)

[Chem. 59]

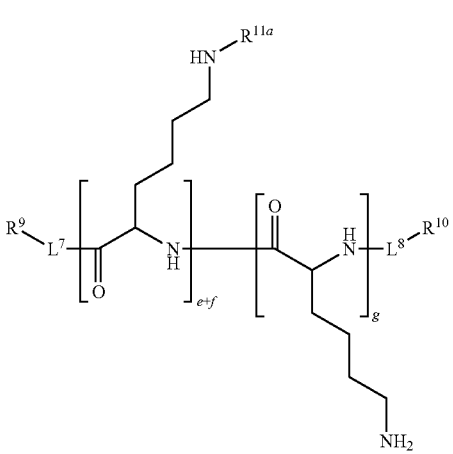

(XV-d)

[Chem. 60]

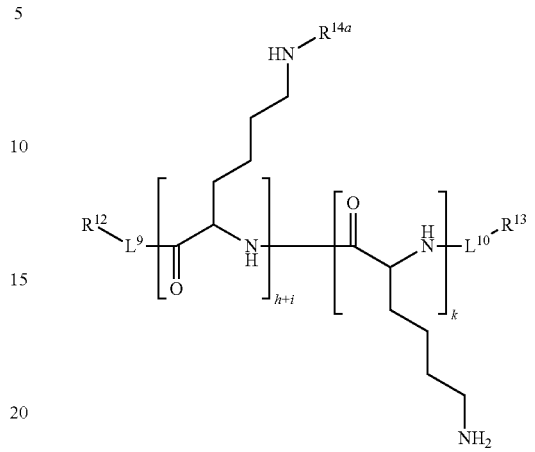

(XV-e)

[Chem. 61]

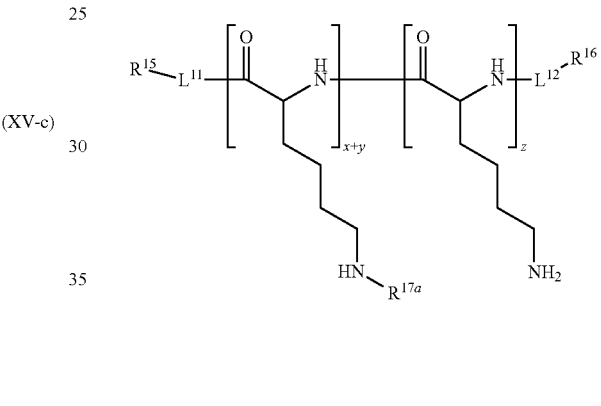

(XV-f)

[Chem. 62]

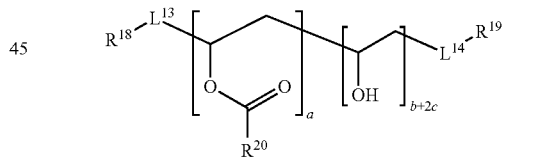

(XV-g)

The kit of the present invention may include instructions on the method of producing the BPA derivative of the present invention. The kit may also include instructions on the method of using the BPA derivative of the present invention to treat, diagnose, and detect tumors.

All documents mentioned in this specification are incorporated herein by reference in their entirety.

The embodiments of the present invention described below are merely for illustrative purposes and do not limit the technical scope of the present invention. The technical scope of the present invention is only limited by the claims. Modifications of the present invention, for example, addition, deletion, and replacement of the constituent features of the present invention, can be made on the condition that there is no deviation from the spirit of the present invention.

EXAMPLES

Example 1

Synthesis of Polyvinyl Alcohol (PVA)

<Reagents>

Unless otherwise specified, commercially available reagents and solvents were used as they were.
Vinyl acetate: a commercial product (Wako, Wako special grade) distilled under an argon atmosphere was used.
Cyanomethyl methyl (phenyl) carbamodithioate: Sigma Aldrich
α, α'-azobisisobutyronitrile (AIBN): Sigma Aldrich
Methanol (MeOH) (special grade): Nacalai Tesque
5 mol/l hydrochloric acid (for mass spectrometry): Wako Pure Chemical Industries, Ltd.
5 mol/l sodium hydroxide (for mass spectrometry): Wako Pure Chemical Industries, Ltd.
Benzene (special grade): Wako Pure Chemical Industries, Ltd.
Tetrahydrofuran (THF): Wako Pure Chemical Industries, Ltd.
Sodium dihydrogen phosphate ($NaH_2PO_3$): Wako Pure Chemical Industries, Ltd.
Disodium hydrogen phosphate: Nacalai Tesque
<Equipment>
NMR (Nuclear Magnetic Resonance): BRUKER AVANCE III 400 (400 MHz, BRUKER BioSpin)
GPC (Gel Permeation chromatography): JASCO Corporation
Column for measuring PVAc: TSK-gel superAW3000, superAW4000, and superAWL-guard
column (Tosoh Corporation)
Column for measuring PVA: Superdex 200 Increase 10/300 GL (GE Healthcare)
Detector: RI-2031
(1) Synthesis of poly(vinyl acetate) (PVAc)

[Chem. 63]

2.86 mg (0.0174 mmol) of an initiator AIBN and 38.68 mg (0.174 mmol) of the RAFT agent cyanomethyl methyl (phenyl) carbamodithioate were weighed and added to a 100 mL two-necked pear-shaped flask under an argon atmosphere in an ice bath. Thereafter, 3.22 mL (34.8 mmol) of vinyl acetate was added to the system under an argon atmosphere, and freeze-pump-thaw degassing was performed 4 times. The system was filled with argon and stirred at 60° C. for 24 hours. Thereafter, the reaction solution was put into a dialysis membrane (MWCO=3.5 kD), dialyzed 3 times for 12 hours against a 300 mL THF solution and then freeze-dried from a benzene solution. The target PVAc was obtained as a light yellow solid at a yield of 2.97 g. The resulting PVAc was analyzed by $^1$H-NMR and GPC.

From $^1$H-NMR, it was calculated that the degree of polymerization of PVAc was 172 and Mn=14,800. Specifically, by using the RAFT agent-derived aromatic ring signal (7.56 to 7.28 ppm, (br, Ar—H)) as a reference (5H), the number average molecular weight was calculated based on the main chain skeleton-derived signal (1.84 to 1.66 ppm (br, —$CH_2$)) and ester group-derived signal (2.04 to 1.85 ppm (br, O—CO—$CH_3$)). The GPC curve was unimodal, the molecular weight distribution Mw/Mn=1.31 was narrow, and the molecular weight was calculated as Mn=12,800. Since the molecular weight determined by GPC is a relative molecular weight based on standard polyethylene glycol, hereinafter, $M_n$ will be the molecular weight as obtained by $^1$H-NMR.

[Chem. 64]

$^1$H-NMR (400 MHz, DMSO-$d_6$): δ 7.56-7.28 (br, —Ar—H), 4.90-4.68 (br, —$CHCH_2$—), 2.04-1.85 (br, —$OCOCH_3$) 1.84-1.66 (br, —$CHCH_2$—)

(2) Synthesis of Polyvinyl Alcohol (PVA)

[Chem. 65]

1.00 g (0.062 mmol) of the PVAc obtained in (1) above was weighed and dissolved in 30 mL of MeOH in a 300 mL pear-shaped flask. 2.32 g (57.94 mmol) of sodium hydroxide (5 equivalents) was added to the ester of PVAc, pure water was further added thereto, then the mixture was stirred at 60° C. for 24 hours. The reaction solution was put into a dialysis membrane (MWCO=3.5 kD) and dialyzed 3 times against 2 L of pure water. The resulting polymer solution was filtered through a 0.45 μm filter and then freeze-dried. The target PVA was obtained as a light yellow solid at a yield of 240 mg. The obtained PVA was analyzed by $^1$H-NMR and GPC. From $^1$H-NMR, it was determined that the saponification rate was 99% by mol. Moreover, it was confirmed that the GPC curve of the obtained PVA was unimodal. Note that "*" and "**" in the above chemical formulas have undetermined structures.

[Chem. 66]

$^1$H-NMR (400 MHz, DMSO-$d_6$): δ 4.76-4.18 (br, —OH), 4.08-3.75 (br, —$CHCH_2$—), 1.78-1.08 (br, —$CHCH_2$—)

Example 2

Evaluation of Bonding of BPA Derivative (PVA-BPA) in which BPA is Bonded to PVA

<Reagents>

Unless otherwise specified, commercially available reagents and solvents were used as they were.

5 mol/l hydrochloric acid (for mass spectrometry): Wako Pure Chemical Industries, Ltd.

mol/l sodium hydroxide (for mass spectrometry): Wako Pure Chemical Industries, Ltd.

Sodium dihydrogen phosphate ($NaH_2PO_3$): Wako Pure Chemical Industries, Ltd.

4-Borono-L-phenylalanine (BPA) (boron of this reagent is $^{10}B$): Katchem

4-Borono-L-phenylalanine ($^{11}B$-BPA) (boron of this reagent is in a mixed form of $^{11}B$-BPA and $^{10}B$-BPA): Sigma-Aldrich Alizarin Red S (ARS): Wako Pure Chemical Industries, Ltd.

Disodium hydrogen phosphate: Nacalai Tesque

D-fructose (also referred to as "Fru" below): Wako Pure Chemical Industries, Ltd.

Note that the BPA derivative obtained by reacting Fru and BPA is also referred to as "Fru-BPA" below.

<Equipment>

NMR (Nuclear Magnetic Resonance): BRUKER AVANCE III HD500 (500 MHz, BRUKER BioSpin)

Fluorescence spectrophotometer (FP8300): JASCO Corporation

The $^{11}B$-BPA solution, Fru-$^{11}B$-BPA solution and PVA-$^{11}B$-BPA solution were prepared to the following concentrations using 10 mM PBS (140 mM NaCl, pH 9.5).

$^{11}B$-BPA solution: $^{11}B$-BPA concentration 191.3 mM=40 mg/mL

Fru-$^{11}B$-BPA solution: $^{11}B$-BPA concentration 191.3 mM=40 mg/mL, fructose concentration 103.2 mg/mL PVA-$^{11}B$-BPA solution: $^{11}B$-BPA concentration 191.3 mM=40 mg/mL, diol concentration in PVA 573.9 mM=50.4 mg/mL 450 µL of each sample and 50 µL of $D_2O$ were mixed, and $^{11}B$-NMR was measured. The result of the $^{11}B$-NMR spectroscopy is illustrated in FIG. 1. The peak with the highest signal intensity was for the BPA solution (br, 2.1 ppm to 10.0 ppm). The peaks for the PVA-BPA solution and Fru-BPU solution are clearly different from the BPA solution signal, and in addition, because the signal intensity of BPA itself decreased it was qualitatively determined that the PVA and BPA were binding.

In the above PVA-$^{11}B$-BPA solution, it was calculated, on the basis of the equilibrium constant (pH 7.4), that (free BPA):(BPA bound to PVA)=10:90 to 0:100 (molar ratio). Note that since the pH of the PVA-$^{11}B$-BPA solution was 9.5 and the higher the pH, the higher the equilibrium constant, it was estimated that almost 100% of BPA was bound to PVA in the solution.

The equilibrium constant of PVA and BPA was calculated using the ARS method according to the method described in Springsteen G., Wang B. H. Tetrahedron 58, 5291-5300 (2002). Initially, each of the following solutions A, B, C, and D were prepared.

Solution A: ARS ($9.0\times10^{-6}$ M)
Solution B: ARS ($9.0\times10^{-6}$ M)+BPA ($2.0\times10^{-3}$ M)
Solution C: ARS ($9.0\times10^{-6}$ M)+BPA ($2.0\times10^{-3}$ M)+PVA (diol concentration=$5.0\times10^{-1}$ M)
Solution D: ARS ($9.0\times10^{-6}$ M)+BPA ($2.0\times10^{-3}$ M)+fructose ($0.8\times10^{-1}$ M)
Solution E: ARS ($9.0\times10^{-6}$ M)+BPA ($2.0\times10^{-3}$ M)+glucose ($0.8\times10^{-1}$ M)

Solution A and Solution B were mixed at various ratios, and fluorescence was measured using a disposable cell (PS, TGK) ($E_x$=468 nm, $E_m$=572 nm). The equilibrium constant $K_0$ of ARS-BPA was calculated from the obtained fluorescence intensity. Next, Solution B was mixed with Solution C, D, or E containing each diol compound, at various ratios, and fluorescence was measured using a disposable cell ($E_x$=468 nm, $E_m$=572 nm). The apparent relative equilibrium constant $K_1$ of each compound (diol [2OH] concentration equivalent)-BPA was calculated using these results and the aforementioned $K_0$ value. The results are illustrated below in table 1.

TABLE 1

| | Glucose (diol)-BPA | PVA (diol)-BPA | Fructose (diol)-BPA |
|---|---|---|---|
| Relative equilibrium constant ($K_1$) | 1.0 | 1.9 | 46 |

In the above solution C, it was calculated, on the basis of the equilibrium constant (pH 7.4), that (free BPA):(BPA bound to PVA)=approximately 50:50 (molar ratio).

Example 3

Intracellular Uptake of PVA-BPA

<Reagents>

Roswell Park Memorial Institute Medium (RPMI): Sigma Aldrich

D-PBS (−): Wako Pure Chemical Industries, Ltd.

Fetal bovine serum (FBS): Biosera

Trypsin-EDTA solution: Sigma life science

Penicillin/Streptomycin: Sigma life science

Cy5-NHS: Thermo Fisher Scientific

LysoTracker® red DND-99: Thermo Fisher Scientific

4-Diethylaminosalicylaldehyde: Tokyo Chemical Industry Co., Ltd.

Methylamine: Tokyo Chemical Industry Co., Ltd.

DMSO: Nacalai Tesque

2-Aminonorbomane-2-carboxylic acid (BCH): Sigma-Aldrich

Hoechst® 33342: Thermo Fischer Scientific.

4-Bromo-L-phenylalanine (BPA): Katchem PVA manufactured by the same method as in EXAMPLE 1 (Mn=6,500 to 9,500)

Disodium hydrogen phosphate: Nacalai Tesque

DAHMI: Produced according to the method described in Springsteen G., et al., Acs Sensors 1, 1394-1397 (2016).

Cell strainer: Falcon cell strainer 35 µm for 5 mL tubes

BxPC3 cells (human pancreatic cancer cell line): American Type Culture Collection (Manassas, Va.)

<Equipment>

Flow Cytometer (FCM): Guava easy Cyte 6-2L (Merck Millipore)

Confocal Laser Scanning Microscope (CLSM): LSM710 (Carl Zeiss)

Agilent 7900 ICP-MS (Agilent Technology Co., Ltd.)

NMR (Nuclear Magnetic Resonance): BRUKER AVANCE III 400 (400 MHz, BRUKER BioSpin)

(1) Synthesis of BPA Derivative (Cy5-PVA-BPA) in which Cy5 is Bonded to PVA-BPA 125 mg ($1.67\times10^{-2}$ mmol) of PVA was weighed in a 6 mL vial and dissolved in 2.5 mL of DMSO. Next, 1.23 mL ($2.00 \times 10^{-2}$ mmol) of Cy5-NHS (1.2 equivalents) was added to the PVA solution, and the mixture was stirred at room temperature for 3 hours. The reaction solution was put into a dialysis membrane (MWCO=3.5 kD) and dialyzed three times against 2 L of pure water. To completely remove free Cy5 in the dialysis solution, the product was purified using a PD-10 column and then freeze-dried to obtain the reaction product of PVA and Cy5-NHS (Cy5-PVA) as a blue solid (yield 122 mg). Cy5-PVA-BPA was prepared by mixing Cy5-PVA and BPA in 10 mM PBS (140 mM NaCl, pH 9.5) such that the diol concentration in PVA was 0.34 mM and the BPA concentration was 0.11 mM. In the prepared solution, it was calculated, on the basis of the equilibrium constant (pH 7.4), that (free BPA):(BPA bound to PVA)=approximately 60:40 (molar ratio).

(2) Evaluation of Cellular Uptake of Cy5-PVA-BPA Using Confocal Microscopy

Figure 2:
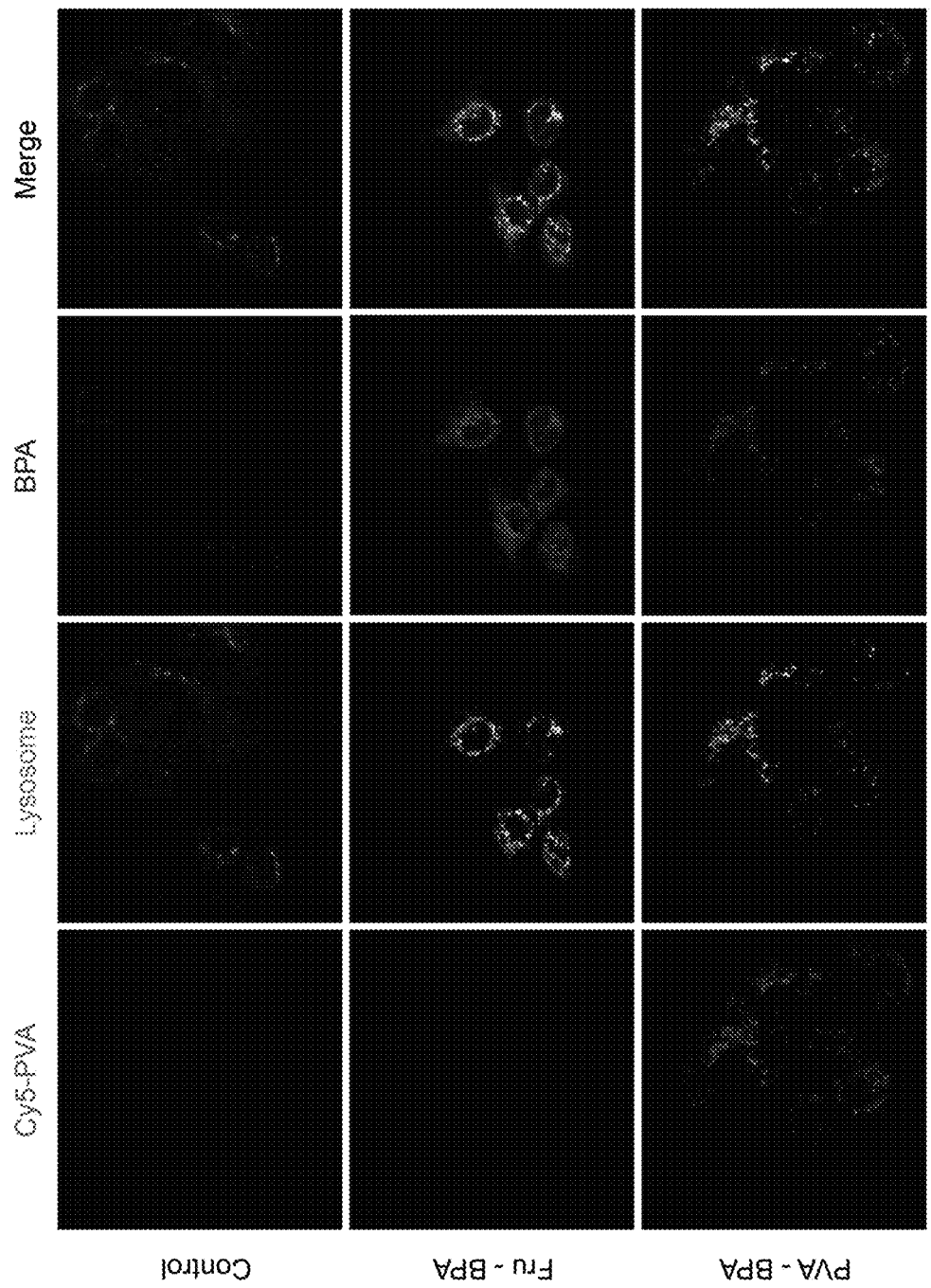
FIG. 2 shows confocal microscopy images of BxPC3 cells treated with Cy5-PVA-BPA and Fru-BPA. In the figure, the controls are BxPC3 cells that were not treated with any of the samples (Lysotracker for staining and BPA detection reagent (DAHMI) were added).

BxPC3 cells were inoculated in a glass base dish (AGC Technoglass) at $5 \times 10^4$ cells/dish and precultured for 24 hours. The Cy5-PVA-BPA solution or Fru-BPA solution (fructose concentration=0.28 mM, BPA concentration=0.11 mM) prepared in (1) above was prepared in a mixed solution of D-PBS/RPMI culture medium (containing 10% FBS, 1% Penicillin-Streptomycin) (PBS:RPMI=1:4), and 1 mL of each of these samples was added to each well and incubated for 30 minutes. After removing the culture medium, 2 mM DAHMI (compound for BPA fluorescence detection)/10 μL DMSO solution and 50 nM Lyso Tracker® red DND-99/PBS solution 990 μL were added to each well and incubated for 30 minutes. The cells were washed three times with 1 mL PBS, 1 mL of PBS was then added thereto, and then the cells were observed by CLSM. The results are illustrated in FIG. 2. It was confirmed that when Fru-BPA was taken up intracellularly, the BPA was distributed throughout the cytoplasm. On the other hand, FIG. 2 indicates that Cy5-PVA and BPA colocalize with lysosomes, suggesting that Cy5-PVA-BPA is incorporated by endocytosis.

Example 4

Evaluation of Intracellular Uptake of PVA-BPA and LAT1 Mediation Thereof

BxPC3 cells were inoculated in a petri dish at $5 \times 10^6$ cells/well and precultured for 24 hours. Next, a D-PBS/RPMI (10% FBS, 1% penicillin-streptomycin) culture medium solution (D-PBS: RPMI=1:4) was used to prepare the following samples.

PVA-BPA solution (diol concentration=3.03 mM, BPA concentration=3.03 mM)

Fru-BPA solution (fructose concentration=7.82 mM, BPA concentration=3.03 mM)

The above PVA-BPA solution+BCH (LAT1 inhibitor)(20 mM)

The above Fru-BPA solution+BCH (20 mM)

In the above PVA-BPA solution, it was calculated, on the basis of the equilibrium constant (pH 7.4), that (free BPA):(BPA bound to PVA)=approximately 30:70 (molar ratio).

10 mL of these samples were added to each petri dish and incubated for 3 hours. Each well was washed with 10 mL of D-PBS, 1.0 mL of trypsin-EDTA solution was then added thereto and then incubation was performed for 10 minutes. Note that with respect to PVA-BPA and Fru-BPA, samples were also prepared in which, after washing with D-PBS, fresh culture liquid was added and incubation was performed for a further 30 minutes. Thereafter, washing was performed with D-PBS, then 1.0 mL of trypsin-EDTA solution was added and incubation was carried out for 10 minutes. After confirming that the cells had detached by using an optical microscope, 9.0 mL of an RPMI culture medium containing 10% FBS was added, and a cell suspension was prepared. Centrifugation at 1500 rpm was performed for 5 minutes at 24° C. and the supernatant was removed. The number of cells was counted, then the sample solution was poured into a 15 mL falcon tube and 1 mL of 70% nitric acid was added. Thereafter, each sample was incubated at 50° C. for 15 minutes, 70° C. for 15 minutes, and 90° C. for 1 hour. The samples were diluted to 10 mL with pure water, filtered through a hydrophobic filter, then evaluated using ICP-MS. The results are illustrated in FIGS. 3-1 and 3-2.

Figures 1, 3:
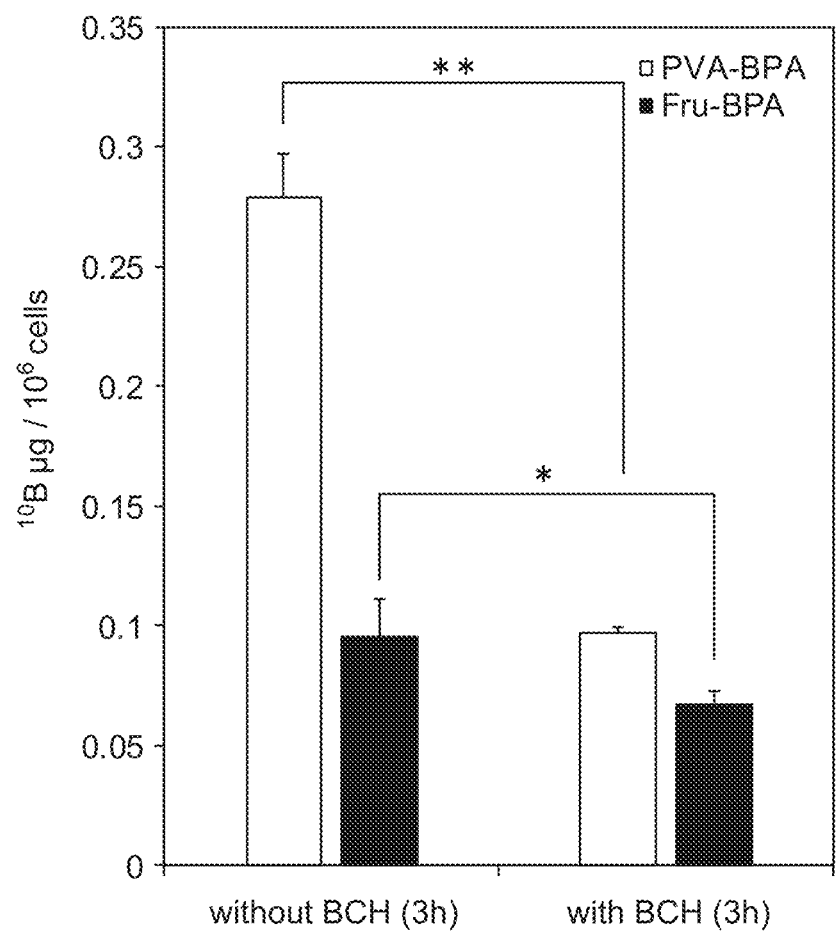
Figures 2, 3:
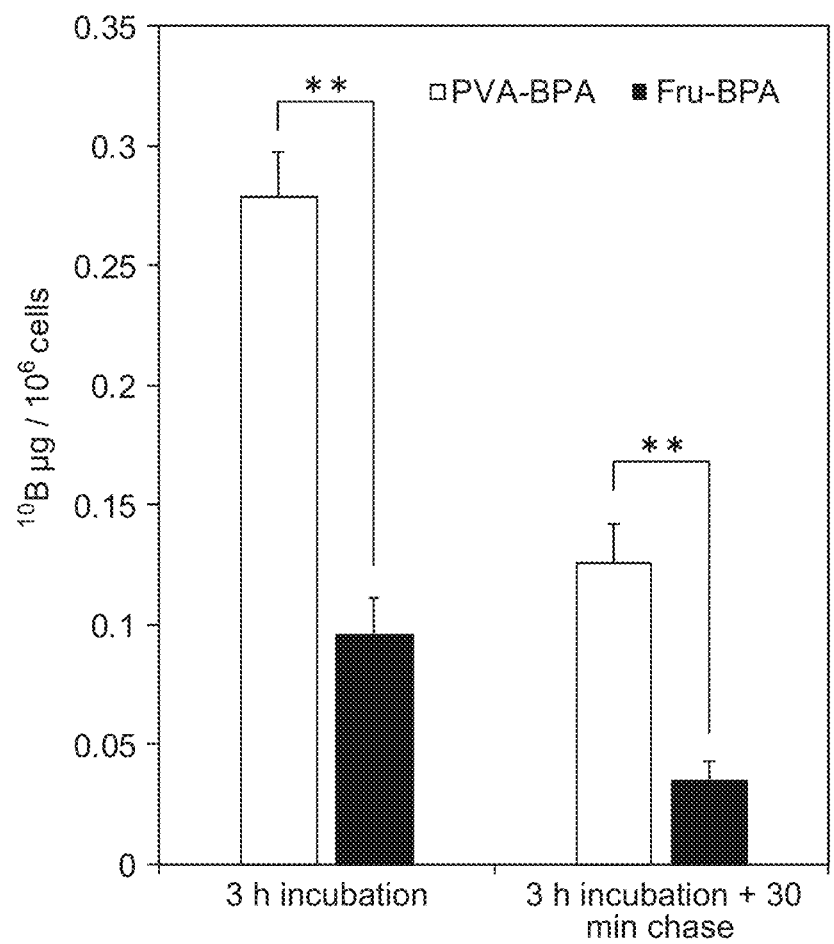

As can be seen from FIG. 3-1, compared to Fru-BPA, PVA-BPA exhibits approximately three times the intracellular boron concentration. On the other hand, when the LAT1 inhibitor BCH(2-aminobicyclo [2.2.1] heptane-2-carboxylic acid) was used, the intracellular uptake of both Fru-BPA and PVA-BPA was significantly reduced. These results suggest that the intracellular uptake of PVA-BPA occurs through LAT1 mediated endocytosis. Furthermore, FIG. 3-2 shows that by performing an additional 30 minutes of incubation, the Fru-BPA significantly reduced the intracellular boron concentration. In contrast thereto, PVA-BPA exhibited extremely high boron concentrations even after performing additional incubation.

Example 5

Effect of BPA on PVA Intracellular Uptake

BxPC3 cells were inoculated on a 12-well plate at $1 \times 10^5$ cells/well and precultured for 24 hours (n=3). Next, a D-PBS/RPMI (10 FBS, 1% penicillin-streptomycin) culture medium solution (D-PBS:RPMI=1:4) was used to prepare the following samples.

Cy5-PVA-BPA solution (PVA diol concentration=0.34 mM, BPA concentration=0.11 mM)

The above Cy5-PVA-BPA solution+BCH (20.0 mM)

In the above Cy5-PVA-BPA solution, it was calculated, on the basis of the equilibrium constant (pH 7.4), that (free BPA):(BPA bound to PVA)=approximately 60:40 (molar ratio).

1 mL of these samples were added to each well and incubated for 30 minute, 3 hours, and 6 hours. Each well was washed with 1 mL of PBS, 0.5 mL of trypsin-EDTA solution was then added thereto, and then incubation was performed for 10 minutes. After confirming that the cells had detached by using an optical microscope, 0.5 mL of an RPMI culture medium containing 10% FBS was added and a cell suspension was prepared. The prepared cell suspension was filtered through a cell strainer, then the Cy5 fluorescence intensity of the cells was quantified using a flow cytometer. The results are illustrated in FIGS. 4-1 and 4-2.

Figures 1, 4:
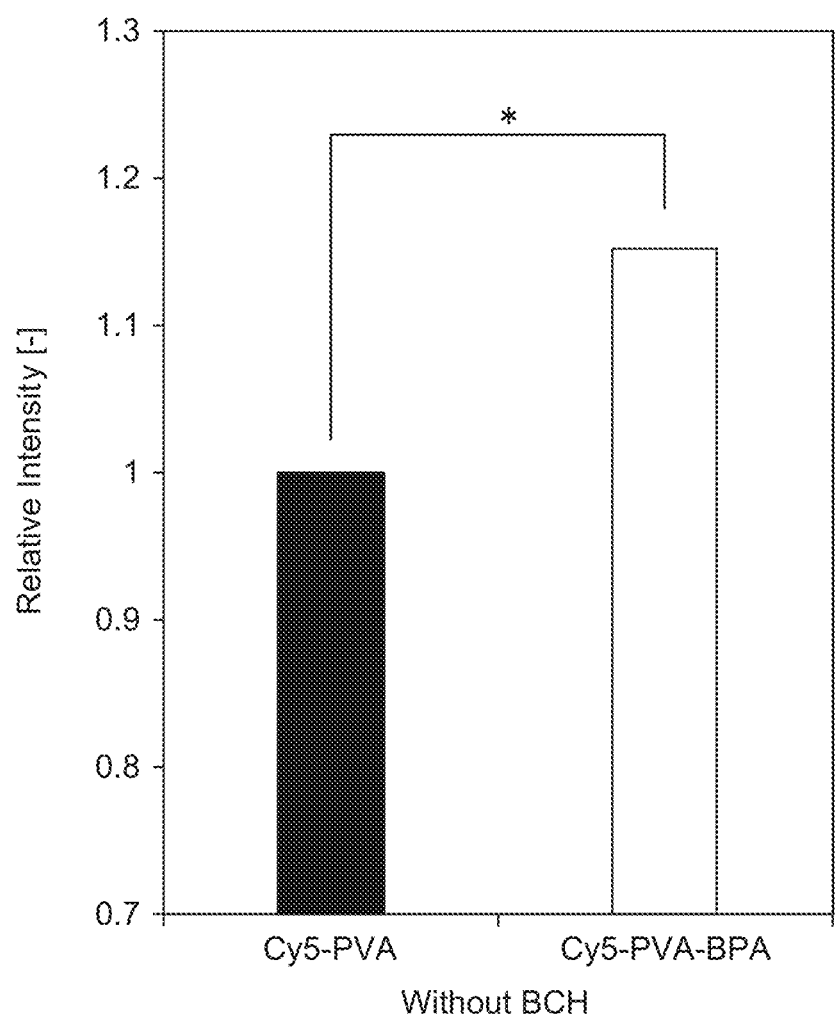
Figures 2, 4:
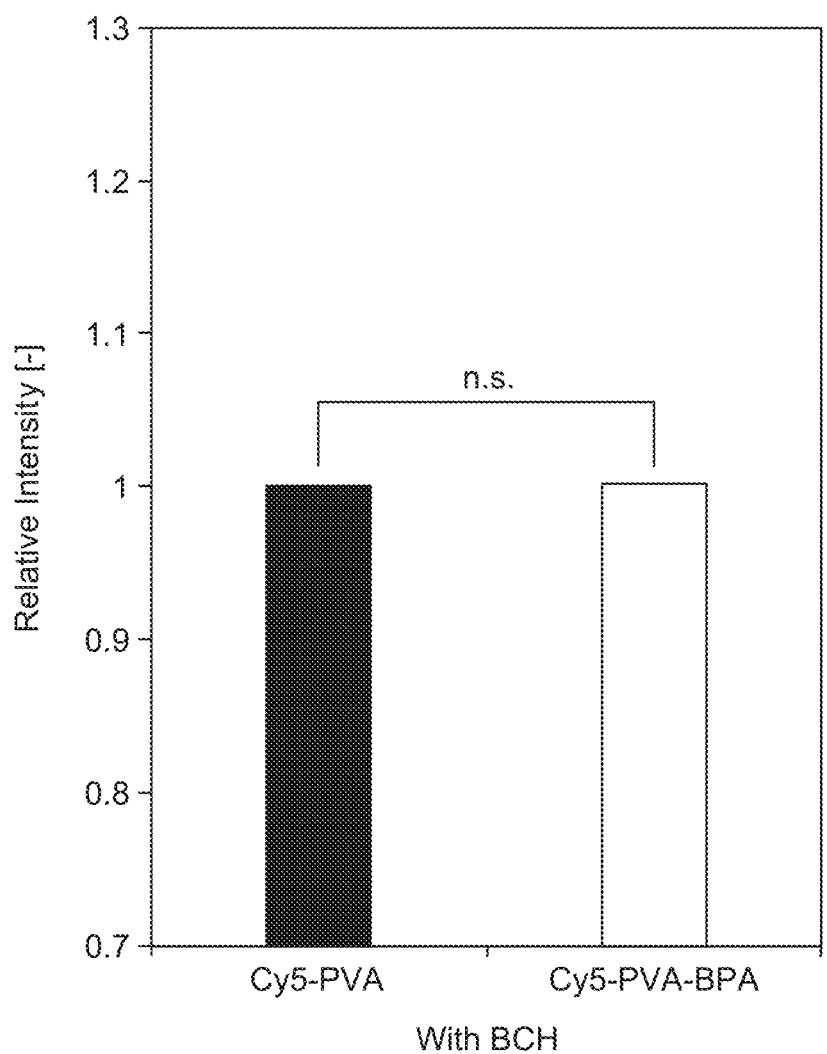

The Cy5-PVA-BPA exhibited significantly higher intracellular uptake than Cy5-PVA (FIG. 4-1). In contrast, this difference in uptake disappeared when LAT1 was inhibited with BCH (FIG. 4-2). Similar to EXAMPLE 4, these results suggest that the intracellular uptake of PVA-BPA occurs through LAT1 mediated endocytosis.

Example 6

Effect on Subcutaneous Tumor Model
<Reagents, Cells, and Animals>
PVA was manufactured by the same method as in EXAMPLE 1 (Mn=6,500 to 9,500)

5 mol/l hydrochloric acid (for mass spectrometry): Wako Pure Chemical Industries, Ltd.
5 mol/l sodium hydroxide (for mass spectrometry): Wako Pure Chemical Industries, Ltd.
4-Borono-L-phenylalanine (BPA): Katchem
Disodium hydrogen phosphate: Nacalai Tesque
Lemosol: Wako Pure Chemical Industries, Ltd.
Drysol: Kanto Chemical Co., Inc.
Cryostat: Leica CM 3050S, Leica Microsystems, Nussloch GmbH, Germany O.C.T compound: Sakura Finetek Japan, Inc.
Hoechst® 33342: Thermo Fischer Scientific
Tomato lectin, DyLight 488 conjugate: Funakoshi
BxPC3 cells (human pancreatic cancer cell line): American Type Culture Collection (Manassas, Va.)
CT26 cells (mouse colon cancer cell line): American Type Culture Collection (Manassas, Va.)
BALB/c mouse: Charles River Japan
BALB/c nude mouse: Charles River Japan
<Equipment>
Agilent 7900 ICP-MS: Agilent Technology Co., Ltd.
Confocal Laser Scanning Microscope (CLSM): LSM710 (Carl Zeiss)
Fuji Drychem NX500: Fujifilm Corporation
Heavy Water Neutron Irradiation Facility: KUR
All-in-one fluorescence microscope (BZ-X710): KEYENCE Subcutaneous tumor models were prepared by subcutaneously injecting CT26 cells into BALB/c mice at $2.0 \times 10^5$ cells/mouse and subcutaneously injecting BxPC3 cells into BALB/c nude mice at $5.0 \times 10^6$ cells/mouse. Once the tumor size had reached about 200 mm$^3$, 200 μL of the following samples were slowly administered through the tail vein (BPA 8 mg/mouse). PVA-BPA (BPA concentration=191 mM, PVA diol concentration=574 mM) in PBS (pH 9.5) Fru-BPA (BPA concentration=191 mM, fructose concentration=574 mM) in PBS (pH 9.5)

Figures 1, 5:
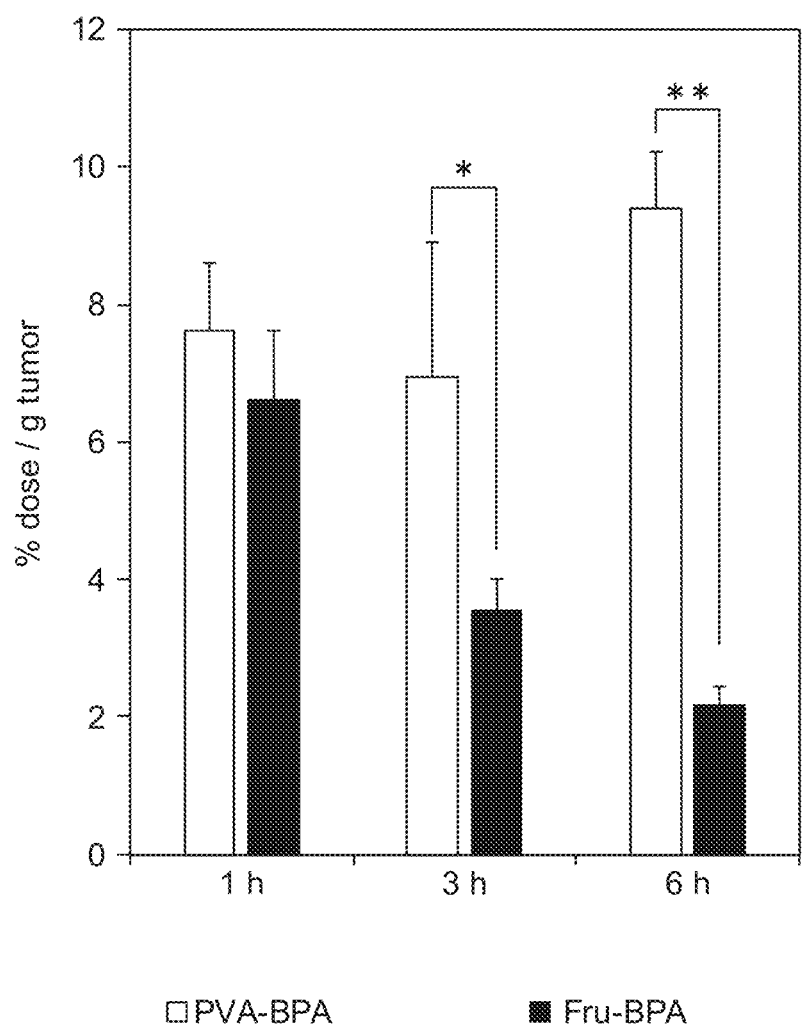
Figures 2, 5:
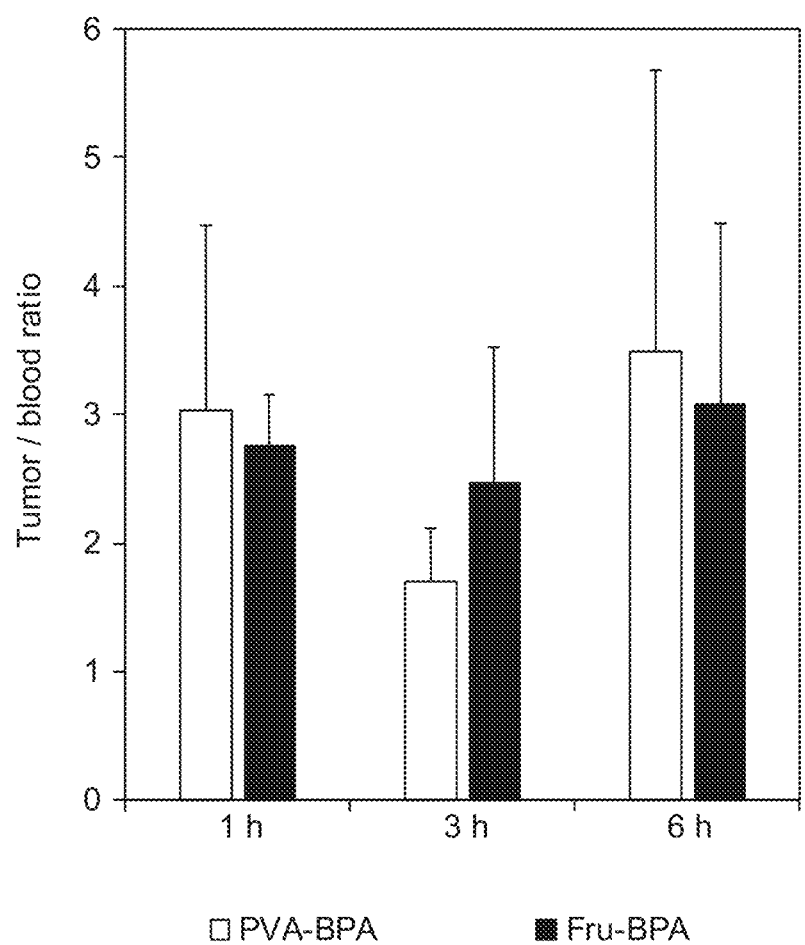
Figures 1, 6:
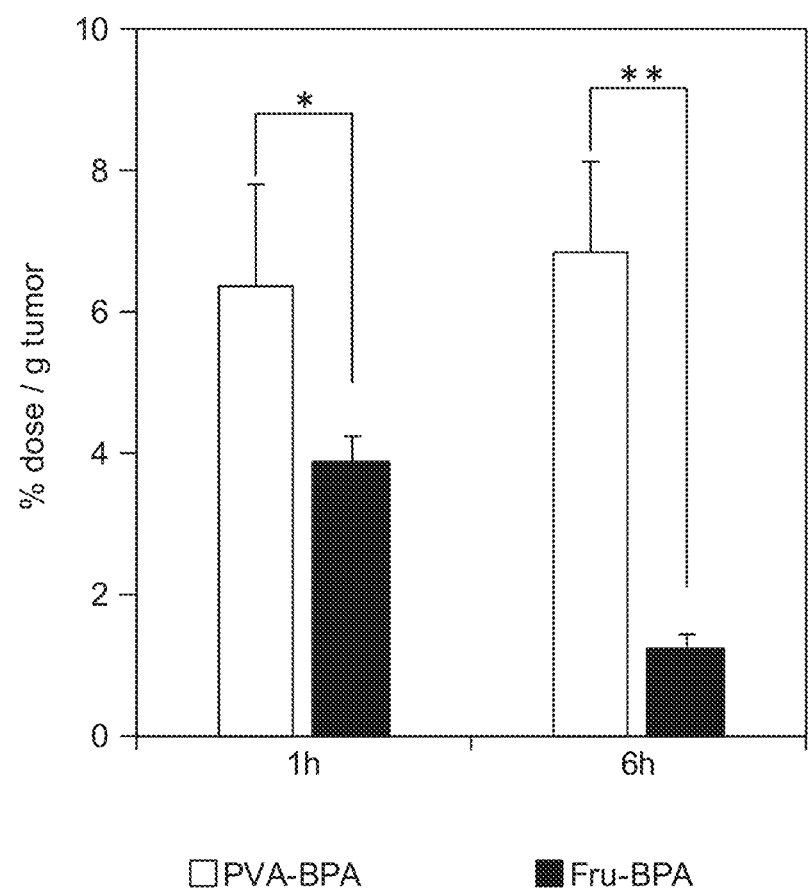
Figures 2, 6:
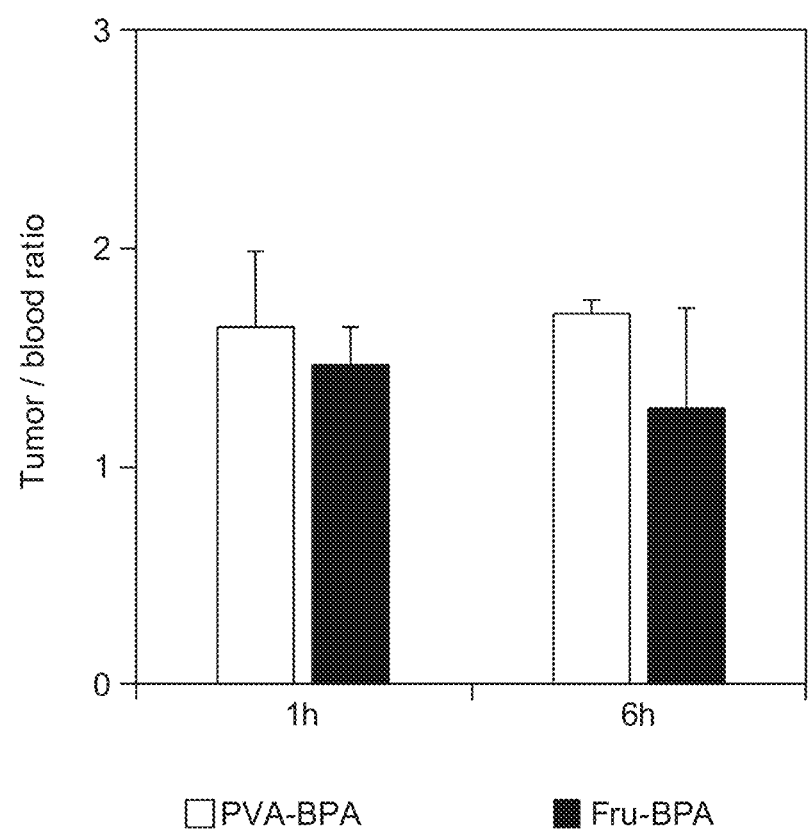

After a predetermined time from administration of the sample, the mice were dissected, blood was collected, and the tumors were removed. Blood and various organs were placed in a 10 mL falcon tube, and 1 mL of 70% nitric acid was added. Thereafter, each sample was incubated at 50° C. for 15 minutes, 70° C. for 15 minutes, and 90° C. for 1 hour. The samples were diluted to 10 mL with pure water, filtered through a hydrophobic filter, then evaluated using ICP-MS. The results of pharmacokinetic analysis of CT-26 transplanted mice are illustrated in FIGS. 5-1 and 5-2 and the results of pharmacokinetic analysis of BxPC3 transplanted mice are illustrated in FIGS. 6-1 and 6-2. PVA-BPA showed excellent tumor accumulation in all tumors and could maintain high intratumoral boron concentration for a long time. Also, the tumor/blood ratio was comparable to that of conventional Fru-BPA.

Example 7

Cy5-PVA-BPA Tumor Penetration Test

Figure 7:
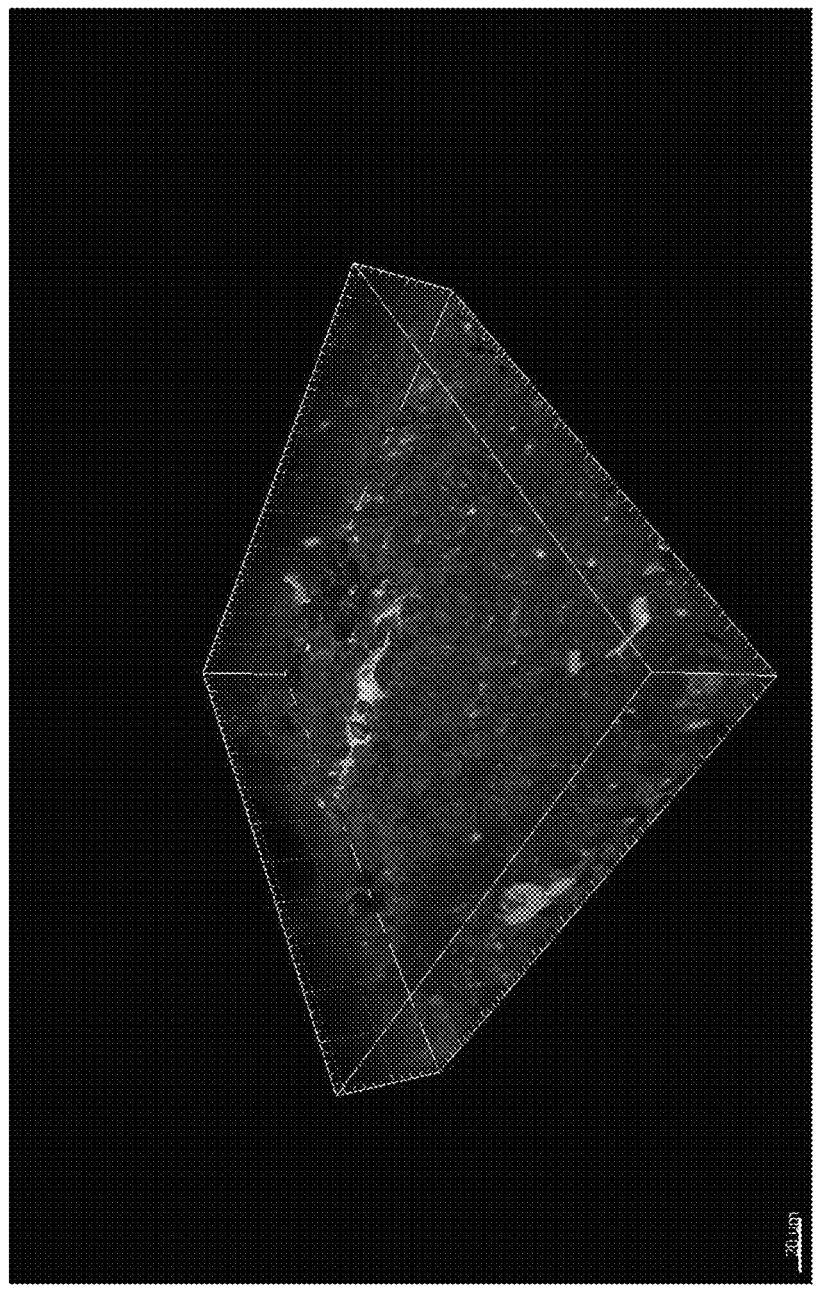
FIG. 7 shows a CLSM image of a CT26 tumor six hours after intravenous injection of Cy5-PVA-BPA. Red: Cy5; Blue: Hoechst33342 (nucleus); Green: DyLight488 (blood vessels).

In the same way as in EXAMPLE 6, a Cy5-PVA-BPA solution and a CT26 subcutaneous tumor model were prepared, and once the tumor size had reached about 200 mm$^3$, 200 μL of the sample was slowly administered through the tail vein (BPA 8 mg/mouse). 5.5 hours after administration, tomato lectin-DyLight488 solution (50 μg) and Hoechst 33342 (50 μg) were intravenously administered. The tumor was removed 6 hours after sample administration, the tumor was cut through the center, and the section was placed on a glass-based dish and observed by CLSM. The results are illustrated in FIG. 7. The overall distribution of Cy5-PVA suggested that BPA could be delivered throughout the tumor.

Example 8

Antitumor Effect

CT-26 cells were subcutaneously implanted ($2.0 \times 10^5$ cells/mouse) near the right thigh of BALB/c mice, and 250 μL of the following samples were slowly administered through the tail vein of mice with a tumor size of about 50 to 100 mm$^3$ (BPA 10 mg/mouse). PVA-BPA (BPA concentration=191 mM, PVA diol concentration=574 mM) in PBS (pH 9.5) Fru-BPA (BPA concentration=191 mM, fructose concentration=574 mM) in PBS (pH 9.5)

In the above PVA-$^{11}$B-BPA solution, it was calculated, on the basis of the equilibrium constant (pH 7.4), that (free BPA):(BPA bound to PVA)=10:90 to 0:100 (molar ratio). Note that since the pH of the PVA-BPA solution was 9.5 and the higher the pH, the higher the equilibrium constant, it was estimated that almost 100% of BPA was bound to PVA in the solution.

In the neutron irradiation group, neutron irradiation was performed for 50 minutes only around the right thigh of the mouse 3 hours and 6 hours after the sample administration. With the day of irradiation set as the first day, the tumor diameter was measured every 2 to 3 days with electronic calipers and the body weight was measured with an electronic balance for a total of 25 days. The measured tumor diameter was used in an elliptic volume approximation formula (ab$^2 \times$½, where a is the long side and b is the short side) to give the tumor volume. The evaluated groups are summarized below.
Control (COLD) (n=8): untreated group.
Fru-BPA (COLD) (n=8): injected with only Fru-BPA.
PVA-BPA (COLD) (n=8): injected with only PVA-BPA.
Control (HOT) (n=8): only irradiated with neutrons.
Fru-BPA (HOT) 3h (n=8): injected with Fru-BPA then irradiated with neutrons 3 hours thereafter.
PVA-BPA (HOT) 3h (n=4): injected with PVA-BPA then irradiated with neutrons 3 hours thereafter.
PVA-BPA (HOT) 6h (n=8): injected with PVA-BPA then irradiated with neutrons 6 hours thereafter.

Figures 1, 8:
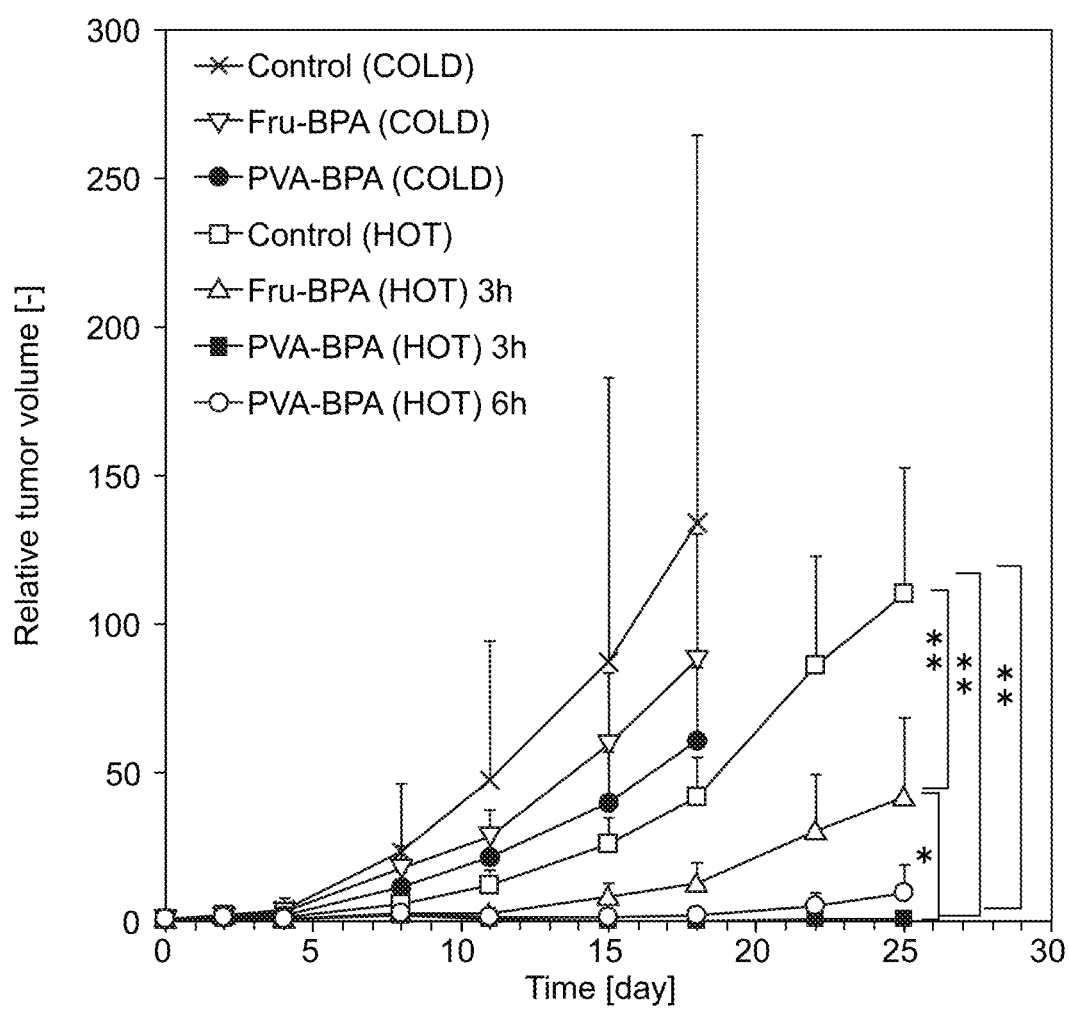
Figures 2, 8:
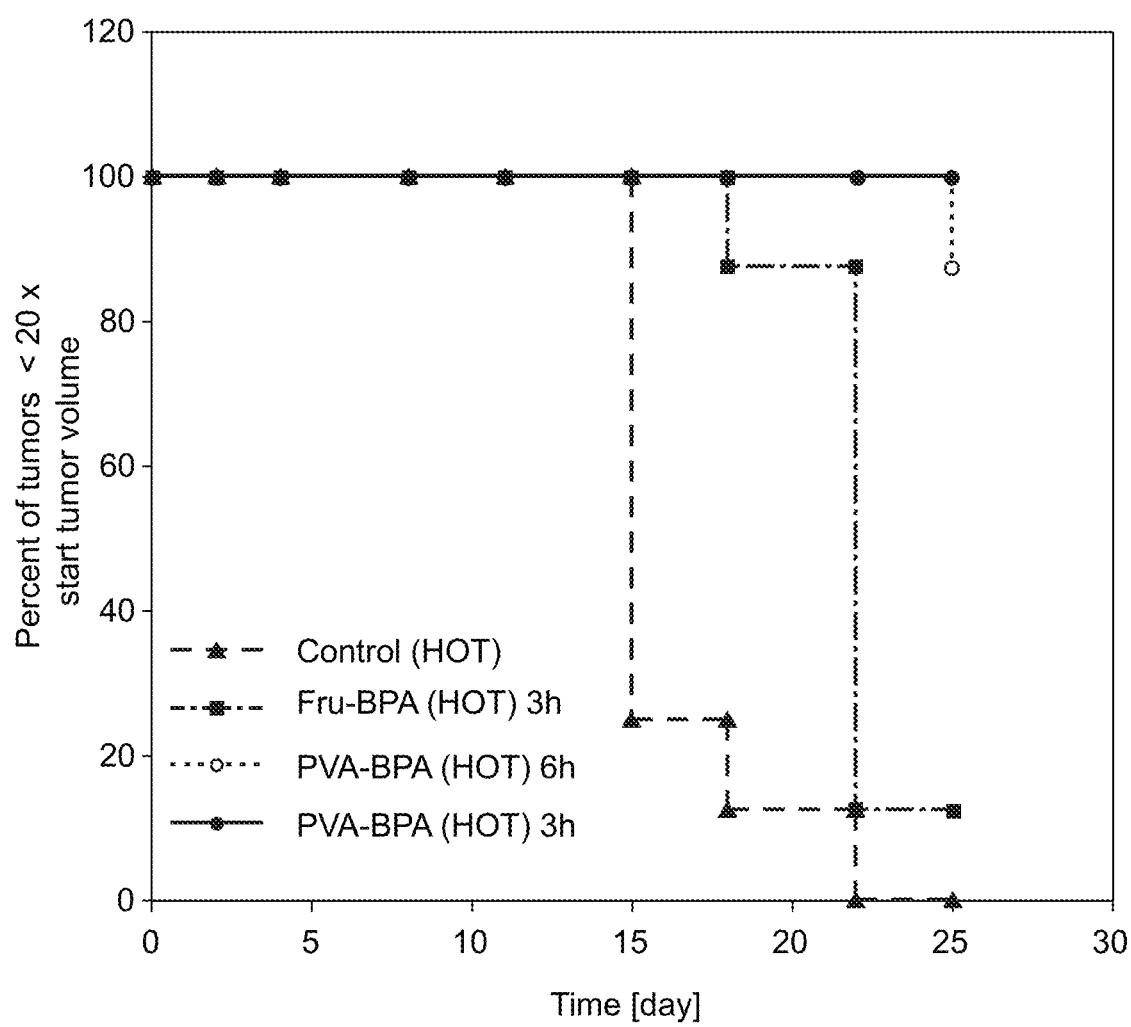

The change in tumor size over time and the Kaplan-Meier curves are shown in FIGS. 8-1 and 8-2. PVA-BPA showed a significant inhibitory effect on tumor growth in neutron capture therapy compared to Fru-BPA.

Figures 1, 9:
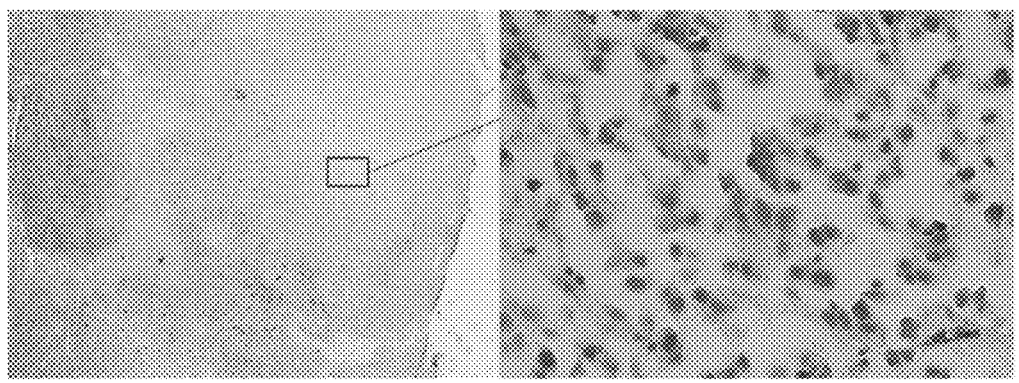
Figures 2, 9:
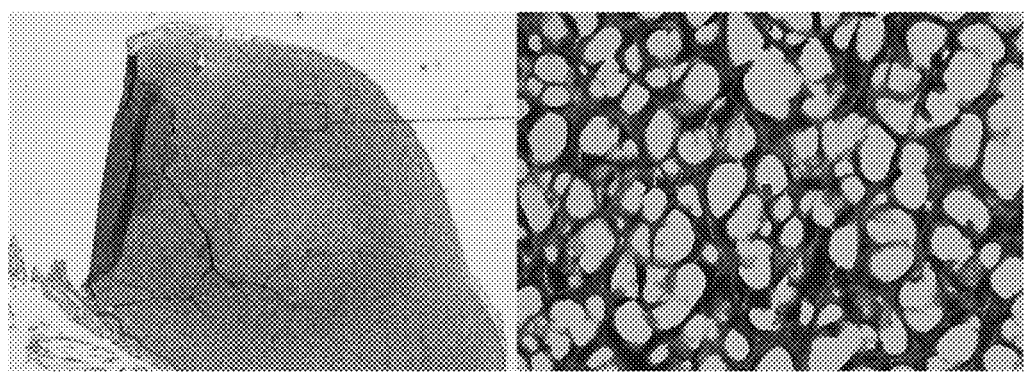
Figures 3, 9:
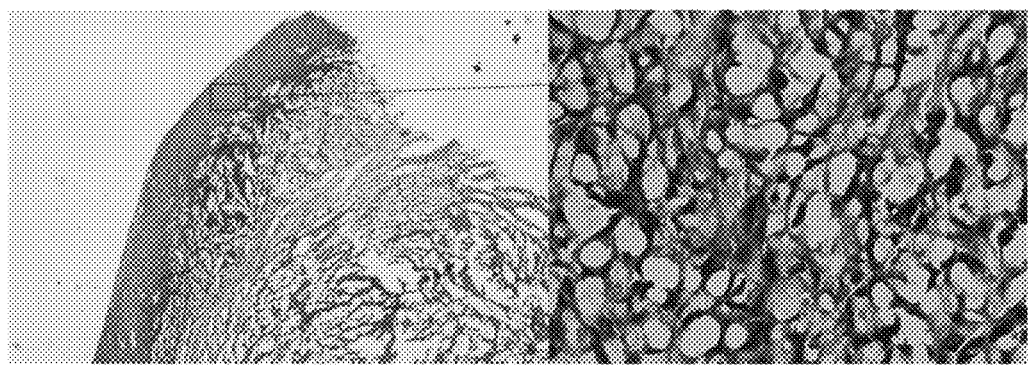
Figures 4, 9:
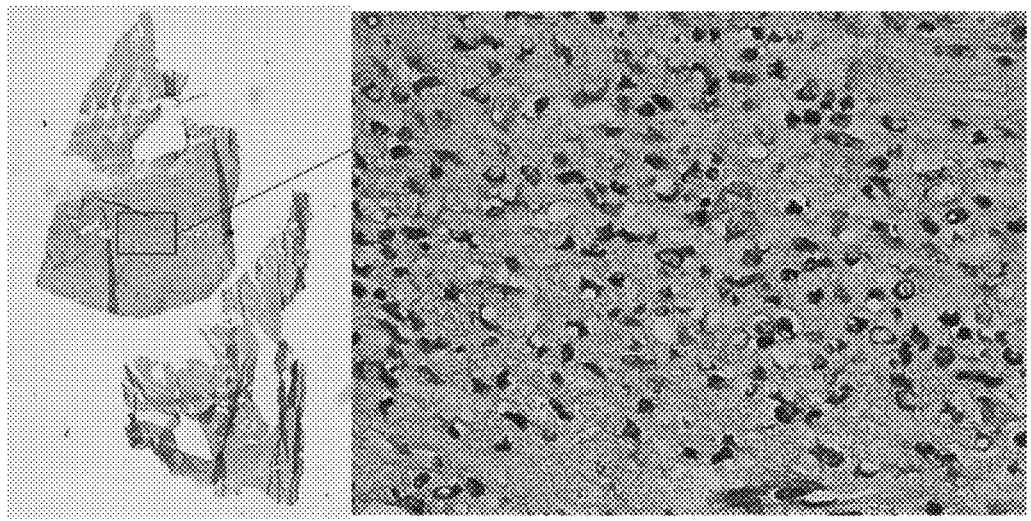

Twenty-five days after irradiation with thermal neutrons, the tumor was removed and immersed in formalin solution for 4 days. The tumor was removed from the formalin solution and sliced through the center of the tumor tissue. The excised organs were treated with an embedding medium (O.C.T. compound) for frozen section preparation, and then a tissue section of 4 μm was prepared using a cryostat and subjected to HE staining. The results are illustrated in FIGS. 9-1 to 9-4. PVA-BPA (HOT) 3h (FIG. 9-4) suggests that apoptosis is induced in the entire tumor which is consistent with the effects of the antitumor effect experiment.

Example 9

$^{19}$F Nuclear Magnetic Resonance Signal and Tumor Accumulation of PVA-$^{19}$F-BPA
<Reagents, Cells, and Animals>
PVA was manufactured by the same method as in EXAMPLE 1 (Mn=6,500 to 9,500)
5 mol/l hydrochloric acid (for mass spectrometry): Wako Pure Chemical Industries, Ltd.

5 mol/l sodium hydroxide (for mass spectrometry): Wako Pure Chemical Industries, Ltd.
70% nitric acid (1.42): Wako Pure Chemical Industries, Ltd.
Disodium hydrogen phosphate: Nacalai Tesque
2-Amino-3-(4-borono-2-fluorophenyl) propanoic acid ($^{19}$F-BPA) (racemic): Fluorotech LLC CT26 cells (mouse colon cancer cell line): American Type Culture Collection (Manassas, Va.) BALB/c mouse: Charles River Japan
<Equipment>
NMR (Nuclear Magnetic Resonance): BRUKER AVANCE III 400 (400 MHz, BRUKER BioSpin)
Agilent 7900 ICP-MS: Agilent Technology Co., Ltd.

Figures 1, 10:
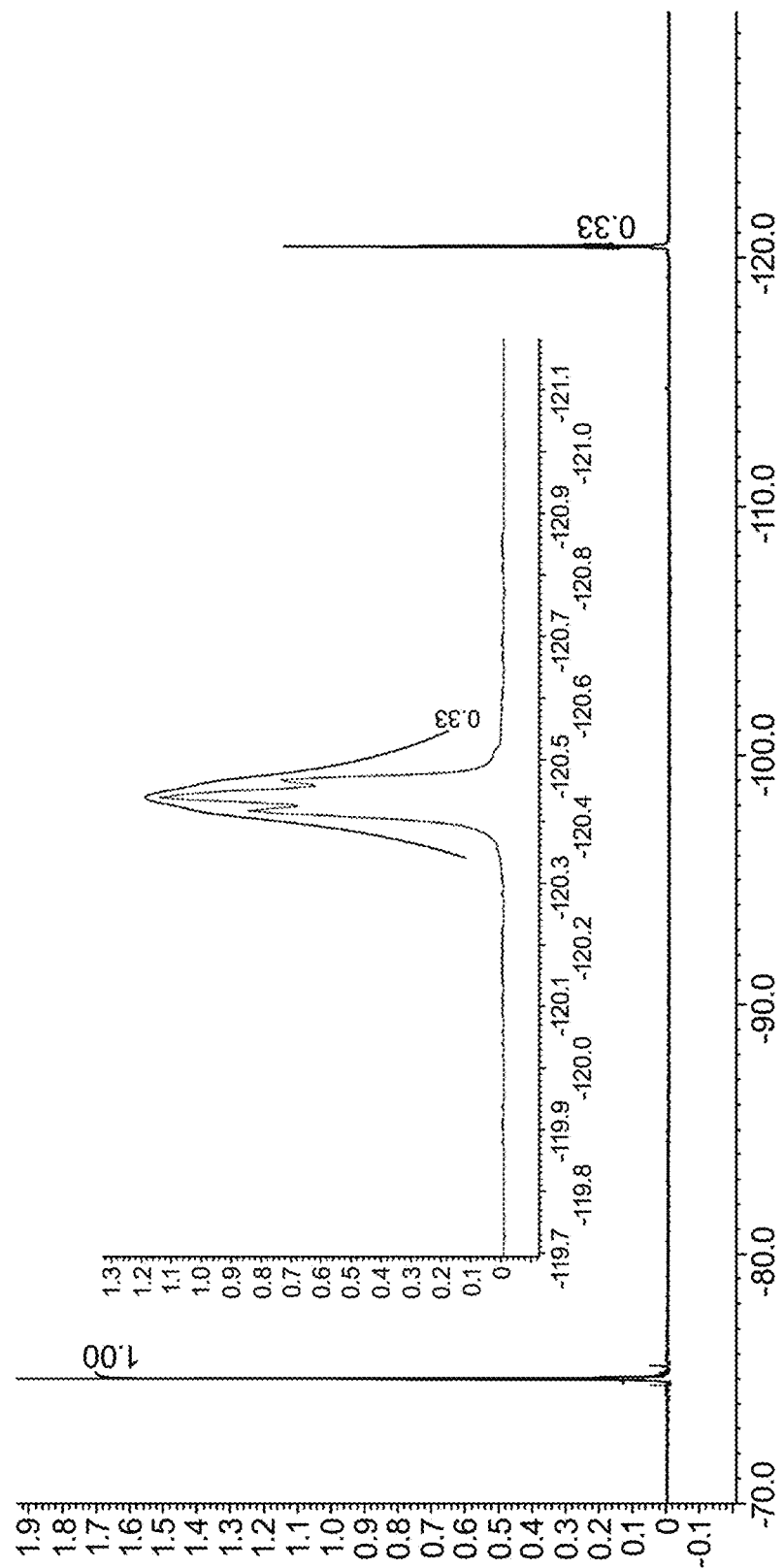
Figures 2, 10:
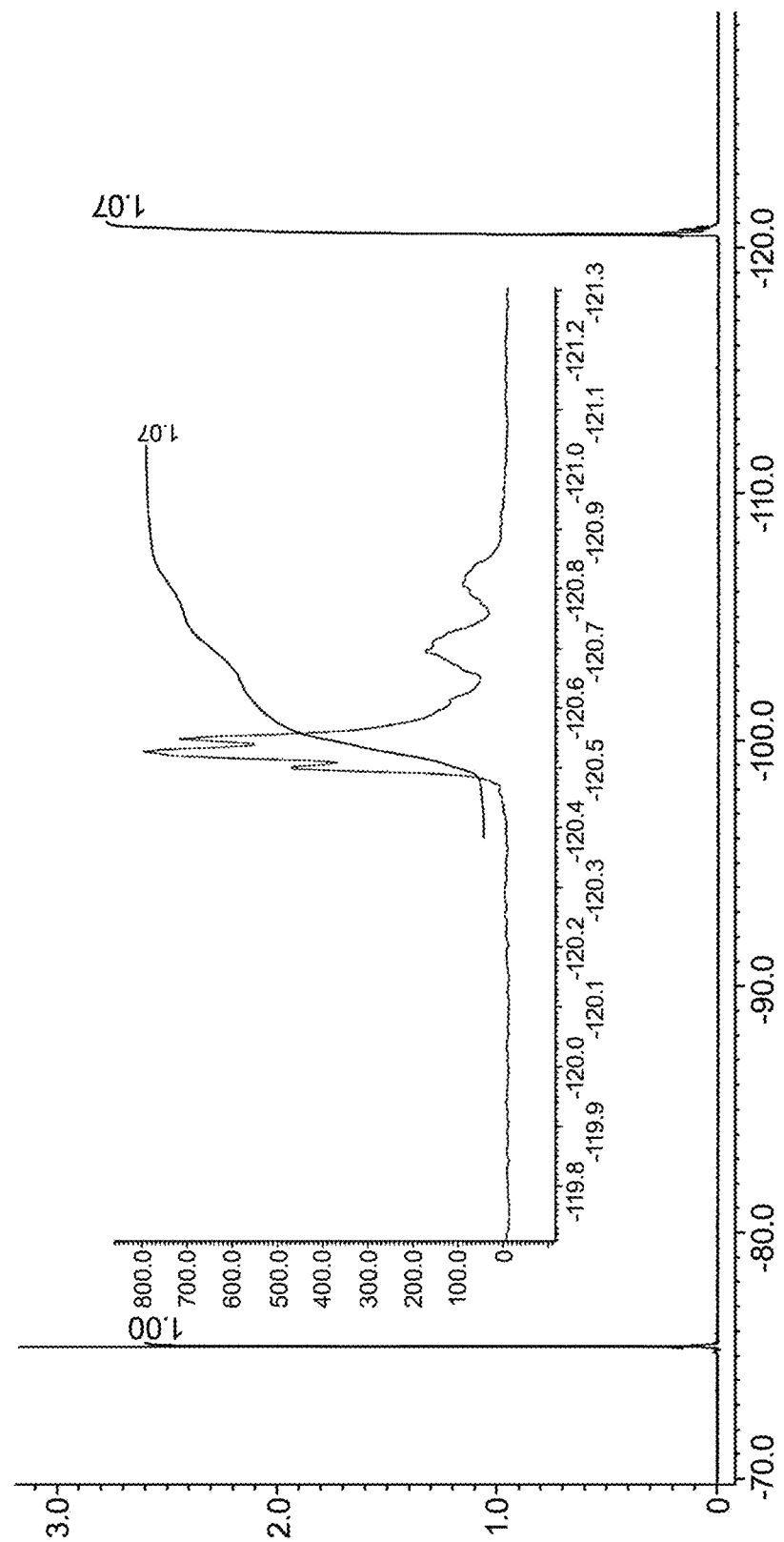
Figures 3, 10:
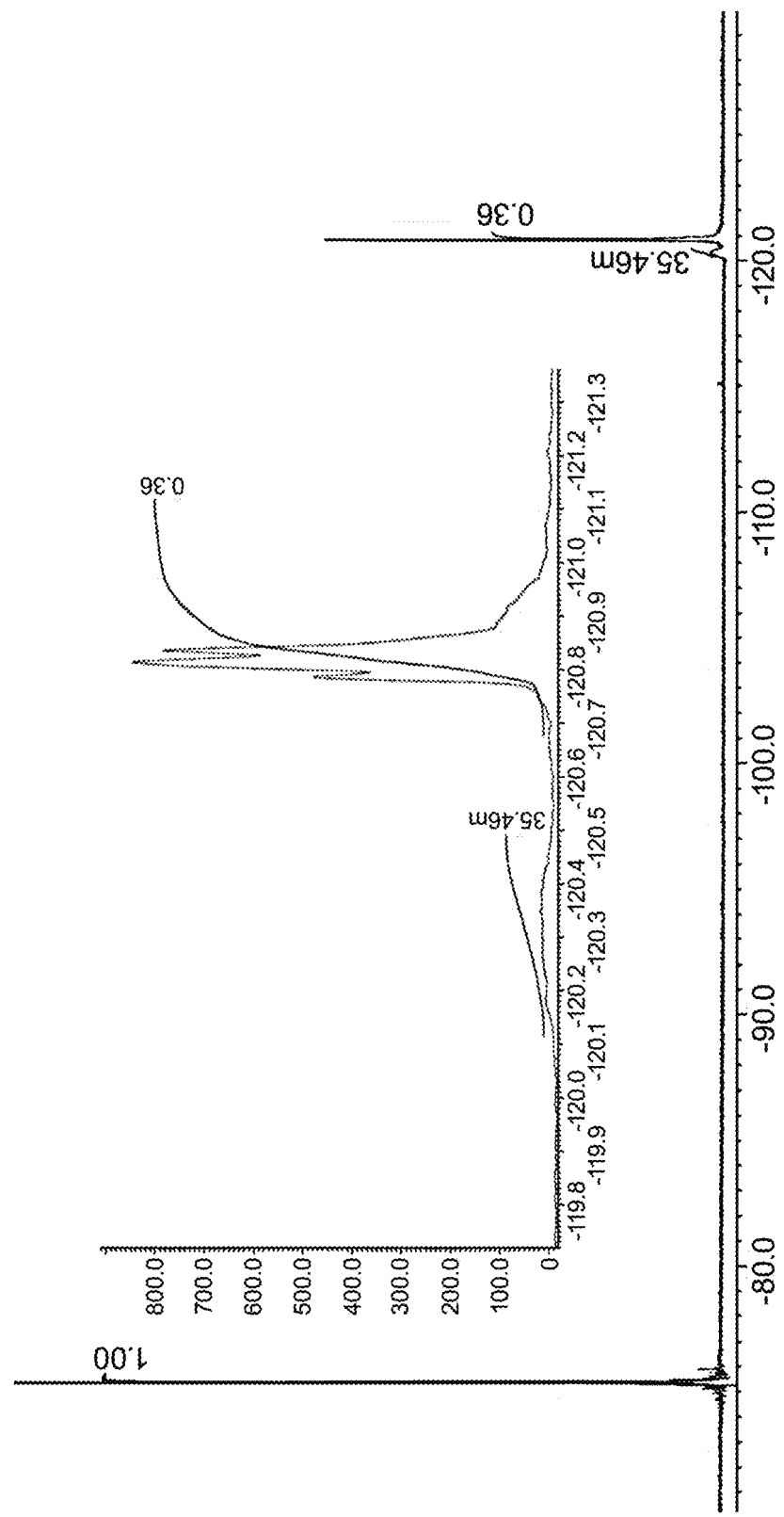

The following samples were prepared at the following concentrations using 10 mM PBS (140 mM NaCl, pH 9.5).
$^{19}$F-BPA ($^{19}$F-BPA concentration=176 mM)
Fru-$^{19}$F-BPA ($^{19}$F-BPA concentration=176 mM, fructose concentration=573.9 mM)
PVA-$^{19}$F-BPA ($^{19}$F-BPA concentration=176 mM, diol concentration in PVA=573.9 mM)
450 μL of each sample and 50 μL of $D_2O$ were mixed, and $^{19}$F-NMR was measured. The results are illustrated in FIGS. 10-1 to 10-3. The PVA-$^{19}$F-BPA NMR signal could be clearly detected (FIG. 10-3). It is considered that PVA-$^{19}$F-BPA is applicable to $^{19}$F-MRI in future diagnostic techniques.

Example 10

Pharmacokinetics of PVA-$^{19}$F-BPA and Fru-$^{19}$F-BPA

Subcutaneous tumor models were prepared by subcutaneously injecting CT26 cells into BALB/c mice at $2.0×10^5$ cells/mouse. Once the tumor size had reached about 200 mm$^3$, 200 L of the following samples were slowly administered through the tail vein of the mice ($^{19}$F-BPA 8 mg/mouse).
PVA-$^{19}$F-BPA (BPA concentration=176 mM, PVA diol concentration=574 mM) in PBS (pH 9.5)
Fru-$^{19}$F-BPA (BPA concentration=176 mM, fructose concentration=574 mM) in PBS (pH 9.5)

Figure 11:
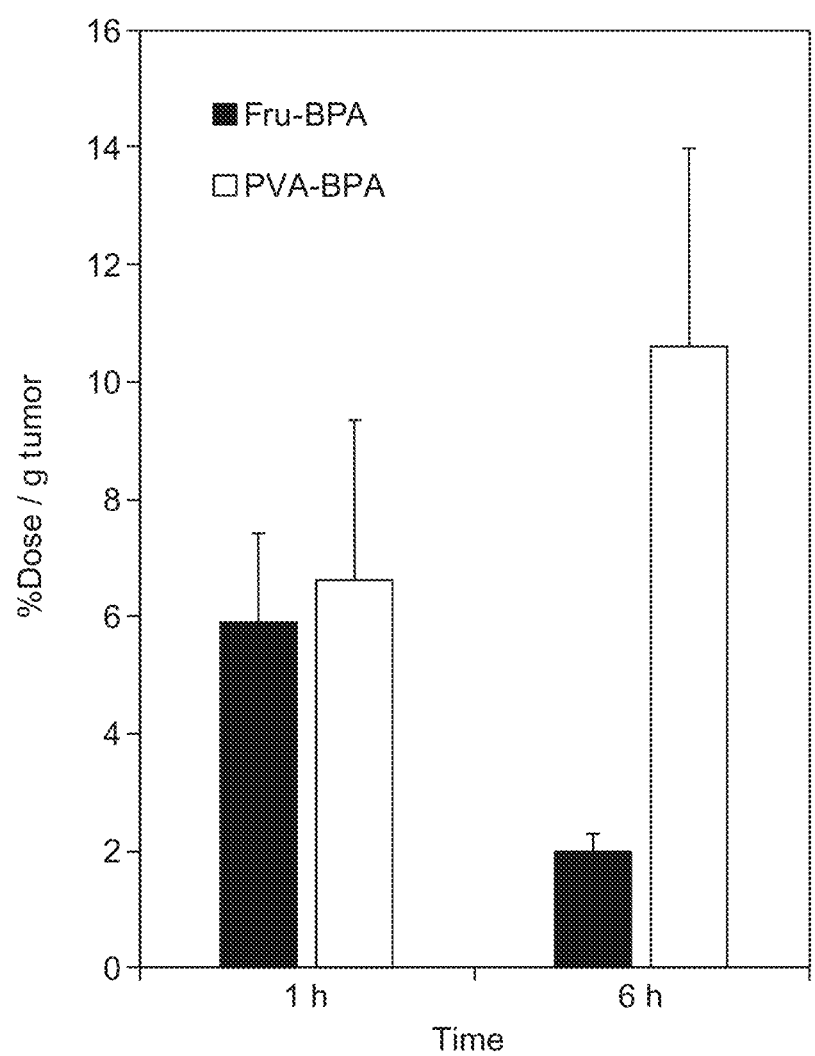
FIG. 11 shows the results of accumulation in tumors of PVA-$^{19}$F-BPA and Fru-$^{19}$F-BPA. In the figure, Fru-BPA represents the results for Fru-$^{19}$F-BPA and PVA-BPA represents the results for PVA-$^{19}$F-BPA.

After a predetermined time from administration of the sample, the mice were dissected and the tumors were removed. The tumors were placed in a 10 mL falcon tube, and 1 mL of 70% nitric acid was added thereto. Thereafter, each sample was incubated at 50° C. for 15 minutes, 70° C. for 15 minutes, and 90° C. for 1 hour. The samples were diluted to 10 mL with pure water, filtered through a hydrophobic filter, then the amount of boron was quantified using ICP-MS. The results are illustrated in FIG. 11. Since PVA-$^{19}$F-BPA is retained in the tumor at a high concentration for a long time, it is expected to improve the signal/noise ratio in $^{19}$F-MRI.

Example 11

Synthesis of PEG-P [Lys (Fru)/Lys]
<Reagents>
Dimethyl sulfoxide (DMSO) (dehydrated with calcium hydride then distillation-purified): Wako Pure Chemical Industries, Ltd.
Lys (TFA)-NCA: Chuo Kasei Co., Ltd.
MeO-PEG-NH2 (PEG molecular weight: 10 KDa): NOF corporation
Methanol: Wako Pure Chemical Industries, Ltd.
NaOH: Wako Pure Chemical Industries, Ltd.
HCl: Wako Pure Chemical Industries, Ltd.
Benzene: Wako Pure Chemical Industries, Ltd.
Diethyl ether: Kanto Chemical Co.

2,3,4,5-di-O-isopropylidene-beta-D-fructopyranose (Di-OFru): Tokyo Chemical Industry Co., Ltd.
1,1'-Carbonyldiimidazole (CDI): Sigma-Aldrich
Trifluoroacetic acid (TFA): Wako Pure Chemical Industries, Ltd.
4-Borono-L-phenylalanine (BPA) (B): KatChem
<Equipment>
NMR (Nuclear Magnetic Resonance): BRUKER AVANCE III 400 (400 MHz, BRUKER BioSpin)
GPC (Gel Permeation Chromatography): JASCO Corporation
Column for measuring PEG-PLys (TFA): TSK-gel superAW3000, superAW4000, and superAWL-guard column (Tosoh Corporation)
Column for measuring PEG-PLys: Superdex 200 Increase 10/300 GL (GE Healthcare)
Detector: RI-2031

(1) Synthesis of MeO-PEG-PLys (TFA)

[Chem. 67]

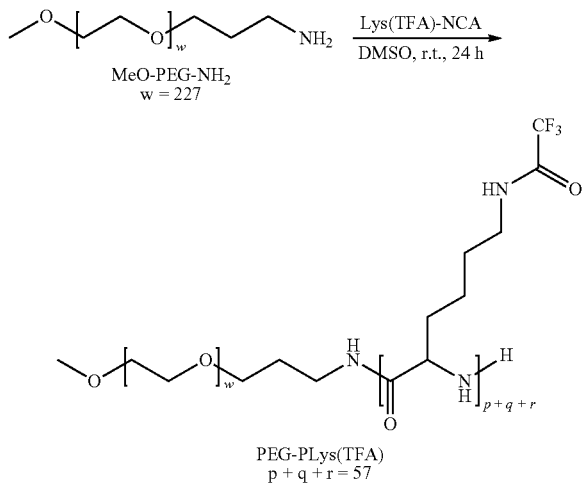

1.00 g of MeO-PEG-NH$_2$ was dissolved in benzene and freeze-dried overnight, this was then dissolved in 10 mL of distilled DMSO which was added thereto under an argon atmosphere. Meanwhile, 1.60 g of Lys(TFA)-NCA was dissolved in 15 mL distilled DMSO under an argon atmosphere. These solutions were mixed under an argon atmosphere and stirred for 24 hours at room temperature. Thereafter, the reaction solution was added to an excess amount of diethyl ether to generate a precipitate, which was collected by vacuum filtration and dried under reduced pressure overnight to obtain PEG-PLys (TFA). The molecular weight distribution of the obtained PEG-PLys (TFA) was confirmed by GPC and the Mw/Mn was 1.12. Further, the degree of polymerization of Plys (TFA) from the results of $^1$H-NMR was 57.

$^1$H-NMR (400 MHz, DMSO-d$_6$): δ9.48-9.10 (br, —NH—C=O—CF$_3$), 8.61-7.60 (br, C—NH—C=O—), 4.10-3.72 (br, CH—NH—), 3.70-3.45 (br, —CH2-CH2-O—), 3.25-3.00 (br, —CH2-NH—C=O—), 2.22-1.00 (br, CH2-CH2-CH2-)

(2) Synthesis of PEG-PLys

[Chem. 69]

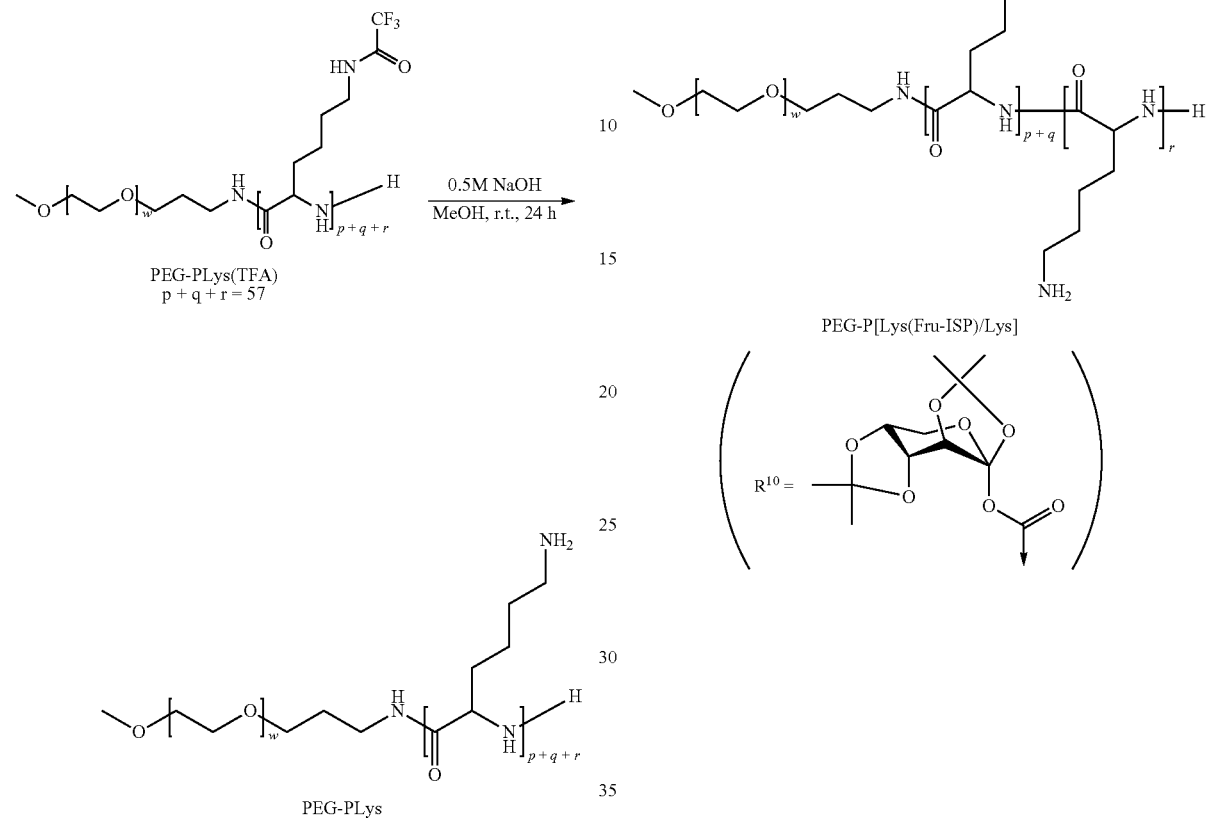

1.2 g of PEG-PLys (TFA) was dissolved in a mixture of aqueous NaOH solution (5M)/water/methanol (10 mL/5 mL/35 mL) and stirred for 20 hours at 35° C. This was then dialyzed twice against 0.01 N HCl and three times against pure water (MWCO of dialysis membrane: 6 to 8 kDa). This was then freeze-dried and 600 mg of PEG-PLys was obtained.

[Chem. 70]

$^1$H-NMR (400 MHz, D$_2$O): δ 4.43-4.24 (br, CH—NH—), 3.85-3.61 (br, —CH2-CH2-O—), 2.07-1.28 (br, —CH2-CH2-CH2-), 3.14-2.94 (br, —CH2-NH—C=O—)

(3) Synthesis of PEG-P [Lys (Fru-ISP)/Lys]

[Chem. 71]

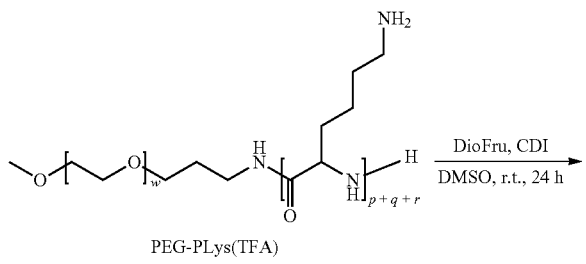

1.21 g of CDI and 3.88 g of DiOfru was dissolved in 15 mL of distilled DMSO under an argon atmosphere and stirred for 20 hours at 45° C. Next, 300 mg of MeO-PEG-PLys was dissolved in 5 mL of distilled DMSO, a solution obtained by reacting CDI and DiOFru was added thereto, and this was allowed to react for 20 hours at room temperature. After the reaction, dialysis was then performed thereon twice against methanol and twice against pure water (MWCO of dialysis membrane: 6 to 8 kDa). Finally, this was freeze-dried and 360 mg of PEG-P[Lys(Fru ISP)/Lys] was obtained. The molecular weight distribution thereof was measured by GPC and the Mw/Mn=1.17. The rate of introduction of DiOFru into a polymer was 58% as calculated by $^1$H-NMR. From the results of $^1$H-NMR, (p+q) was 33 and r was 24 in the above chemical formula.

[Chem. 72]

$^1$H-NMR (400 MHz, D$_2$O): δ 3.85-3.61 (br, —CH2-CH2-O—), 3.32-3.02 (br, —CH2-NH—R$^{10}$), 3.02-2.81 (br, —CH2-NH2), 2.25-1.20 (br, —CH2-CH2-CH2-, CH3-C—CH3)

(4) Synthesis of PEG-P [Lys (Fru)/Lys]

[Chem. 73]

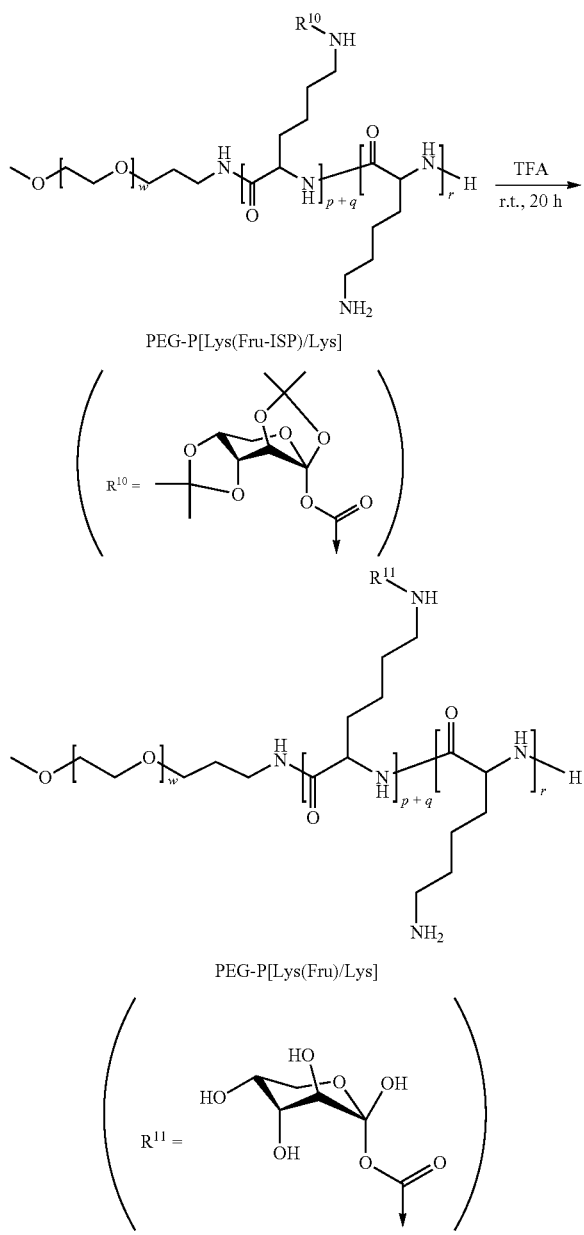

PEG-P [Lys (Fru-ISP)/Lys] was dissolved in TFA/H$_2$O (95/5 v/v) at 20 mg/mL and stirred overnight at room temperature. The reaction solution was then dialyzed once against pure water, twice against 0.01 N HCL, and a further twice against pure water (MWCO of dialysis membrane: 6k to 8 kDa). After dialysis, this was freeze-dried and PEG-P [Lys(Fru)/Lys] was obtained. Mn=24,100.

[Chem. 74]

$^1$H-NMR (400 MHz, D$_2$O): δ 4.35-4.20 (br, —CH—NH—), 3.75-3.55 (br, —CH2- CH2-O—), 3.32-3.02 (br, —CH2-NH—R$^{11}$), 3.02-2.81 (br, —CH2-NH2), 1.98-1.15 (br, —CH2-CH2-, CH2-)

Example 12

Figures 1, 12:
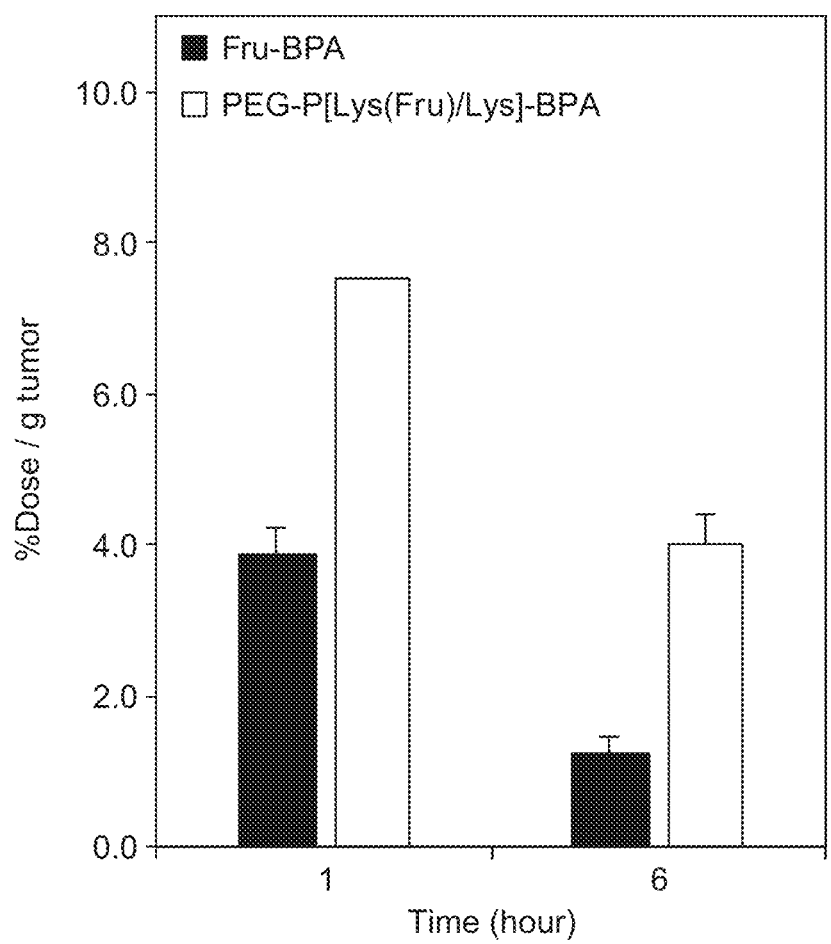
Figures 2, 12:
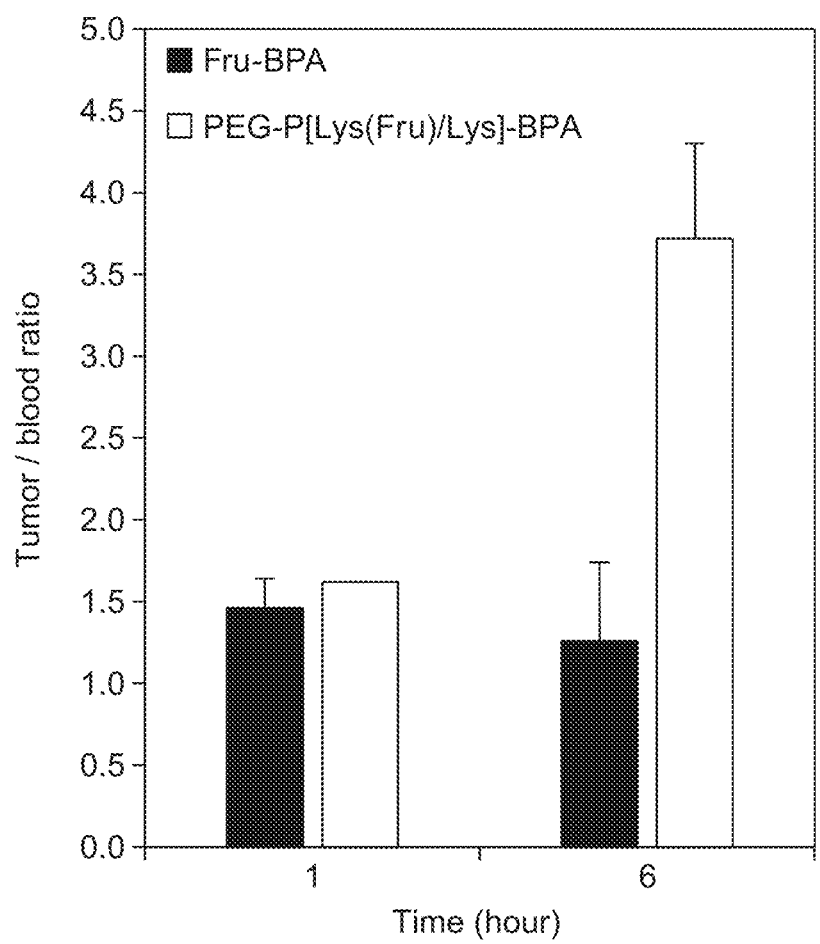

Evaluation of Tumor Accumulation and Antitumor Effect of BPA Derivative (PEG-P [Lys (Fru)/Lys]-BPA) in which BPA is Bound to PEG-P[Lys(Fru)/Lys]
<Reagents, Cells, and Animals>
PEG-P [Lys(Fru)/Lys] was manufactured by the same method as in EXAMPLE 11 (Mn=24,100)
5 mol/l hydrochloric acid (for mass spectrometry): Wako Pure Chemical Industries, Ltd.
5 mol/l sodium hydroxide (for mass spectrometry): Wako Pure Chemical Industries, Ltd.
4-Borono-L-phenylalanine (BPA): Katchem
Disodium hydrogen phosphate: Nacalai Tesque
BxPC3 cells (human pancreatic cancer cell line): American Type Culture Collection (Manassas, Va.)
CT26 cells (mouse colon cancer cell line): American Type Culture Collection (Manassas, Va.)
BALB/c mouse: Charles River Japan
BALB/c nude mouse: Charles River Japan
<Equipment>
Agilent 7900 ICP-MS: Agilent Technology Co., Ltd.
Heavy Water Neutron Irradiation Facility: KUR
BxPC3 cells were subcutaneously injected into BALB/c nude mice at 1×10$^7$ cells/mouse. Once the tumor size had reached about 200 mm$^3$, the following sample was intravenously injected.
PEG-P[Lys(Fru)/Lys]-BPA in PBS (33 mg PEG-P[Lys (Fru)/Lys]/mouse, 8 mg BPA/mouse)
After a predetermined time from administration of the sample, the mice were dissected, blood was collected, and the tumors were removed. The tumors were placed in a 10 mL falcon tube, and 1 mL of 70% nitric acid was added. Thereafter, each sample was incubated at 50° C. for 15 minutes, 70° C. for 15 minutes, and 90° C. for 1 hour. The samples were diluted to 10 mL with pure water, filtered through a hydrophobic filter, then the amount of boron was quantified using ICP-MS. The results are illustrated in FIGS. 12-1 and 12-2.

Example 13

Antitumor Effects of PEG-P[Lys(Fru)/Lys]-BPA on CT26 Subcutaneous Tumor Model
CT-26 cells were subcutaneously implanted (2.0×10$^5$ cells/mouse) near the right thigh of BALB/c mice, and 250 μL of the following samples were slowly administered through the tail vein of mice with a tumor size of about 15 to 150 mm$^3$ (BPA 10 mg/mouse).
Fru-BPA (BPA concentration=192 mM, fructose concentration:BPA concentration=3:1) in PBS (pH 8.5)
PEG-P[Lys(Fru)/Lys]-BPA (BPA concentration=192 mM, polymer side chain fructose concentration:BPA concentration=1.2:1) in PBS (pH 8.5)
In the neutron irradiation group, neutron irradiation was performed for 50 minutes only around the right thigh of the mouse 3 hours and 6 hours after the sample administration. With the day of irradiation set as the first day, the tumor diameter was measured every 2 to 3 days with electronic calipers and the body weight was measured with an electronic balance for a total of 25 days. The measured tumor diameter was used in an elliptic volume approximation formula (ab$^2$×½, where a is the long side and b is the short side) to give the tumor volume. The evaluated groups are summarized below.

Control (COLD) (n=7): untreated group.
Fru-BPA (COLD) (n=7): injected with only Fru-BPA.
PEG-P[Lys(Fru)/Lys]-BPA (COLD) (n=4): injected with only PEG-P[Lys(Fru)/Lys]-BPA.
Control (HOT) (n=6): only irradiated with neutrons.
Fru-BPA (HOT) 3h (n=7): injected with Fru-BPA then irradiated with neutrons 3 hours thereafter.
Fru-BPA (HOT) 6h (n=7): injected with Fru-BPA then irradiated with neutrons 6 hours thereafter.
PEG-P[Lys(Fru)/Lys]-BPA (HOT) 3h (n=6): injected with PEG-P[Lys(Fru)/Lys]-BPA then irradiated with neutrons 3 hours thereafter.
PEG-P[Lys(Fru)/Lys]-BPA (HOT) 6h (n=5): injected with PEG-P[Lys(Fru)/Lys]-BPA then irradiated with neutrons 6 hours thereafter.

Figures 1, 13:
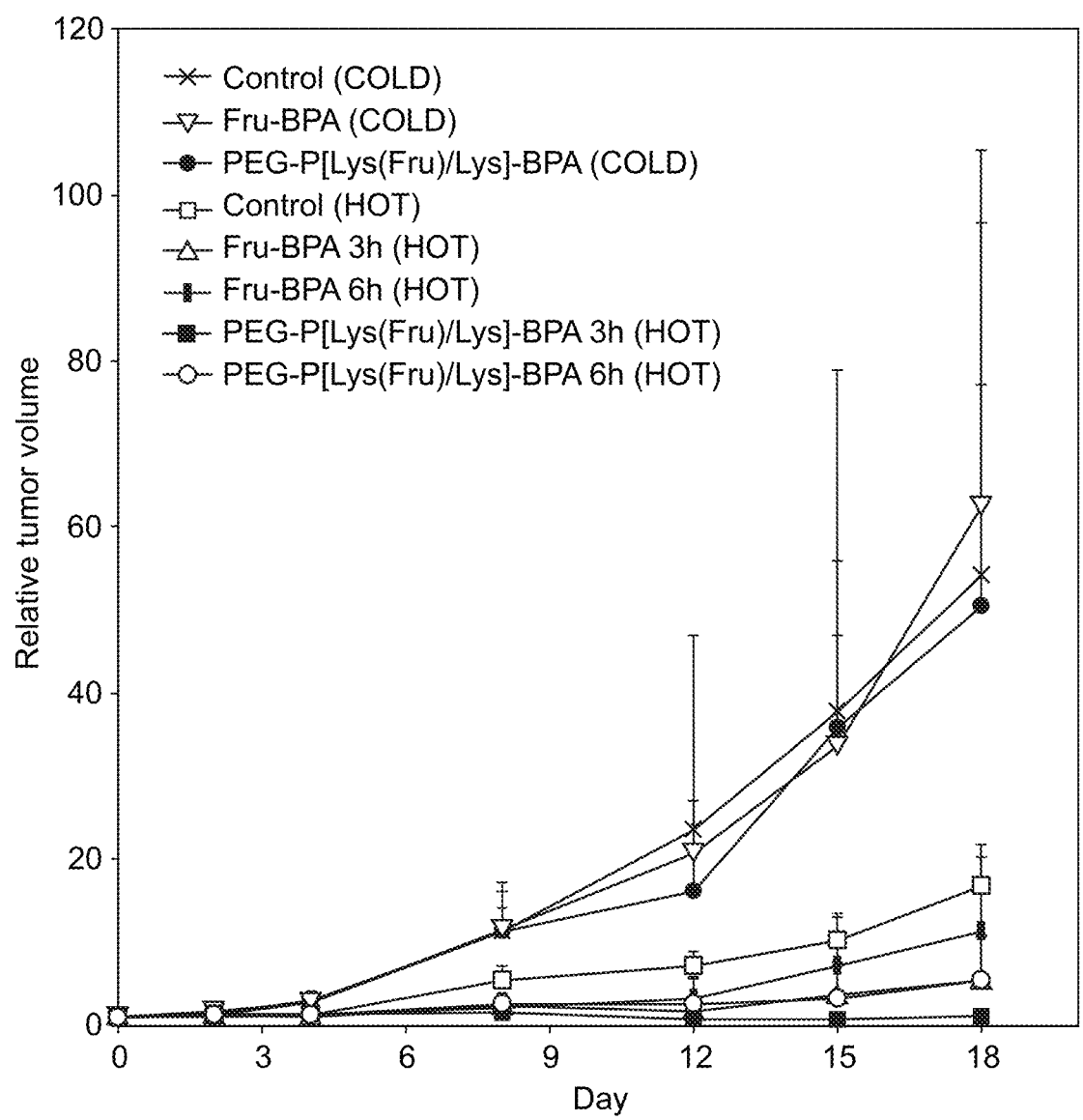
Figures 2, 13:
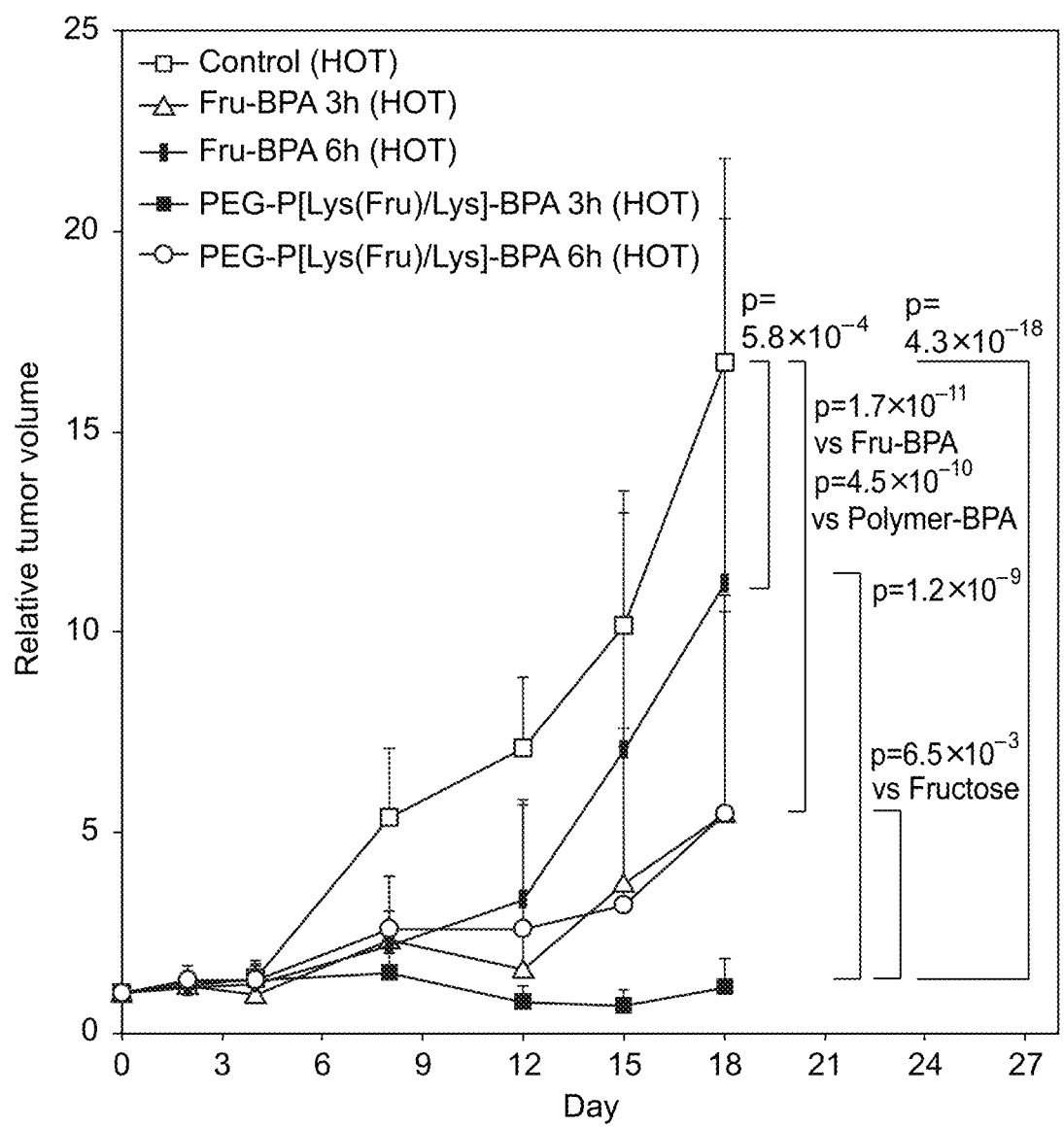

The change in tumor size over time is shown in FIGS. 13-1 and 13-2. PEG-P[Lys(Fru)/Lys]-BPA showed a significant inhibitory effect on tumor growth in neutron capture therapy compared to Fru-BPA.

Example 14

Synthesis of P[Asp(glucamine)/Asp]

<Reagents>
Dimethyl sulfoxide (DMSO) (dehydrated with calcium hydride and distillation-purified): Wako Pure Chemical Industries, Ltd.
BLA-NCA: NanoCarrier Co., Ltd.
4-(4,6-dimethoxy-1,3,5-triazin-2-yl)-4-methylmorpholinium chloride (DMTMM): Wako Pure Chemical Industries, Ltd.
Triethylamine (TEA): Wako Pure Chemical Industries, Ltd.
Diethyl ether: Kanto Chemical Co.
Methanol: Wako Pure Chemical Industries, Ltd.
NaOH: Wako Pure Chemical Industries, Ltd.
HCl: Wako Pure Chemical Industries, Ltd.
N,N-dimethylformamide (DMF): Wako Pure Chemical Industries, Ltd. (used after dehydration distillation)
Dichloromethane (DCM): Wako Pure Chemical Industries, Ltd. (used after dehydration distillation)
4-Borono-L-phenylalanine (BPA) (B): KatChem
D-glucamine: Tokyo Chemical Industry Co., Ltd.
<Equipment>
NMR (Nuclear Magnetic Resonance): BRUKER AVANCE III 400 (400 MHz, BRUKER BioSpin)
GPC (Gel Permeation Chromatography): JASCO Corporation
Column for measuring PBLA: TSK-gel super AW3000, super AW4000, and super AWL-guard column (Tosoh Corporation)
Column for measuring PAsp: Superdex 200 Increase 10/300 GL (GE Healthcare) Detector: UV-2070 (Ch. 1), RI-2031 (Ch.2)

(1) Production of poly (O-benzyl-L-aspartate) (PBLA)

[Chem. 75]

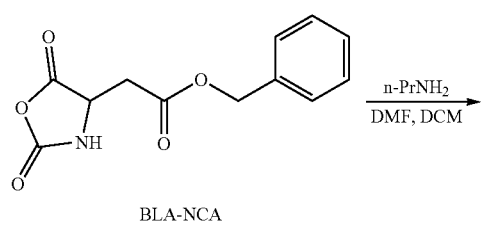

BLA-NCA

-continued

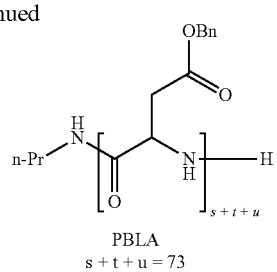

PBLA
s + t + u = 73

1.44 g of BLA-NCA was dissolved in a mixed solvent of 3 mL of DMF and 27 mL of DCM under an argon atmosphere, 3.9 µL of propylamine was added thereto and stirring was performed for 48 hours. After stirring, the reaction solution was added dropwise to diethyl ether to obtain a precipitate which was suction filtered and dried under reduced pressure to obtain PBLA. The molecular weight distribution was determined to be Mw/Mn=1.11 by GPC, and the degree of polymerization was 73 from the result of $^1$H-NMR.

[Chem. 76]

$^1$H-NMR (400 MHz, DMSO-d6): δ 8.35-8.00 (br, —C—NH—C=O—), 7.40-7.19 (br, —C6H5), 5.15-4.92 (br, —O-CH2-C6H5), 4.70-4.51 (br, CH—NH—), 2.90-2.49 (br, CH—CH2-C=O—O—), 0.78-0.71 (br, —CH3)

(2) Production of Polyaspartic Acid (PAsp)

[Chem. 77]

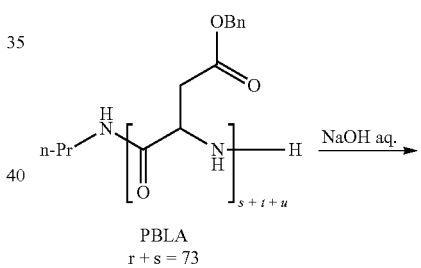

PBLA
r + s = 73

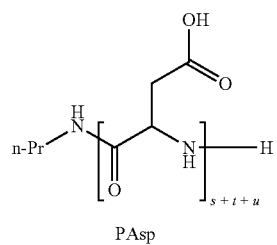

PAsp 1 g of PBLA was added to a 0.5 M aqueous NaOH solution and stirred for 20 hours at 35° C. The reaction solution was dialyzed against pure water four times (dialysis membrane MWCO: 3.5 kDa) and freeze-dried to obtain 0.2 g of PAsp.

[Chem. 78]

$^1$H-NMR (400 MHz, D$_2$O): δ 2.91-2.48 (br, —C-CH2-COOH), 0.94-0.82 (br, —CH3)

(3) Production of P[Asp(glucamine)/Asp]

[Chem. 79]

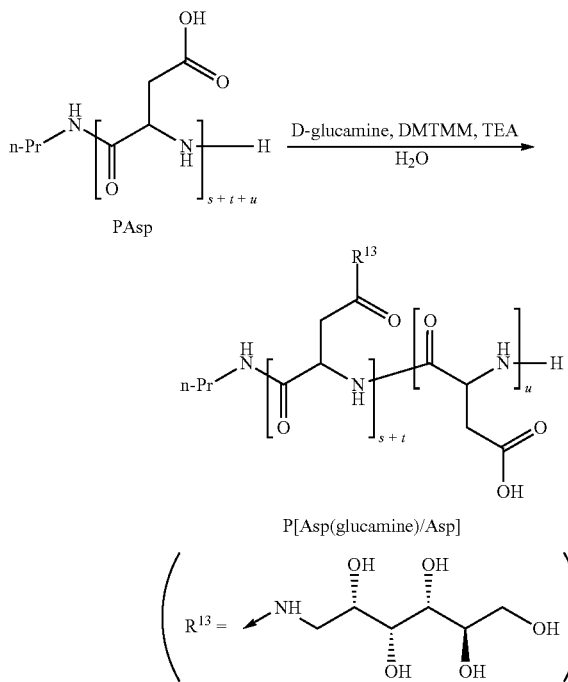

0.2 g of PAsp, 3 g of DMTMM, and 2.6 g of D-glucamine were dissolved in pure water, a few drops of TEA were added, and the mixture was stirred at room temperature for 24 hours. After stirring, the reaction solution was dialyzed against pure water four times (dialysis membrane MWCO: 3.5 kDa) and freeze-dried to obtain P[Asp(glucamine)/Asp]. The physical properties were evaluated by GPC and $^1$H-NMR, and the $^1$H-NMR result showed that the introduction rate of glucamine was 30%. From the results of $^1$H-NMR, (s+t) was 17 and u was 56 in the above chemical formula.

[Chem. 80]

$^1$H-NMR (400 MHz, $D_2O$): δ 4.18-3.00 (br, —$R^{11}$), 2.91-2.48 (br, —CH—CH2-COOH), 0.94-0.82 (br, —CH3)

Example 15

Tumor Accumulation of BPA Derivative (P[Asp(Glucamine)/Asp]-BPA) in which BPA is Bound to P[Asp(glucamine)/Asp]

Subcutaneous tumor models were prepared by subcutaneously injecting CT26 cells into BALB/c mice at $2.0 \times 10^5$ cells/mouse. Once the tumor size had reached about 200 mm$^3$, 200 µL of the following sample was slowly administered through the tail vein of the mice (BPA 8 mg/mouse).

P[Asp(glucamine)/Asp]-BPA (BPA concentration=192 mM, BPA concentration:glucamine concentration=1:1.2) in PBS (pH 9)

Figures 1, 14:
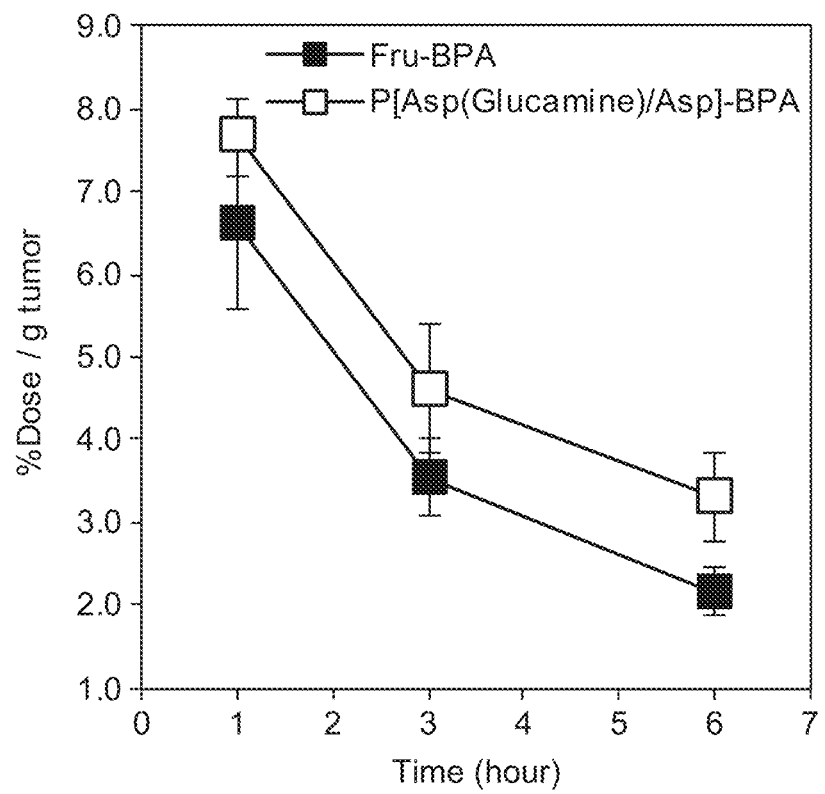
Figures 2, 14:
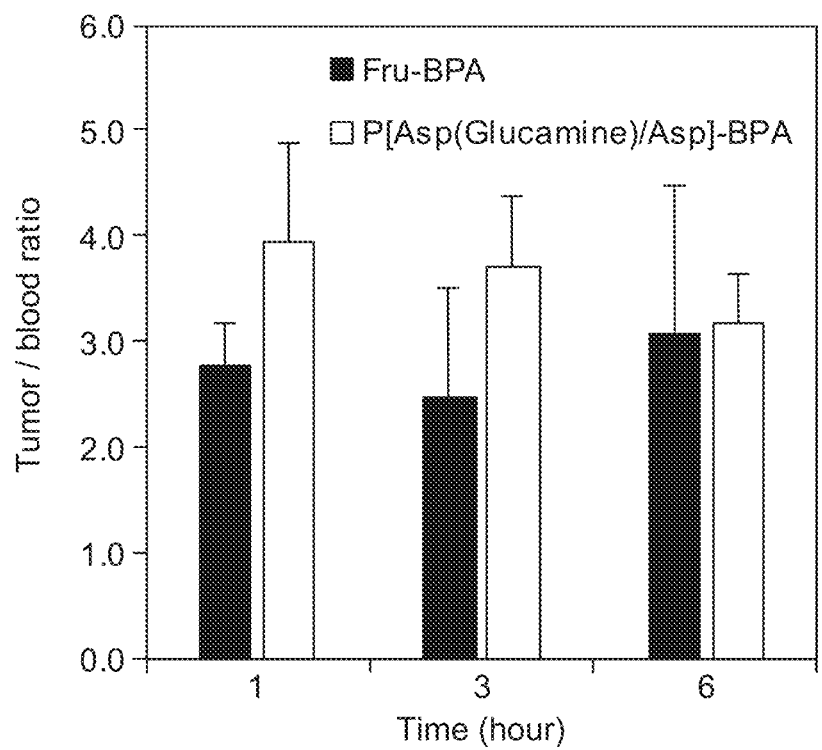

After a predetermined time from administration of the sample, blood was collected, the mice were dissected, and the tumors were removed. The tumors were placed in a 10 mL falcon tube, and 1 mL of 70% nitric acid was added thereto. Thereafter, each sample was incubated at 50° C. for 15 minutes, 70° C. for 15 minutes, and 90° C. for 1 hour. The samples were diluted to 10 mL with pure water, filtered through a hydrophobic filter, then the amount of boron was quantified using ICP-MS. The results are illustrated in FIGS. 14-1 and 14-2 and suggest that the use of P[Asp(glucamine)/Asp]-BPA may improve accumulation properties in the tumor and the tumor/blood accumulation ratio.

Example 16

Antitumor Effects of PVA-BPA on BxPC3 Subcutaneous Tumor Model

BxPC3 cells were subcutaneously injected ($5 \times 10^6$ cells/mouse) near the right thigh of BALB/c mice, and 250 µL of the following samples were slowly administered through the tail vein of mice with a tumor size of about 500 mm$^3$ (BPA 10 mg/mouse).

PVA-BPA (BPA concentration=191 mM, PVA diol concentration=574 mM) in water (pH 9.2)

Fru-BPA (BPA concentration=191 mM, fructose concentration=574 mM) in water (pH 9.2)

(The pH was adjusted using aqueous HCl solution and aqueous NaOH solution.)

Neutron irradiation was performed for 50 minutes only around the right thigh of the mouse 3 hours after sample administration. With the day of irradiation set as the first day, the tumor diameter was measured over time with electronic calipers and the body weight was measured with an electronic balance for a total of 55 days. The measured tumor diameter was used in an elliptic volume approximation formula (ab$^2$×½, where a is the long side and b is the short side) to give the tumor volume. The evaluated groups are summarized below.

Control (COLD) (n=8): untreated group.
Fru-BPA (HOT) (n=6): injected with Fru-BPA then irradiated with neutrons 3 hours thereafter.
PVA-BPA (HOT) (n=6): injected with PVA-BPA then irradiated with neutrons 3 hours thereafter.

Figure 15:
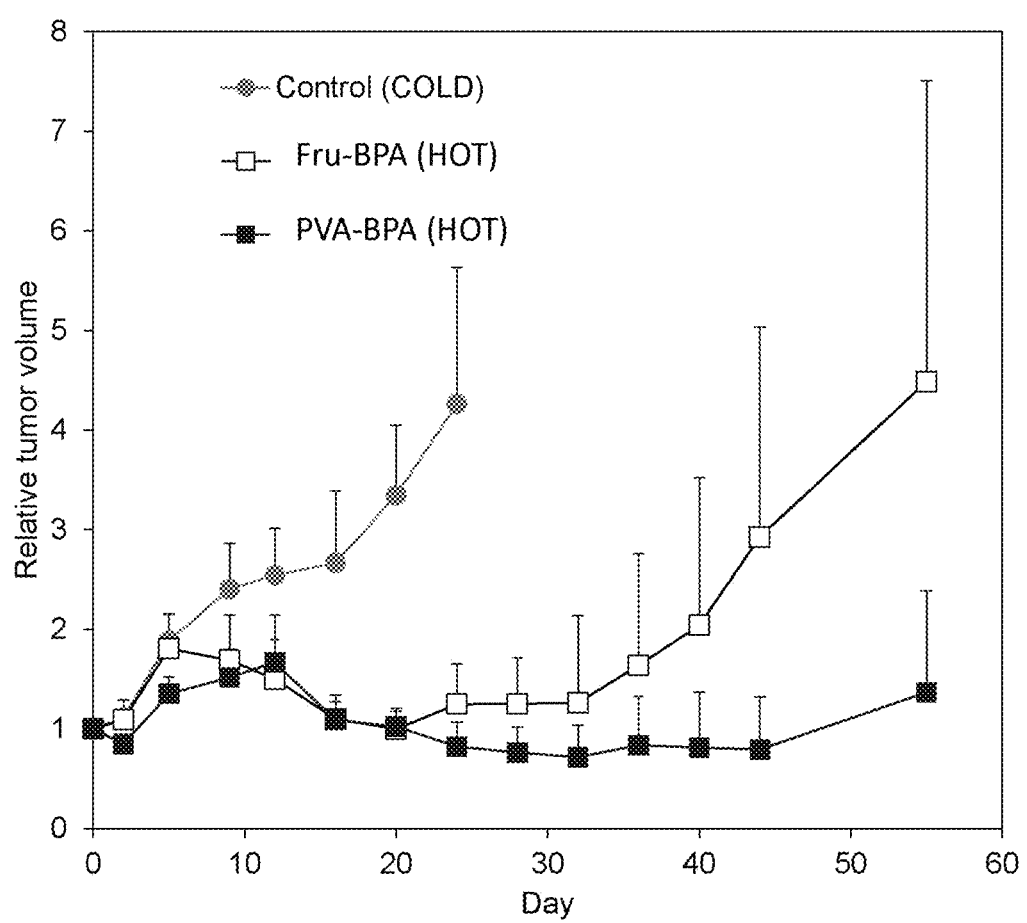
FIG. 15 shows the relative change in size of tumors over time after administration of the samples. The data is shown as mean±S.D. (Control: n=8, fructose-BPA: n=6, PVA-BPA: n=6).

The results are illustrated in FIG. 15. On the 55th day, there was a statistically significant difference between Fru-BPA and PVA-BPA (p<0.05 [t-test]).

Example 17

Antitumor Effects of PEG-P[Lys(Fru)/Lys]-BPA on BxPC3 Subcutaneous Tumor Model

BxPC3 cells were subcutaneously injected ($5 \times 10^6$ cells/mouse) near the right thigh of BALB/c mice, and 250 µL of the following samples were slowly administered through the tail vein of mice with a tumor size of about 15 to 150 mm$^3$ (BPA 10 mg/mouse).

Fru-BPA (BPA concentration=192 mM, fructose concentration:BPA concentration=3:1) in PBS (pH 8.5)

PEG-P[Lys(Fru)/Lys]-BPA (BPA concentration=192 mM, polymer side chain fructose concentration:BPA concentration=1.2:1) in PBS (pH 8.5)

In the neutron irradiation group, neutron irradiation was performed for 50 minutes only around the right thigh of the mouse 3 hours and 6 hours after the sample administration. With the day of irradiation set as the first day, the tumor diameter was measured every 2 to 3 days with electronic calipers and the body weight was measured with an electronic balance for a total of 25 days. The measured tumor diameter was used in an elliptic volume approximation formula (ab$^2$×½, where a is the long side and b is the short side) to give the tumor volume. The evaluated groups are summarized below.

Control (HOT) (n=8): only irradiated with neutrons.

Fru-BPA (HOT) (n=8): injected with Fru-BPA then irradiated with neutrons 3 hours thereafter.

PEG-P[Lys(Fru)/Lys]-BPA (HOT) (n=8): injected with PEG-P[Lys(Fru)/Lys]-BPA then irradiated with neutrons 3 hours thereafter.

Figure 16:
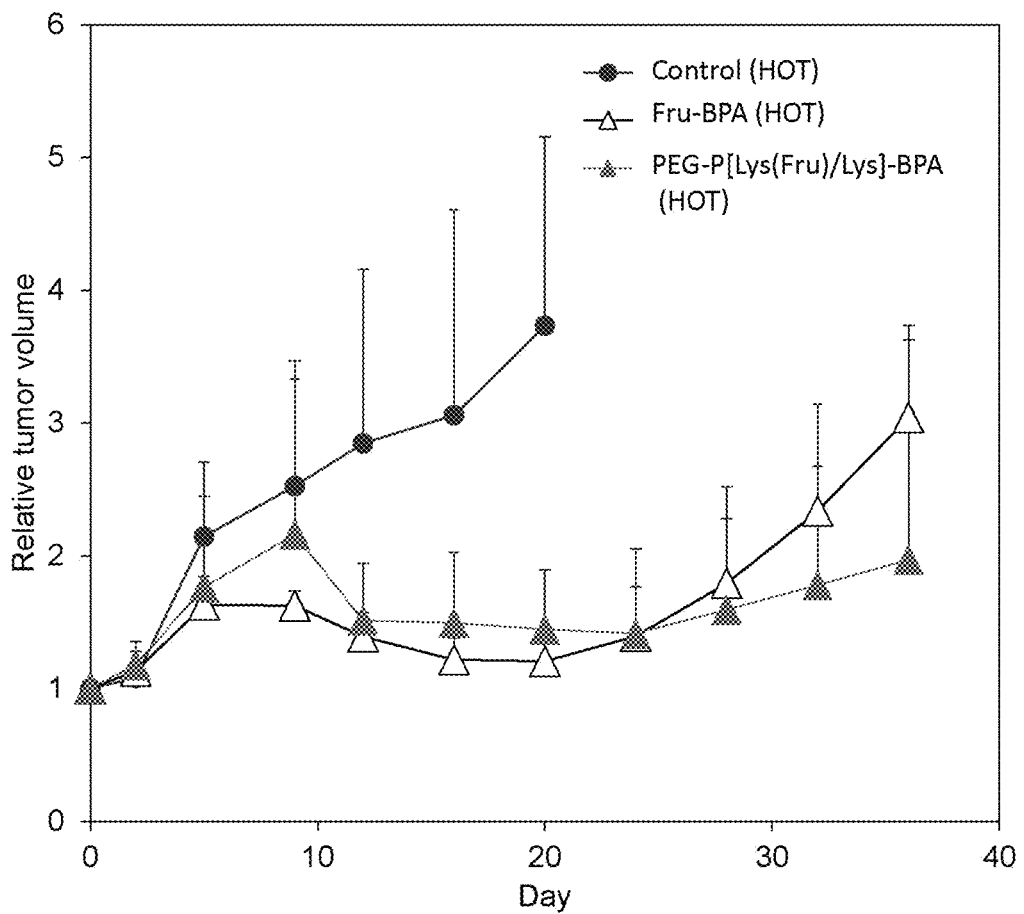
FIG. 16 shows the relative change in size of tumors over time after administration of the samples. The data is shown as mean±S.D. (n=8).

The change in tumor size over time is shown in FIG. 16.

Example 18

Synthesis of $N_3$—P[Lys(Gluconate)/Lys] and mPEG10k-P[Lys(Gluconate)/Lys]

[Chem. 81]

$N_3$-PLys(A): R = $N_3$; (x + y + z) = ; 64.4
$N_3$-PLys(B): R = $N_3$; (x + y + z) = ; 98.4
$N_3$-PLys(C): R = $N_3$; (x + y + z) = ; 130.4
mPEG10k-PLys: R = mPEG10k; (x + y + z) = 52.1

$N_3$-P[Lys(Gluconate/Lys] (A): R = $N_3$; (x + y) = ; 63.1
$N_3$-P[Lys(Gluconate/Lys] (B): R = $N_3$; (x + y) = ; 96.8
$N_3$-P[Lys(Gluconate/Lys] (C): R = $N_3$; (x + y) = ; 127.5
mPEG10k-P[Lys(Gluconate/Lys]: R = mPEG10k; (x + y) = 51.5

<Reagents>
11-Azide-3,6,9-trioxaundecane-1-amine: Sigma Aldrich
Methoxy-PEG$_{10k}$-NH$_2$: NOF Co.
NCA-L-Lys(Tfa): Chuo Kasei Co.
D-glucono-1,5-lactone: Tokyo Chemical Industry Co.
Triethylamine (TEA): Nacalai Tesque
Dimethyl sulfoxide (DMSO): DMSO purchase from Wako Pure Chemical Industries, Ltd., was distillation-purified under an argon atmosphere and used.
Methanol: Wako Pure Chemical Industries, Ltd.
Benzene: Nacalai Tesque
Diethyl ether: Kanto Chemical Co.
5 mol/L aqueous sodium hydroxide solution: Wako Pure Chemical Industries, Ltd.
5 mol/L hydrochloric acid: Nacalai Tesque
Heavy water (0.05% by weight 3-(trimethylsilyl)propionic-2,2,3,3-d$_4$ acid, sodium salt:Sigma Aldrich
<Equipment>
NMR (Nuclear Magnetic Resonance): BRUKER AVANCE III 400 (400 MHz, BRUKER BioSpin)
GPC (Gel Permeation chromatography): JASCO Corporation
Superdex 200 Increase 10/300 GL (GE Healthcare)
Detector: RI-2031
(1-1)
Synthesis of $N_3$-Plys_(A)

3.2 g (11.9 mmol) of NCA-Lys(Tfa) was weighed and added to a 100 mL two-necked pear-shaped flask under an argon atmosphere. 33 mL of distillation-purified DMSO was added thereto and NCA was dissolved. Thereafter, 30 µL (0.151 mmol) of the initiator 11-azide-3,6,9-trioxaundecane-1-amine was added, and the mixture was stirred in a water bath at 40° C. for 3 days. Thereafter, the reaction solution was put into a dialysis membrane (MWCO=3.5 kD) and dialyzed 3 times against 500 mL of methanol for 4 hours. The solvent was evaporated from the dialyzed sample solution with a rotary evaporator and then dried under reduced pressure overnight. 100 mL of methanol, 2 mL of 5 M aqueous sodium hydroxide solution, and 8 mL of ultrapure water were added to the obtained solid matter which was dissolved. This was stirred overnight in a 40° C. water bath. Thereafter, the reaction solution was put into a dialysis membrane (MWCO=3.5 kD) and dialyzed twice against a 1 L 0.01 M aqueous sodium hydroxide solution for 4 hours and then dialyzed four times against 3 L of ultrapure water for 4 hours. The dialyzed sample was placed in a 500-mL pear-shaped flask, and the solvent was removed by freeze drying to obtain a white solid of $N_3$-PLys_(A). From $^1$H-NMR, the degree of polymerization of the obtained compound was 64.4.

[Chem. 82]

$^1$H NMR (400 MHz, $D_2O$): δ 1.35-1.90 (br, —$CH_2$—), 3.02 (t, —$CH_2$—$NH_2$), 3.70 (br, —$CH_2$—O—), 4.32 (t, —CH—CONH—).

(1-2)

(2) Synthesis of $N_3$-Plys_(B)

By performing a reaction using the same method as in (1-1) above other than using 20 μL (0.101 mmol) of the initiator 11-azide-3,6,9-trioxaundecane-1-amine, a white solid of $N_3$-PLys_(B) was obtained. From $^1$H-NMR, the degree of polymerization of the obtained compound was 98.4.

[Chem. 83]

$^1$H NMR (400 MHz, $D_2O$): δ 1.35-1.90 (br, —$CH_2$—), 3.02 (t, —$CH_2$—$NH_2$), 3.70 (br, —$CH_2$—O—), 4.32 (t, —CH—CONH—).

(1-3)

Synthesis of $N_3$-Plys_(C)

By performing a reaction using the same method as in (1-1) above other than using 15 μL (0.0755 mmol) of the initiator 11-azide-3,6,9-trioxaundecane-1-amine, a white solid of $N_3$-PLys_(C) was obtained. From $^1$H-NMR, the degree of polymerization of the obtained compound was 130.4.

[Chem. 84]

$^1$H NMR (400 MHz, $D_2O$): δ 1.35-1.90 (br, —$CH_2$—), 3.02 (t, —$CH_2$—$NH_2$), 3.70 (br, —$CH_2$—O—), 4.32 (t, —CH—CONH—).

(1-4)

Synthesis of mPEG10k-PLys

The same polymerization reaction as in (1-1) above was carried out using, as an initiator, a polyethylene glycol having an —OMe group at one terminal and an —$NH_2$ group at the other terminal and having a number average molecular weight of 10,000 (hereinafter referred to as mPEG$_{10k}$-$NH_2$). 1.00 g (0.100 mmol) of mPEG$_{10k}$-$NH_2$ was weighed, added to a two-necked pear-shaped flask, and dissolved in 2 mL of benzene. Next, the solvent was evaporated off by freeze drying. 10 mL of distillation-purified DMSO was added thereto under an argon atmosphere and freeze-dried product was dissolved. Next, 1.61 g of NCA-Lys(Tfa) was weighed under an argon atmosphere and added to a separate two-necked pear-shaped flask. 16 mL of distillation-purified DMSO was added thereto and the NCA-Lys(Tfa) was dissolved. The NCA/DMSO solution was added to the PEG/DMSO solution using a syringe, and the mixture was stirred in a water bath at 40° C. for 2 days. The reaction solution was added dropwise to 500 mL of diethyl ether and purified by the reprecipitation method. The precipitate was collected by suction filtration and dried under reduced pressure overnight to obtain a white solid. The obtained polymer was added to a 100 mL pear-shaped flask and 100 mL of methanol, 2 mL of 5 M aqueous sodium hydroxide solution, and 8 mL of ultrapure water were added thereto and stirred overnight in a 40° C. water bath. The sample solution was put into a dialysis membrane (MWCO=3.5 kD) and dialyzed twice against a 1 L 0.01 M aqueous sodium hydroxide solution for 4 hours and then dialyzed four times against 3 L of ultrapure water for 4 hours. The dialyzed sample solution was added to a 500-mL pear-shaped flask, and the solvent was removed by freeze drying to obtain 1.3 g of a white solid of mPEG10k-PLys. From $^1$H-NMR, the degree of polymerization of the obtained compound was 52.1.

[Chem. 85]

$^1$H NMR (400 MHz, $D_2O$): δ 1.35-1.90 (br, —$CH_2$—), 3.02 (t, —$CH_2$—$NH_2$), 3.68 (br, —$CH_2$—O—), 4.32 (t, —CH—CONH—).

2-1

Synthesis of $N_3$—P[Lys(Gluconate)/Lys] (A)

1.3 g (0.066 mmol) of $N_3$-PLys_(A) obtained in (1-1) above, 2.73 g (15.3 mmol) of D-glucono-1,5-lactone, and 2.1 mL of TEA (15 mmol) were added to a 200 mL pear-shaped flask and dissolved in 100 mL of methanol, and the mixture was stirred under reflux for 24 hours. Thereafter, the solvent was evaporated off by a rotary evaporator, and the obtained precipitate was dissolved in 30 mL of 0.01 M hydrochloric acid. Thereafter, the solution was put into a dialysis membrane (MWCO=3.5 kD) and dialyzed once against 1 L of 0.01 M hydrochloric acid for 4 hours and then dialyzed four times against 3 L of ultrapure water for 4 hours. The dialyzed solution was filtered with a 0.45 μm filter and thereafter the solvent was evaporated by freeze drying to obtain 2.5 g of a white solid of $N_3$—P[Lys(Gluconate)/Lys]_(A). From $^1$H-NMR, the introduction rate of gluconic acid into the polymer was 98.0%. Further, from the degree of polymerization and the introduction rate, Mn=19,763. Furthermore, from the GPC, the polydispersity index (PDI) was 1.22.

[Chem. 86]

$^1$H NMR (400 MHz, $D_2O$): δ 1.30-2.05 (br, —$CH_2$—), 3.01 (br, —$CH_2$—$NH_2$), 3.25 (br, $CH_2$—NHCO—), 3.64-4.33 (br, —CH—OH,), 4.32 (br, —CH—CONH—).

(2-2)

Synthesis of $N_3$—P[Lys(Gluconate)/Lys] (B)

By performing a reaction using the same method as in (2-1) above other than using 1.6 g (0.054 mmol) of $N_3$-PLys_(B) instead of $N_3$-PLys_(A) and using 3.36 g (18.9 mmol) of D-glucono-1,5-lactone and 2.6 mL (19 mmol) of TEA, 3.0 g of a white solid of $N_3$—P[Lys(Gluconate)/Lys] (B) was obtained. From $^1$H-NMR, the introduction rate of gluconic acid into the polymer was 98.4%. Further, from the degree of polymerization and the introduction rate, Mn=29712. Furthermore, from the GPC, the polydispersity index (PDI) was 1.24.

[Chem. 87]

$^1$H NMR (400 MHz, $D_2O$) δ 1.30-2.05 (br, —$CH_2$—), 3.01 (br, —$CH_2$—$NH_2$), 3.25 (br, $CH_2$—NHCO—), 3.64-4.33 (br, —CH—OH,), 4.32 (br, —CH—CONH—).

(2-3)

Synthesis of $N_3$—P[Lys(Gluconate)/Lys] (C)

By performing a reaction using the same method as in (2-1) above other than using 1.5 g (0.038 mmol) of $N_3$-PLys_(C) instead of $N_3$-PLys_(A), and using 3.15 g (17.7 mmol) of D-glucono-1,5-lactone and 2.4 mL (17 mmol) of TEA, 2.9 g of a white solid of $N_3$—P[Lys (Gluconate)/Lys]_(C) was obtained. From $^1$H-NMR, the introduction rate of gluconic acid into the polymer was 97.8%. Further, from the degree of polymerization and the introduction rate, Mn=39636. Furthermore, from the GPC, the polydispersity index (PDI) was 1.35.
[Chem. 88]
$^1$H NMR (400 MHz, D$_2$O): δ 1.30-2.05 (br, —CH$_2$—), 3.01 (br, —CH$_2$—NH$_2$), 3.25 (br, CH$_2$—NHCO—), 3.64-4.33 (br, —CH—OH,), 4.32 (br, —CH—CONH—).
(2-4)
Synthesis of mPEG10k-P[Lys(Gluconate)/Lys]

1.3 g (0.050 mmol) of mPEG10k-PLys obtained in (1-4) above, 1.5 g (8.43 mmol) of D-glucono-1,5-lactone and 0.83 mL of TEA (8.4 mmol) were added to a 50 mL pear-shaped flask and dissolved in 10 mL of methanol that was added thereto. The mixture was stirred under reflux for 24 hours. Thereafter, the solvent was evaporated off by a rotary evaporator, and the obtained precipitate was dissolved in 10 mL of 0.01 M hydrochloric acid. The sample solution was put into a dialysis membrane (MWCO=3.5 kD) and dialyzed once against 1 L of 0.01 M hydrochloric acid for 4 hours and then dialyzed four times against 3 L of ultrapure water for 4 hours. The dialyzed solution was filtered with a 0.45 m filter and thereafter the solvent was evaporated by freeze drying to obtain 1.8 g of a white solid of mPEG10k-P[Lys(Gluconate)/Lys]. From $^1$H-NMR, the introduction rate of gluconic acid into the polymer was 98.9%. Furthermore, from the GPC, the polydispersity index (PDI) was 1.16.
[Chem. 89]
$^1$H NMR (400 MHz, D$_2$O): δ 1.30-2.05 (br, —CH$_2$—), 3.01 (br, —CH$_2$—NH$_2$), 3.25 (br, CH$_2$—NHCO—), 3.64-4.33 (br, —CH—OH,), 3.68 (br, —CH$_2$—O—), 4.32 (br, —CH—CONH—).

Example 19

Evaluation of N$_3$—P[Lys(Gluconate)/Lys]-BPA binding
<Reagents>
5 mol/L hydrochloric acid: Nacalai Tesque
5 mol/L aqueous sodium hydroxide solution: Wako Pure Chemical Industries, Ltd.
Sodium dihydrogen phosphate (NaH$_2$PO$_3$): Nacalai Tesque
[$^{10}$B-rich] 4-borono-L-phenylalanine (BPA): Katchem
Alizarin Red S (ARS): Wako Pure Chemical Industries, Ltd.
D-fructose: Wako Pure Chemical Industries, Ltd.
D-glucose: Nacalai Tesque
D-sorbitol: Tokyo Chemical Industry Co.,
<Equipment>
Fluorescence spectrophotometer (FP8300): JASCO Corporation The equilibrium constant of N$_3$—P[Lys(Gluconate)/Lys] and BPA was calculated using the ARS method according to the method described in Springsteen G., Wang B. H. Tetrahedron 58, 5291-5300 (2002). Initially, each of the following solutions A, B, C, and D were prepared.
Solution A: ARS (9.0×10$^{-6}$ M)
Solution B: ARS (9.0×10$^{-6}$ M), BPA (2.0×10$^{-3}$ M)
Solution C$_1$: ARS (9.0×10$^{-6}$ M), BPA (2.0×10$^{-3}$ M), Sorbitol (0.05 M)
Solution C$_2$: ARS (9.0×10$^{-6}$ M), BPA (2.0×10$^{-3}$ M), Glucose (1.5 M)
Solution C$_3$: ARS (9.0×10$^{-6}$ M), BPA (2.0×10$^{-3}$ M), Fructose (0.1 M)
Solution C$_4$: ARS (9.0×10- M), BPA (2.0×10$^{-3}$ M), N$_3$—P[Lys(Gluconate)/Lys]_(A) (0.01 M: side chain gluconic acid standard)
Solution C$_5$: ARS (9.0×10$^{-6}$ M), BPA (2.0×10$^{-3}$ M), N$_3$—P[Lys(Gluconate)/Lys]_(B) (0.01 M: side chain gluconic acid standard)
Solution C$_6$: ARS (9.0×10$^{-6}$ M), BPA (2.0×10$^{-3}$ M), N$_3$—P[Lys(Gluconate)/Lys]_(C) (0.01 M: side chain gluconic acid standard)

Figure 17:
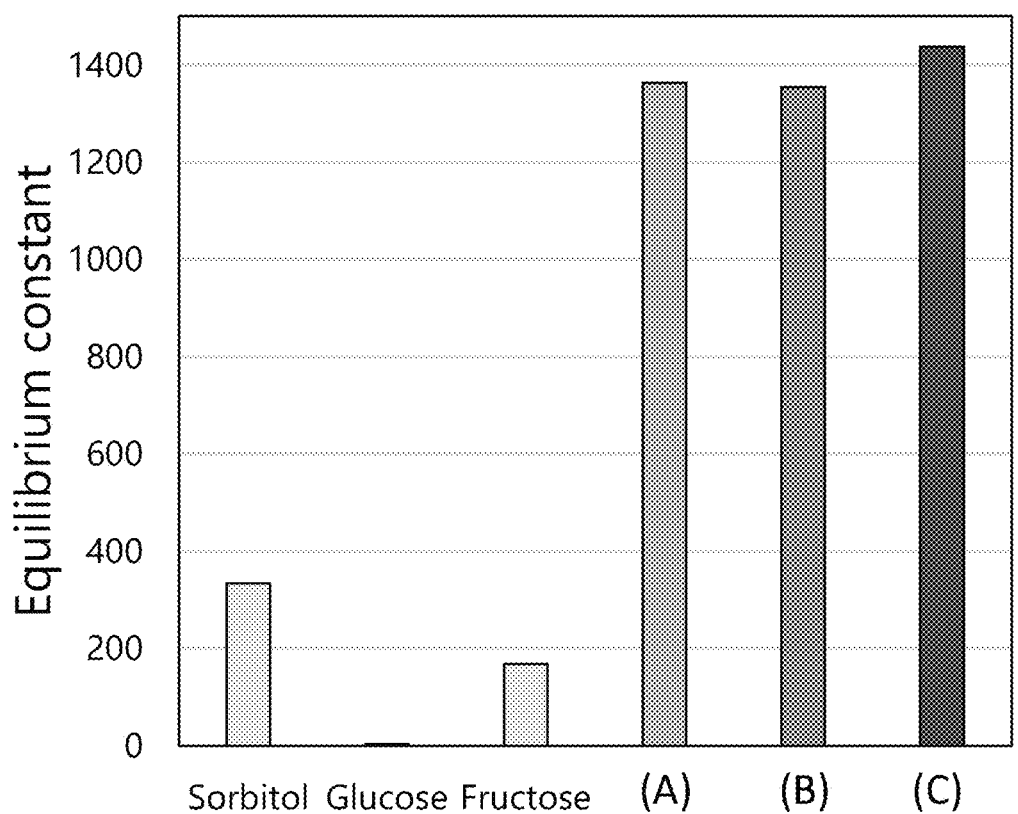
FIG. 17 shows the evaluation results of the coupling constants in EXAMPLE 19. In the figure, (A), (B), and (C) respectively represent $N_3$—P[Lys(Gluconate)/Lys]_(A), $N_3$—P[Lys(Gluconate)/Lys]_(B), and $N_3$—P[Lys(Gluconate)/Lys]_(C).

Solution A and Solution B were mixed at various ratios, and fluorescence was measured using disposable cells (PS, TGK) (E$_x$=468 nm, E$_m$=572 nm). The equilibrium constant K$_0$ of ARS-BPA was calculated from the obtained fluorescence intensity. Next, Solution B was mixed with Solution C at various ratios, and fluorescence was measured using disposable cells (E$_x$=468 nm, E$_m$=572 nm). The apparent binding constant of each compound and BPA was calculated using these results and the aforementioned K$_0$ value. The results are illustrated in FIG. 17.

It was established that the N$_3$—P[Lys(Gluconate)/Lys] synthesized in EXAMPLE 18 has high binding strength to BPA. The binding strength was about 4 times higher than that of sorbitol, which has a high binding strength among sugar compounds, and about 500 times higher than that of glucose, which is often present in the blood. From these results it is expected that the N$_3$—P[Lys(Gluconate)/Lys]-BPA will exhibit high stability in blood.

Example 20

Figure 18:
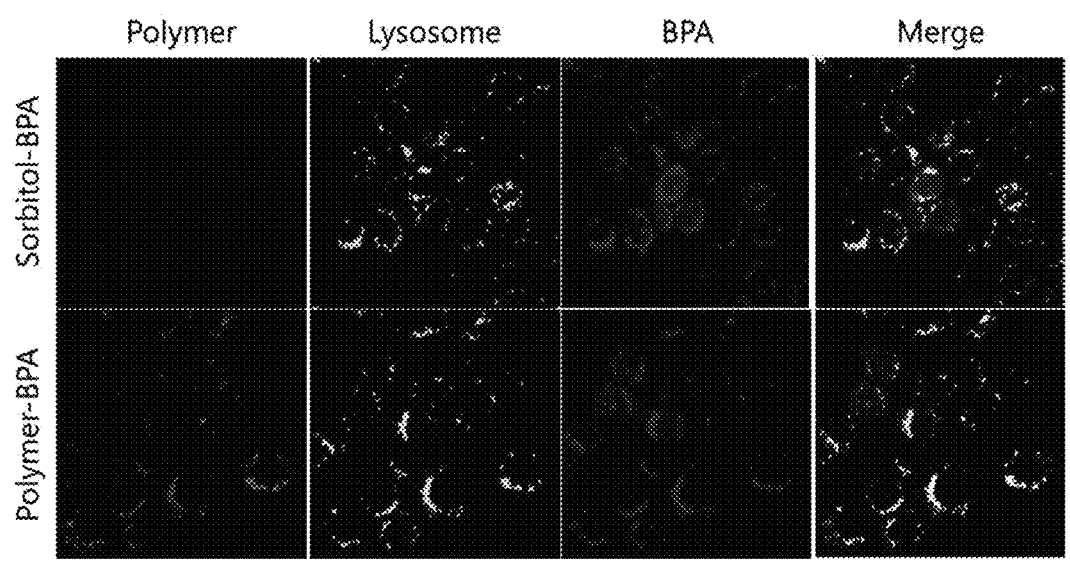
FIG. 18 shows confocal microscopy images of BxPC-3 cells treated with Cy5-P[Lys(Gluconate)/Lys](C)-BPA and Sorbitol-BPA. In the figure, "Polymer" refers to "Cy5-P[Lys(Gluconate)/Lys](C)".

Cellular Uptake of Cy5-P[Lys(Gluconate)/Lys]-BPA
(1) Synthesis of Cy5-P[Lys(Gluconate)/Lys]_(C)
100 mg (2.5 μmol) of N$_3$—P[Lys(Gluconate)/Lys]_(C) synthesized in EXAMPLE 18 (2-3) was weighed in a 6 mL vial and dissolved in 1.8 mL of DMSO. Next, 224 μL (2.8 mol) of 12.5 mg/mL Cy5-DBCO/DMSO solution was added thereto and the mixture was stirred overnight at room temperature. The reaction solution was put into an ultrafiltration membrane (MWCO=10 kD), 10 mL of ultrapure water was added thereto, and ultrafiltration was performed. 15 mL of ultrapure water was added and ultrafiltration was performed a further two times. In order to further purify the ultrafiltration-purified sample, the sample was purified using a PD-10 column (GE Healthcare), the collected sample solution was freeze-dried to evaporate the solvent, and 97 mg of Cy5-P[Lys(Gluconate)/Lys](C) was obtained as a blue solid.
(2) Evaluation of Cellular Uptake of Cy5-P[Lys(Gluconate)/Lys]_(C)-BPA BxPC-3 cells were inoculated at 5×10$^4$ cells/well on an 8-well plate (Lab-Tek Chambered #1.0 borosilicate Coverglass system) for microscopic observation and incubated overnight at 37° C. under a 5% CO$_2$ atmosphere (culture medium: RPMI-1640 containing 10% FBS and 1% Penicilin-Streptmycin). After incubation, the culture medium was removed using an aspirator, and 500 μL of the following sample solutions were added.
Sorbitol-BPA: BPA (3.03 mM), Sorbitol (3.64 mM)/10% PBS-90% RPMI culture medium Cy5-P[Lys(Gluconate)/Lys](C)-BPA: BPA (3.03 mM), Cy5-P[Lys(Gluconate)/Lys](C)·(3.64 mM: side chain gluconic acid standard)/10% PBS-90% RPMI culture medium The above sample solutions were adjusted to a 10-fold concentration with a phosphate buffer (10 mM NaH$_2$PO$_4$, 140 mM NaCl, pH 7.4) and then diluted with RPMI culture medium before use. The sample solutions were added thereto and then incubated for 1 hour. Thereafter, the sample solutions were removed using an aspirator, and 20 μM DAHMI, 50 nM LysoTracker Green/PBS solution (500 μL) was added and incubation was performed for 30 min. Thereafter, the solutions were removed using an aspirator and washing was performed three times with PBS 500 μL. After washing three times, 500 μL of PBS was added thereto, and then fluorescence was observed with a confocal microscope. The results are illustrated in FIG. 18.

As a result of microscopic observation, it was confirmed that Cy5-P[Lys(Gluconate)/Lys](C) was localized in the endosome, not in the entire cytoplasm. Since Cy5-P[Lys(Gluconate)/Lys](C) was localized with BPA, this suggests that Cy5-P[Lys(Gluconate)/Lys](C)-BPA is incorporated into cells by endocytosis.

Example 21

Pharmacokinetics of $N_3$—P[Lys(Gluconate)/Lys]-BPA and sorbitol-BPA
<Reagents, Cells, and Animals>
$N_3$—P[Lys(Gluconate)/Lys]_(A), $N_3$—P[Lys(Gluconate)/Lys]_(B), $N_3$—P[Lys(Gluconate)/Lys]_(C) and mPEG10k-P[Lys(Gluconate)/Lys] synthesized in EXAMPLE 18
D-sorbitol: Tokyo Chemical Industry Co.,
5 mol/L hydrochloric acid: Nacalai Tesque
5 mol/L sodium hydroxide (for mass spectrometry): Wako Pure Chemical Industries, Ltd.
L-4-boronophenyl-alanine (BPA): Katchem
Nitric acid (1.42): Wako Pure Chemical Industries, Ltd.
CT26 cells (mouse colon cancer cell line): American Type Culture Collection (Manassas, Va.)
BALB/c mouse: Charles River Japan
<Equipment>
Agilent 7900 ICP-MS: Agilent Technology Co., Ltd.
Heavy Water Neutron Irradiation Facility: KUR Subcutaneous tumor models were prepared by subcutaneously injecting CT-26 cells into BALB/c mice at $1.0 \times 10^5$ cells/mouse. Once the tumor size had reached about 200 $mm^3$, 200 L of the following samples solutions (pH 7.4) were administered to the mice through the tail vein (BPA 10 mg/mouse). The following sample solutions were prepared by dissolving sugar or polymer and BPA in an appropriate amount of ultrapure water, adding aqueous sodium hydroxide solution and making the solution alkaline, completely dissolving the solute and then adding hydrochloric acid to adjust the pH to 7.4, adding ultrapure water, diluting the solutions to the final concentrations shown below, and performing filter sterilization using a 0.22 m filter.

$N_3$—P[Lys(Gluconate)/Lys]_(A)-BPA (BPA 240 mM)
$N_3$—P[Lys(Gluconate)/Lys]_(B)-BPA (BPA 240 mM)
$N_3$—P[Lys(Gluconate)/Lys]_(C)-BPA (BPA 240 mM)
mPEG10k-P[Lys(Gluconate)/Lys]-BPA (BPA 240 mM)
Sorbitol-BPA (BPA 240 mM, Sorbitol 288 mM)

Figure 19:
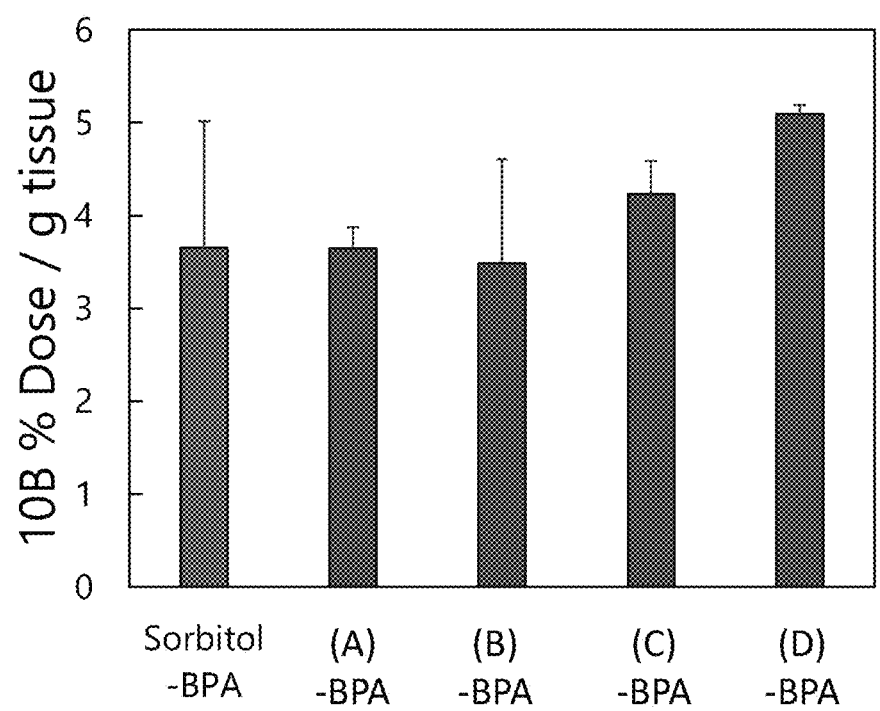
FIG. 19 shows the results of accumulation in tumors of $N_3$—P[Lys(Gluconate)/Lys]_(A)-BPA ((A)-BPA in the figure), $N_3$—P[Lys(Gluconate)/Lys] (B)-BPA ((B)-BPA in the figure), $N_3$—P[Lys(Gluconate)/Lys]_(C)-BPA ((C)-BPA in the figure), mPEG10k-P[Lys(Gluconate)/Lys]_-BPA ((D)-BPA in the figure) and Sorbitol-BPA. The data is shown as mean±S.D. (n=3).

Three hours after administration of the sample, the mice were dissected and the tumors were removed. The tumors were placed in a 14 mL tube (PP round tube, Falcon), and 1 mL of nitric acid (1.42) was added. Thereafter, each sample was incubated at 50° C. for 15 minutes, 70° C. for 15 minutes, and 90° C. for 1 hour. Ultrapure water was added up to 10 mL. After filtration through a hydrophobic filter, the amount of boron was quantified using ICP-MS. The results of pharmacokinetic analysis of CT-26 transplanted mice are illustrated in FIG. 19.

Example 22

Antitumor Effect of $N_3$—P[Lys(Gluconate)/Lys]-BPA
CT-26 cells were subcutaneously implanted ($1.0 \times 10^5$ cells/mouse) near the right thigh of BALB/c mice, and 200 µL of the following samples were slowly administered through the tail vein of mice with a tumor size of about 50 to 100 $mm^3$ (BPA 10 mg/mouse).

$N_3$—P[Lys(Gluconate)/Lys](B)-BPA (BPA 240 mM)
$N_3$—P[Lys(Gluconate)/Lys](C)-BPA (BPA 240 mM)
Sorbitol-BPA (BPA 240 mM, Sorbitol 288 mM)

In the neutron irradiation group, neutron irradiation was performed for 50 minutes only around the right thigh of the mouse 2.5 hours after sample administration. With the day of irradiation set as the first day, the tumor diameter was measured every 2 to 3 days with electronic calipers and the body weight was measured with an electronic balance for a total of 30 days. The measured tumor diameter was used in an elliptic volume approximation formula ($ab^2 \times ½$, where a is the long side and b is the short side) to give the tumor volume. The evaluated groups are summarized below (n=6).

Control (COLD): untreated group.
Control (HOT): only irradiated with neutrons.
Sorbitol-BPA (HOT): injected with sorbitol-BPA then irradiated with neutrons 2.5 hours thereafter.
$N_3$—P[Lys(Gluconate)/Lys](B)-BPA (HOT): injected with $N_3$—P[Lys(Gluconate)/Lys](B)-BPA then irradiated with neutrons 2.5 hours thereafter.
$N_3$—P[Lys(Gluconate)/Lys](C)-BPA (HOT): injected with $N_3$—P[Lys(Gluconate)/Lys](C)-BPA then irradiated with neutrons 2.5 hours thereafter.

Figure 20:
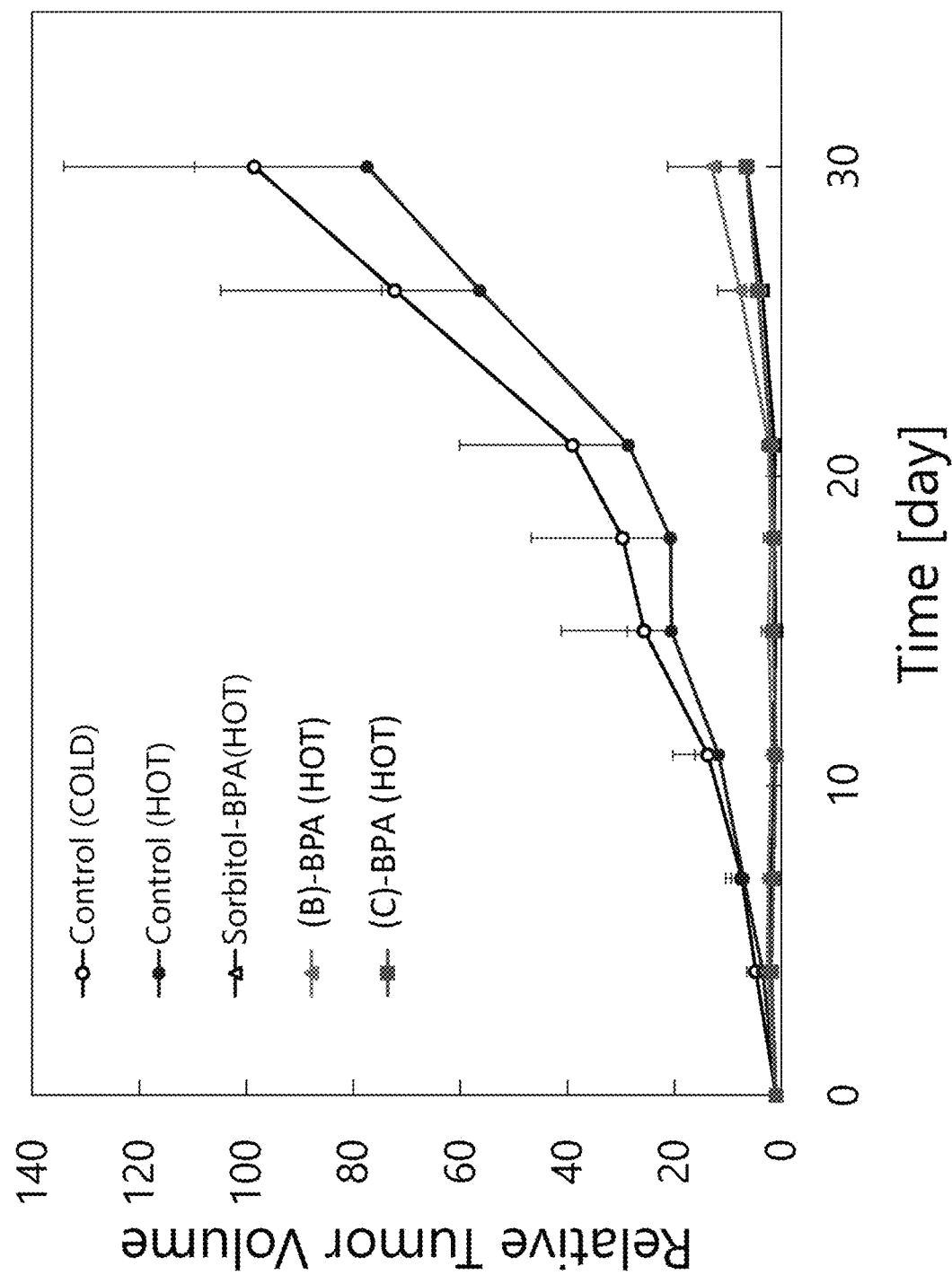
FIG. 20 shows the relative change in size of tumors over time after administration of the samples in EXAMPLE 22. The data is shown as mean±S.D. (n=6).
Figure 21:
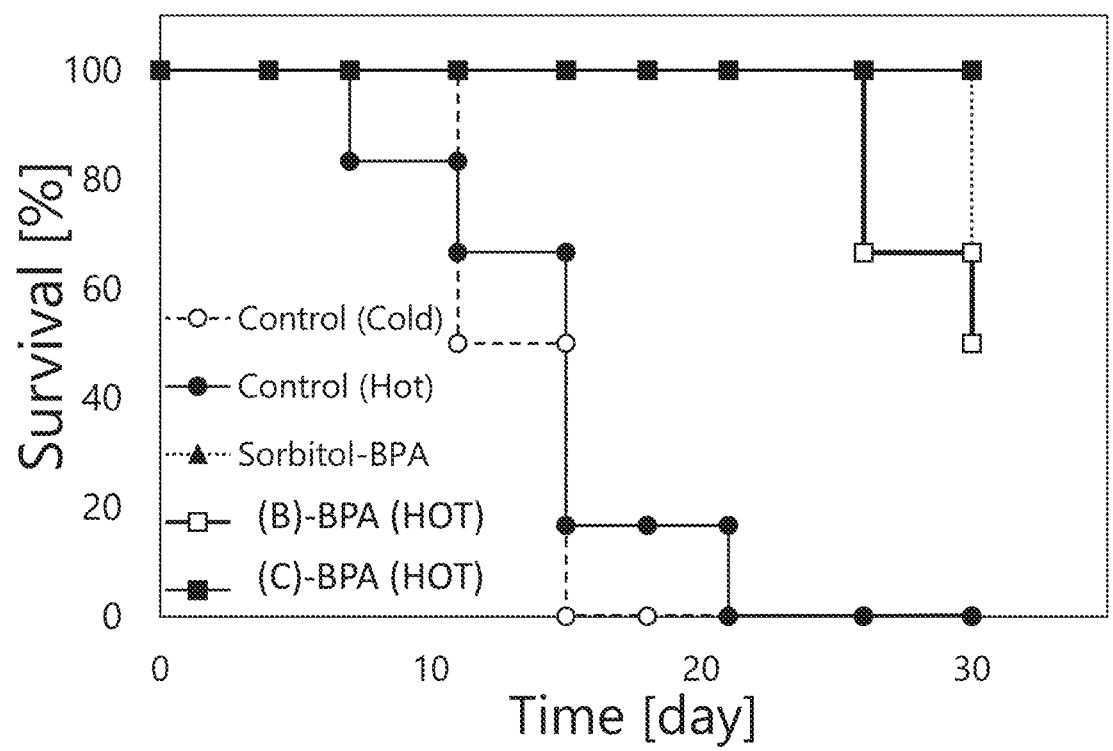
FIG. 21 shows Kaplan-Meier curves of relative tumor size after sample administration in EXAMPLE 22.

The change in tumor size over time and the Kaplan-Meier curves thereof are shown in FIGS. 20 and 21 (survival curve was created with a tumor volume of 1600 $mm^3$ as the end point). Sorbitol-BPA, $N_3$—P[Lys(Gluconate)/Lys](B)-BPA (HOT) and $N_3$—P[Lys(Gluconate)/Lys](C)-BPA (HOT) showed higher antitumor effects and survival rates compared to the control groups (Control (COLD) and Control (HOT)). In addition, $N_3$—P[Lys(Gluconate)/Lys](C)-BPA (HOT) showed a higher survival rate compared to other groups.

Example 23

Synthesis of P[VA(RGD)/VA]

A cyclic RGDfK peptide having a strong affinity for $\alpha_v\beta_3$ integrin, which was reported to be overexpressed in tumor-associated blood vessels and tumor cells, was introduced into a PVA side chain.

[Chem. 90]

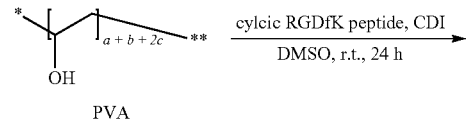

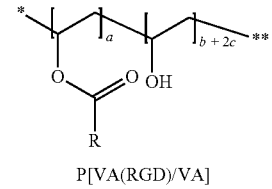

P[VA(RGD)/VA]

-continued

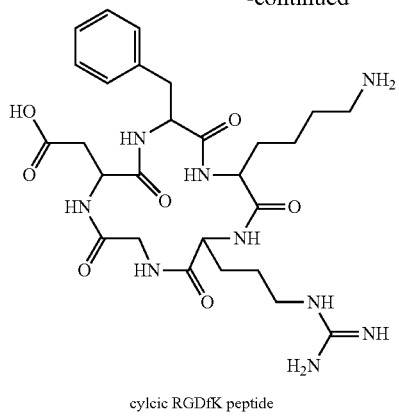

cylcic RGDfK peptide

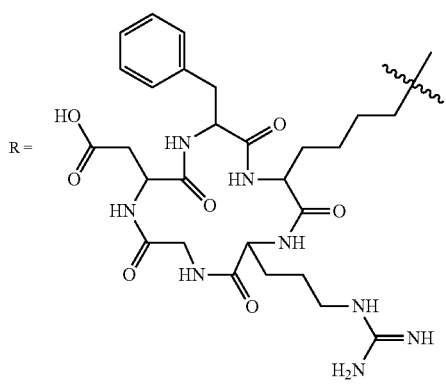

R =

<Reagents>

Unless otherwise specified, commercially available reagents and solvents were used as they were.

PVA (Mn=9200): synthesized according to the method of EXAMPLE 1 (2).

Cyclic RGDfK peptide: purchased from Synpeptide

CDI: purchased from Sigma Aldrich

DMSO: purchased from Wako Pure Chemical Industries, Ltd.

DMSO-$d_6$: purchased from Wako Pure Chemical Industries, Ltd.

PVA 100 mg and CDI 17.7 mg were dissolved in 10 mL of DMSO, and the mixture was stirred at room temperature for 2 hours. Thereafter, 19.7 mg of cyclic RGDfK peptide was added thereto, and stirred for 24 hours at room temperature. The product was dialyzed against water three times. After dialysis, the sample was freeze-dried and collected. The results of $^1$H-NMR analysis revealed that one or two cyclic RGDfK peptides were bound to one polymer.

[Chem. 91]

$^1$H-NMR (400 MHz, DMSO-$d_6$): δ 7.28-7.12 (Ph-H of cyclic RGDfK), 4.76-4.18 (—OH), 4.08-3.75 (—CHCH$_2$— of the polymer backbone), 4.7-3.5 (CHα of cyclic RGDfK), 1.78-1.08 (—CHCH$_2$— of the polymer backbone), 1.8-1.4 (—CH$_2$CH$_2$CH$_2$NH— of cyclic RGDfK).

Example 24

Evaluation of Tumor Accumulation of P[VA(RGD)/VA]-BPA

<Reagents, Cells, and Animals>

P[VA(RGD)/VA]: produced in EXAMPLE 23

BPA:KatChem

BxPC3 cells: American Type Culture Collection (Manassas, Va.)

BALB/c nude mouse: Charles River Japan

BxPC3 cells were subcutaneously injected into a BALB/c nude mouse at 5×10$^6$ cells/mouse. Once the tumor size had reached about 200 mm$^3$, the following sample was intravenously injected (BPA 8 mg/mouse).

P[VA(RGD)/VA]-BPA (BPA concentration: 191 mM, P[VA(RGD)/VA] diol concentration: 91 mM) in PBS (pH 10)

Six hours after intravenous injection, the mice were euthanized by cervical dislocation, and then dissected to remove the tumors. The tumors were placed in a 10 mL falcon tube, and 1 mL of 70% nitric acid was added. Thereafter, each sample was incubated at 50° C. for 15 minutes, 70° C. for 15 minutes, and 90° C. for 1 hour. The samples were diluted to 10 mL with pure water, filtered through a hydrophobic filter, then the amount of boron was quantified using ICP-MS. As a result, P[VA(RGD)/VA]-BPA showed a high accumulation of 6.2±2.4% dose/g tumor in the tumor even 6 hours after administration.

INDUSTRIAL APPLICABILITY

According to the present invention, it is possible to deliver a large amount of boron in a tumor-selective manner in BNCT. Further, this can be applied to fluorine-modified BPA as a diagnostic agent and can also be used as a boron-based diagnostic agent.

The invention claimed is:

1. A p-boronophenylalanine derivative comprising:
a polymer linked, either directly or via a linker, to a group represented by formula (I) below

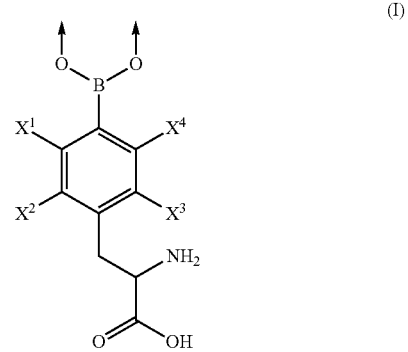

wherein,
the arrows indicate a bond with an adjacent atom, and $X^1$ to $X^4$ are each independently H, $^{18}$F, or $^{19}$F,
wherein the linker contains at least 2 hydroxy groups or at least 2 carboxyl groups;
wherein the linker is a $C_{1-40}$ alkylene group substituted with 2 hydroxy groups, and methyl groups in the $C_{1-40}$ alkylene group are independently and optionally substituted with 1 to 10 oxo groups, halogens, or hydroxy groups, and adjacent methylene groups are optionally joined to one another through 1 to 10 unsaturated bonds, and from among the methylene groups, 1 to 20 methylene groups are optionally exchanged for NH, N($C_{1-10}$ alkyl), O, S, $C_{6-14}$ arylene, or 5- to 10-membered heteroarylene; or wherein the linker includes a polyol, a sugar, a sugar alcohol, glucamine, or a compound represented by formula (X-a) or formula (XII-a):

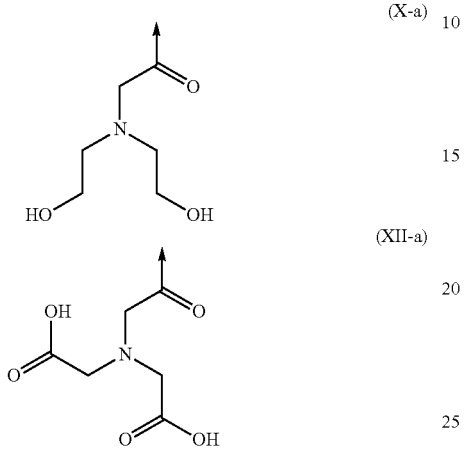

wherein the arrows indicate a bond with an adjacent atom.

2. The p-boronophenylalanine derivative according to claim 1, wherein two or more of the groups represented by formula (I) are linked directly or via the linker to the polymer, and
wherein the groups represented by formula (I) may be the same or different.

3. The p-boronophenylalanine derivative according to claim 1, wherein the number average molecular weight thereof is 1,000 Da or more.

4. The p-boronophenylalanine derivative according to any one of claims 1 to 3, wherein the polymer is selected from the group consisting of polyvinyl alcohol, polyester, polyether, polyacrylate, polyacrylamide, polypeptide, polysaccharide, and copolymers thereof.

5. The p-boronophenylalanine derivative according to any one of claims 1 to 3, wherein the polymer is a polyvinyl alcohol.

6. The p-boronophenylalanine derivative according to claim 5, wherein the p-boronophenylalanine derivative is represented by formula (II) below or a pharmaceutically acceptable salt thereof:

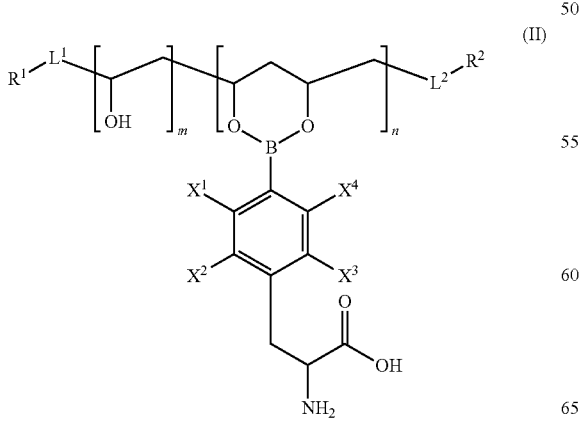

wherein, $X^1$ to $X^4$ are each independently H, $^{18}F$, or $^{19}F$, $L^1$ and $L^2$ are each independently a linker or absent, $R^1$ and $R^2$ are each independently hydrogen, a hydroxy group, a carboxyl group, an amino group, a $C_{1-10}$ alkyl group that may be substituted with a halogen, a $C_{1-10}$ alkoxy group that may be substituted with a halogen, a thiol group, a cyano group, an azide group, a —CH($OA^1$)$_2$, or a detectable label, $A^1$ is a $C_{1-6}$ alkyl group, m=0 to 3,998, n=1 to 2,000, m+2n=10 to 4,000, and the order of the repeating units is arbitrary, wherein the linker is a $C_{1-40}$ alkylene group, the methyl groups in the $C_{1-40}$ alkylene group are independently and optionally substituted with 1 to 10 oxo groups or halogens, and adjacent methylene groups are optionally joined to one another through 1 to 10 unsaturated bonds, and from among the methylene groups, 1 to 20 methylene groups are optionally exchanged for NH, N($C_{1-10}$ alkyl), O, S, $C_{6-14}$ arylene, 5- to 10-membered heteroarylene, or polyoxyalkylene having a degree of polymerization of 2 to 2,000, 2 to 1,000, 2 to 500, 2 to 400, 2 to 300, 2 to 200, 2 to 100, 2 to 50, or 2 to 10; or wherein the linker has the following structure:

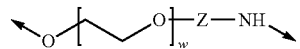

wherein w is 1 to 2,000 and Z is a $C_{1-5}$ alkylene group; or

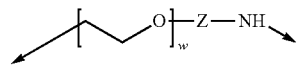

wherein w is 1 to 2,000 and Z is a $C_{1-5}$ alkylene group.

7. The p-boronophenylalanine derivative according to any one of claims 1 to 3, wherein the polymer is a polypeptide.

8. The p-boronophenylalanine derivative according to claim 7, wherein the p-boronophenylalanine derivative is represented by formula (III) below or a pharmaceutically acceptable salt thereof;

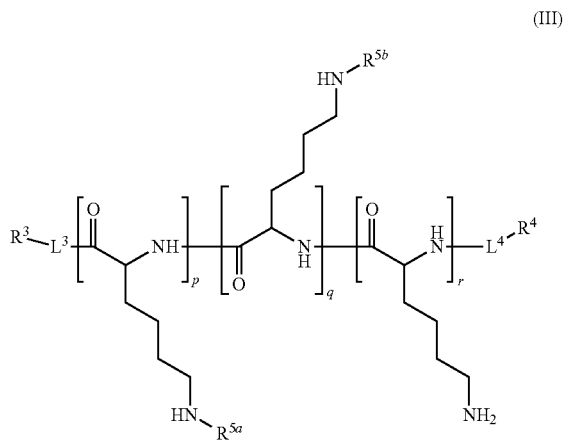

wherein,

L³ and L⁴ are each independently a linker or absent,

R³ and R⁴ are each independently hydrogen, a hydroxy group, a carboxyl group, an amino group, a $C_{1-10}$ alkyl group that may be substituted with a halogen, a $C_{1-10}$ alkoxy group that may be substituted with a halogen, a thiol group, a cyano group, an azide group, a —CH(OA¹)₂, or a detectable label, A¹ is a $C_{1-6}$ alkyl group, $R^{5a}$ are each independently a group represented by (IV-a) or (IV-b) below,

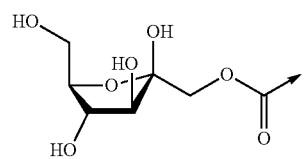
(IV-a)

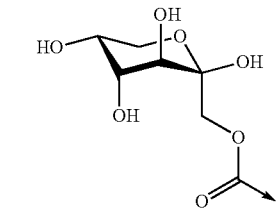
(IV-b)

wherein, the arrows indicate a bond with NH, $R^{5b}$ are each independently a group selected from the group consisting of groups represented by the following formulas (IV-c) to (IV-g),

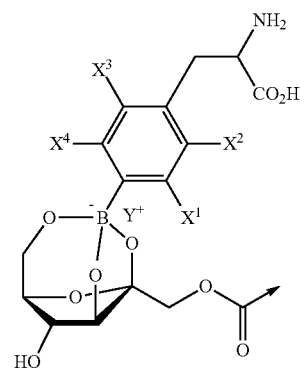
(IV-c)

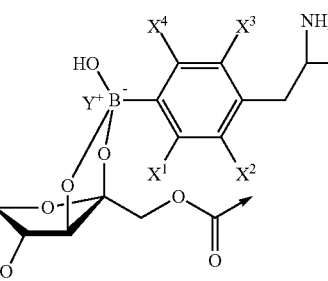
(IV-d)

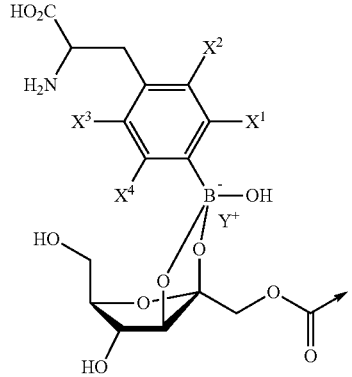
(IV-e)

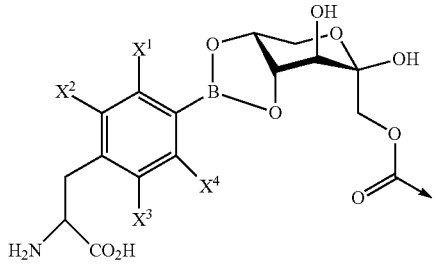
(IV-f)

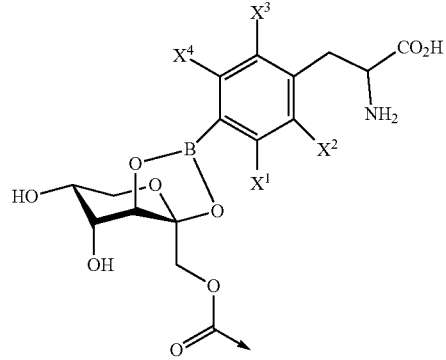
(IV-g)

wherein the arrows indicate a bond with NH,

X¹ to X⁴ each independently represent H, ¹⁸F or ¹⁹F,

Y⁺ represents H⁺, an alkali metal ion, or a tetra-$C_{1-6}$ alkyl-ammonium ion, p=0 to 299, q=1 to 300, r=0 to 299, p+q+r=10 to 300, and the order of the repeating units is arbitrary, wherein the linker is a $C_{1-40}$ alkylene group, the methyl groups in the $C_{1-40}$ alkylene group are independently and optionally substituted with 1 to 10 oxo groups or halogens, and adjacent methylene groups are optionally joined to one another through 1 to 10 unsaturated bonds, and from among the methylene groups, 1 to 20 methylene groups are optionally exchanged for NH, N($C_{1-10}$ alkyl), O, S, $C_{6-14}$ arylene, 5- to 10-membered heteroarylene, or polyoxyalkylene having a degree of polymerization of 2 to 2,000, 2 to 1,000, 2 to 500, 2 to 400, 2 to 300, 2 to 200, 2 to 100, 2 to 50, or 2 to 10; or wherein the linker has the following structure:

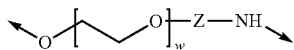

wherein w is 1 to 2,000 and Z is a $C_{1-5}$ alkylene group; or

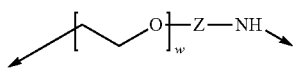

wherein w is 1 to 2,000 and Z is a $C_{1-5}$ alkylene group.

9. The p-boronophenylalanine derivative according to claim 7, wherein the p-boronophenylalanine derivative is represented by formula (V) below or a pharmaceutically acceptable salt thereof,

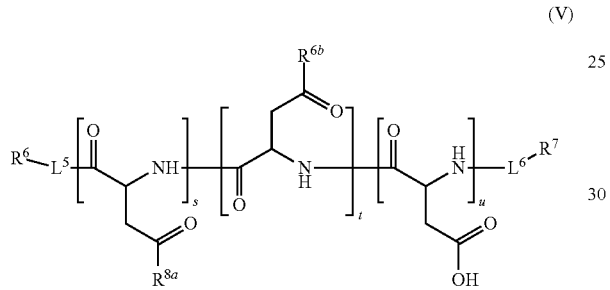

wherein, $L^5$ and $L^6$ are each independently a linker or absent, $R^6$ and $R^7$ are each independently a hydrogen, a hydroxy group, a carboxyl group, an amino group, a $C_{1-10}$ alkyl group that may be substituted with a halogen, a $C_{1-10}$ alkoxy group that may be substituted with a halogen, a thiol group, a cyano group, an azide group, a —CH$(OA^1)_2$ or a detectable label, $A^1$ is a $C_{1-6}$ alkyl group, $R^{8a}$ is a group represented by (VI-a) below,

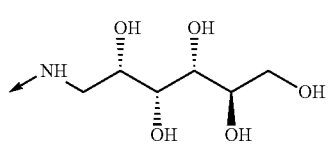

wherein, the arrow indicates a bond with a carbonyl carbon, $R^{8b}$ are each independently a group selected from the group consisting of groups represented by formulas (VI-b) to (VI-h) below,

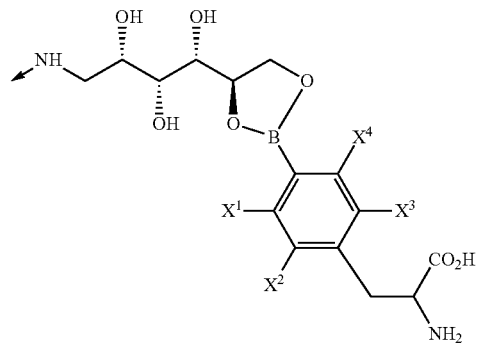

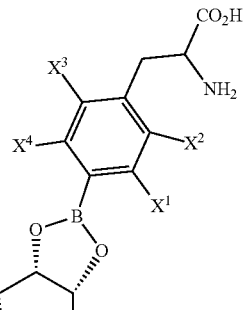

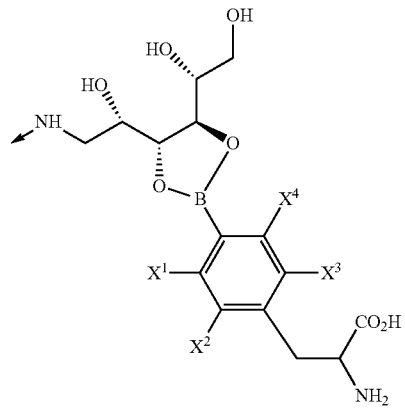

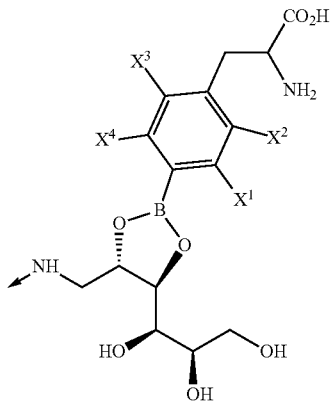

-continued

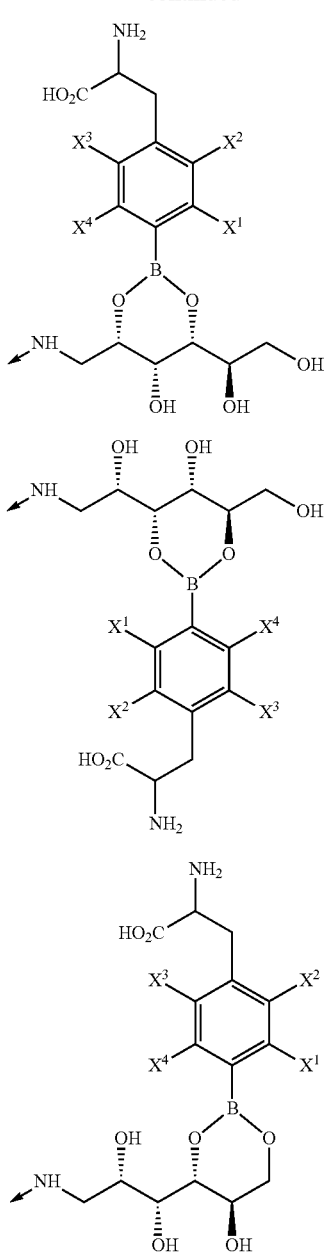

wherein,
the arrows indicate a bond with a carbonyl carbon,
$X^1$ to $X^4$ are each independently H, $^{18}F$, or $^{19}F$,
s=0 to 299,
t=1 to 300,
u=0 to 299,
s+t+u=2 to 300, and
the order of the repeating units is arbitrary;
wherein the linker is a $C_{1-40}$ alkylene group, the methyl groups in the $C_{1-40}$ alkylene group are independently and optionally substituted with 1 to 10 oxo groups or halogens, and adjacent methylene groups are optionally joined to one another through 1 to 10 unsaturated bonds, and from among the methylene groups, 1 to 20 methylene groups are optionally exchanged for NH, N($C_{1-10}$ alkyl), O, S, $C_{6-14}$ arylene, 5- to 10-membered heteroarylene, or polyoxyalkylene having a degree of polymerization of 50 to 500; or wherein the linker has the following structure:

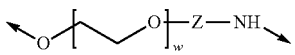

wherein w is 1 to 2,000 and Z is a $C_{1-5}$ alkylene group; or

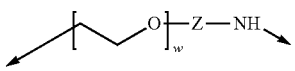

wherein w is 1 to 2,000 and Z is a $C_{1-5}$ alkylene group.

10. The p-boronophenylalanine derivative according to claim 7, wherein the p-boronophenylalanine derivative is represented by formula (XX) below or a pharmaceutically acceptable salt thereof,

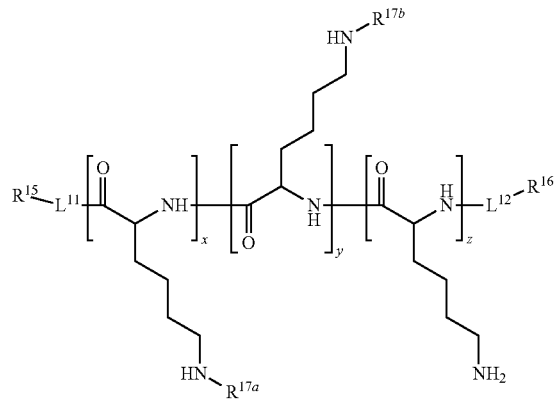

(XX)

wherein
$L^{11}$ and $L^{12}$ are each independently a linker or absent,
$R^{15}$ and $R^{16}$ are each independently hydrogen, a hydroxy group, a carboxyl group, an amino group, a $C_{1-10}$ alkyl group that may be substituted with a halogen, a $C_{1-10}$ alkoxy group that may be substituted with a halogen, a thiol group, a cyano group, an azide group, a —CH$(OA^1)_2$ or a detectable label,
$A^1$ is a $C_{1-6}$ alkyl group,
$R^{17a}$ is a group represented by the formula (XXI-a) below,

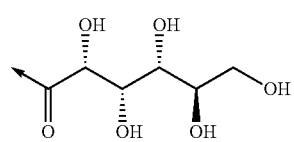

(XXI-a)

wherein, the arrow indicates a bond with NH,
$R^{17b}$ are each independently a group selected from the group consisting of groups represented by formulas (XXI-b) to (XXI-h) below, (XXI-b)
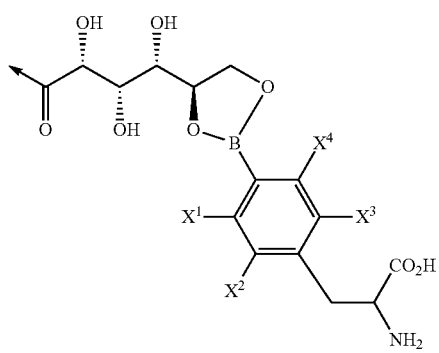

(XXI-c)
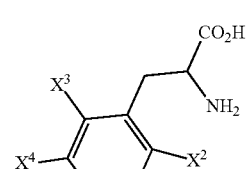
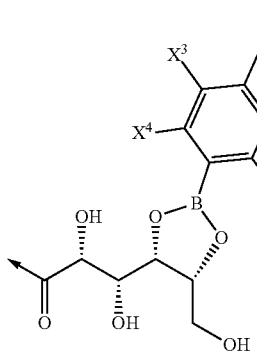

(XXI-d)
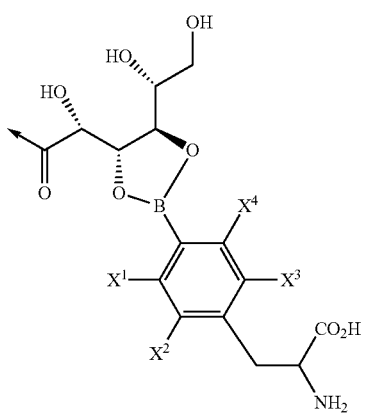

(XXI-e)
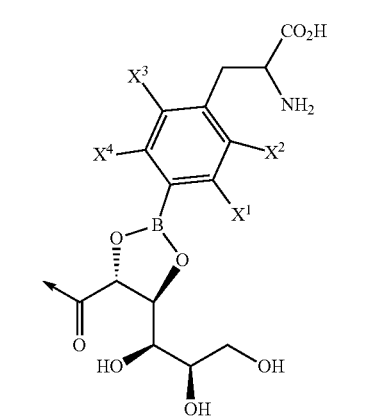

(XXI-f)
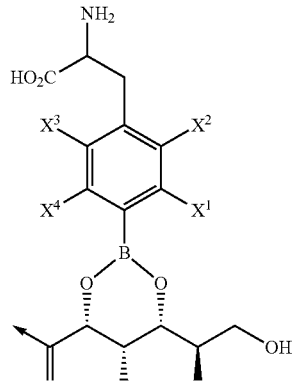

(XXI-g)
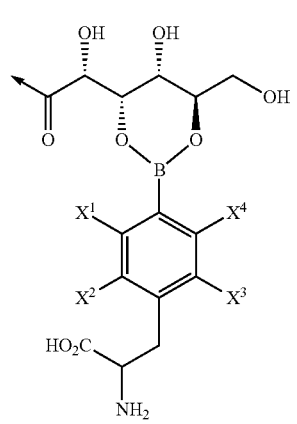

(XXI-h)
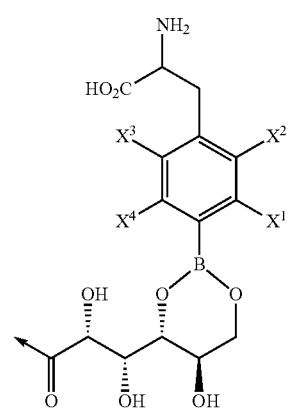

wherein,
the arrows indicate a bond with NH,
$X^1$ to $X^4$ are each independently H, $^{18}$F, or $^{19}$F,
x=0 to 299,
y=1 to 300,
z=0 to 299,
x+y+z=10 to 300, and
the order of the repeating units is arbitrary wherein the linker is a $C_{1-40}$ alkylene group, and the methyl groups in the $C_{1-40}$ alkylene group are independently and optionally substituted with 1 to 10 oxo groups or halogens, and adjacent methylene groups are optionally joined to one another through 1 to 10 unsaturated bonds, and from among the methylene groups, 1 to 20 methylene groups are optionally exchanged for NH, N($C_{1-10}$ alkyl), O, S, a $C_{6-14}$ arylene, 5- to 10-membered heteroarylene, or a polyoxyalkylene having a degree of polymerization of 2 to 1,000, 2 to 500, 2 to 400, 2 to 300, 2 to 200, 2 to 100, 2 to 50, or 2 to 10; or wherein the linker has the following structure:

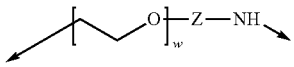

wherein w is 1 to 2,000 and Z is a $C_{1-5}$ alkylene group.

11. The p-boronophenylalanine derivative according to claim 5, wherein the p-boronophenylalanine derivative is represented by formula (XXII) below or a pharmaceutically acceptable salt thereof,

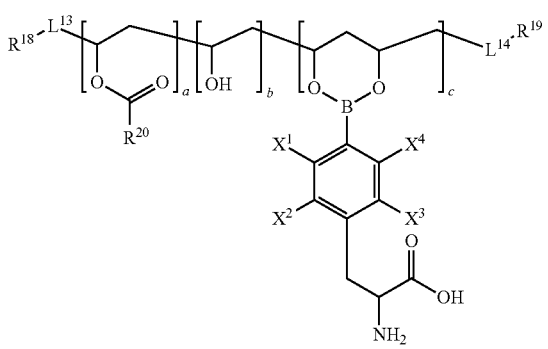

(XXII)

wherein
$X^1$ to $X^4$ are each independently H, $^{18}F$ or $^{19}F$,
$L^{13}$ and $L^{14}$ are each independently a linker or absent,
$R^{18}$ and $R^{19}$ are each independently a hydrogen, a hydroxy group, a carboxyl group, an amino group, a $C_{1-10}$ alkyl group that may be substituted with a halogen, a $C_{1-10}$ alkoxy group that may be substituted with a halogen, a thiol group, a cyano group, an azide group, a —CH(OA$^1$)$_2$ or a detectable label,
$A^1$ is a $C_{1-6}$ alkyl group,
$R^{20}$ are each independently a $C_{1-10}$ alkyl group that may be substituted with a halogen, an —NR$^{21}$R$^{22}$ group, or the following group,

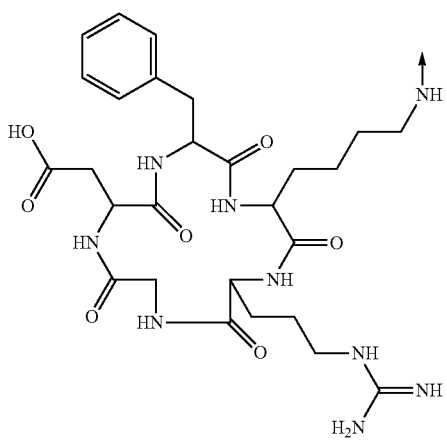

wherein, the arrow indicates a bond with a carbonyl carbon,
$R^{21}$ and $R^{22}$ are each independently a hydrogen or a $C_{1-10}$ alkyl group that may be substituted with a halogen,
a=1 to 3,998,
b=0 to 3,997,
c=1 to 2,000,
a+b+2c=10 to 4,000, and
the order of the repeating units is arbitrary,
wherein the linker is a $C_{1-40}$ alkylene group, and methyl groups in the $C_{1-40}$ alkylene group are independently and optionally substituted with 1 to 10 oxo groups or halogens, and adjacent methylene groups are optionally joined to one another through 1 to 10 unsaturated bonds, and from among the methylene groups, 1 to 20 methylene groups are optionally exchanged for NH, N($C_{1-10}$ alkyl), O, S, a $C_{6-14}$ arylene, 5- to 10-membered heteroarylene, or polyoxyalkylene having a degree of polymerization of 2 to 2,000, 2 to 1,000, 2 to 500, 2 to 400, 2 to 300, 2 to 200, 2 to 100, 2 to 50, or 2 to 10; or
wherein the linker has the following structure:

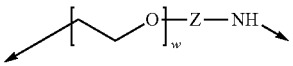

wherein w is 1 to 2,000 and Z is a $C_{1-5}$ alkylene group.

12. A composition comprising the p-boronophenylalanine derivative according to claim 1.

13. A method of treating a tumor in a subject in need thereof, comprising administering to the subject a therapeutically effective amount of a composition according to claim 12.

14. A method of diagnosing or detecting a tumor in a subject in need thereof, comprising administering to the subject an effective amount of a composition according to claim 12.

15. A kit for producing the p-boronophenylalanine derivative according to claim 1 comprising a compound represented by formula (VII)

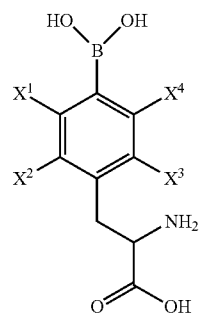

(VII)

wherein,
$X^1$ to $X^4$ are each independently H, $^{18}F$ or $^{19}F$, and
a polymer that can react with the compound represented by formula (VII) to form a p-boronophenylalanine derivative according to claim 1.

* * * * *

UNITED STATES PATENT AND TRADEMARK OFFICE
CERTIFICATE OF CORRECTION

| | | |
|---|---|---|
| PATENT NO. | : 11,555,082 B2 | Page 1 of 1 |
| APPLICATION NO. | : 16/963864 | |
| DATED | : January 17, 2023 | |
| INVENTOR(S) | : Nobuhiro Nishiyama et al. | |

It is certified that error appears in the above-identified patent and that said Letters Patent is hereby corrected as shown below:

On the Title Page

(73) Assignee reads:
TOKYO INSTITUTE OF TECHNOLOGY, Osaka (JP)

(73) Assignee should read:
--TOKYO INSTITUTE OF TECHNOLOGY, Tokyo (JP)
STELLA PHARMA CORPORATION, Osaka (JP)--

Signed and Sealed this
Eighteenth Day of July, 2023

Katherine Kelly Vidal
*Director of the United States Patent and Trademark Office*